US012312297B2

(12) United States Patent
Ishizawa

(10) Patent No.: US 12,312,297 B2
(45) Date of Patent: May 27, 2025

(54) O-SUBSTITUTED SERINE DERIVATIVE PRODUCTION METHOD

(71) Applicant: Chugai Seiyaku Kabushiki Kaisha, Tokyo (JP)

(72) Inventor: Takenori Ishizawa, Kanagawa (JP)

(73) Assignee: CHUGAI SEIYAKU KABUSHIKI KAISHA, Tokyo (JP)

(*) Notice: Subject to any disclaimer, the term of this patent is extended or adjusted under 35 U.S.C. 154(b) by 808 days.

(21) Appl. No.: 17/291,099

(22) PCT Filed: Nov. 7, 2019

(86) PCT No.: PCT/JP2019/043626
§ 371 (c)(1),
(2) Date: Jun. 3, 2021

(87) PCT Pub. No.: WO2020/095983
PCT Pub. Date: May 14, 2020

(65) Prior Publication Data
US 2022/0017456 A1  Jan. 20, 2022

(30) Foreign Application Priority Data
Nov. 7, 2018 (JP) ................. 2018-209602

(51) Int. Cl.
C07C 269/04 (2006.01)
C07C 227/18 (2006.01)
C07C 269/06 (2006.01)
C07C 271/16 (2006.01)
C07C 271/22 (2006.01)
C07D 291/04 (2006.01)
C07D 291/06 (2006.01)
C07D 307/42 (2006.01)
C07D 333/16 (2006.01)

(52) U.S. Cl.
CPC .......... C07C 269/04 (2013.01); C07C 227/18 (2013.01); C07D 291/04 (2013.01); C07D 291/06 (2013.01); C07D 333/16 (2013.01)

(58) Field of Classification Search
CPC . C07C 269/04; C07C 227/18; C07C 2603/18; C07C 269/06; C07C 271/16; C07C 271/22; C07C 2523/44; C07C 229/22; C07D 291/04; C07D 291/06; C07D 333/16; C07D 307/42; C07B 2200/07; Y02P 20/55
See application file for complete search history.

(56) References Cited

U.S. PATENT DOCUMENTS

| 3,798,204 | A | 3/1974 | Nakajima et al. |
| 4,859,736 | A | 8/1989 | Rink |
| 5,057,415 | A | 10/1991 | Schuetz et al. |
| 5,059,679 | A | 10/1991 | Yajima et al. |
| 7,288,372 | B2 | 10/2007 | Olejnik et al. |
| 7,439,222 | B2 | 10/2008 | Guinn et al. |
| 8,518,666 | B2 | 8/2013 | Wang et al. |
| 8,809,280 | B2 | 8/2014 | Strom et al. |
| 9,133,245 | B2 | 9/2015 | Gao et al. |
| 9,409,952 | B2 | 8/2016 | Kariyuki et al. |
| 9,701,993 | B2 | 7/2017 | Suga et al. |
| 10,711,268 | B2 | 7/2020 | Murakami et al. |
| 10,815,489 | B2 | 10/2020 | Ohta et al. |
| 11,492,369 | B2 | 11/2022 | Nomura et al. |
| 11,542,299 | B2 | 1/2023 | Nomura et al. |
| 11,732,002 | B2 | 8/2023 | Iwasaki et al. |
| 11,787,836 | B2 | 10/2023 | Nomura et al. |
| 11,891,457 | B2 | 2/2024 | Kariyuki et al. |
| 12,071,396 | B2 | 8/2024 | Wadamoto |
| 2003/0219780 | A1 | 11/2003 | Olejnik et al. |
| 2005/0165217 | A1 | 7/2005 | Guinn et al. |
| 2008/0044854 | A1 | 2/2008 | Wang et al. |
| 2008/0221303 | A1 | 9/2008 | Katzhendler et al. |
| 2010/0137561 | A1 | 6/2010 | Chen |
| 2010/0292435 | A1 | 11/2010 | Chen et al. |
| 2012/0101257 | A1 | 4/2012 | Lubell et al. |
| 2013/0035296 | A1 | 2/2013 | Strom et al. |
| 2013/0217599 | A1 | 8/2013 | Suga et al. |
| 2014/0194369 | A1 | 7/2014 | Gao et al. |
| 2015/0080549 | A1 | 3/2015 | Kariyuki et al. |
| 2016/0272964 | A1 | 9/2016 | Murakami et al. |
| 2016/0311858 | A1 | 10/2016 | Kariyuki et al. |
| 2018/0127761 | A1 | 5/2018 | Ohta et al. |
| 2019/0338050 | A1 | 11/2019 | Nakano et al. |
| 2020/0040372 | A1 | 2/2020 | Tanaka et al. |
| 2020/0131669 | A1 | 4/2020 | Muraoka et al. |

(Continued)

FOREIGN PATENT DOCUMENTS

| CN | 101072760 A | 11/2007 |
| CN | 105829286 A | 8/2016 |

(Continued)

OTHER PUBLICATIONS

Afonso, A., et al., "Solid-Phase Synthesis of Biaryl Cyclic Peptides Containing a 3-Aryltyrosine," Eur J Org Chem., 31:6204-6211 (2012).
Alakhov, Y. B., et al., "Butylation of the Tryptophan Indole Ring: a Side Reaction During the Removal of t-Butyloxycarbonyl and t-Butyl Protecting Groups in Peptide Synthesis," J Chem Soc D., 7:406b-407 (1970).
Albericio, F., et al., "Fmoc Methodology: Cleavage from the Resin and Final Deprotection," Amino Acids, Peptides and Proteins in Organic Chemistry, 3:349-369 (2011).
Alex, A., et al., "Intramolecular hydrogen bonding to improve membrane permeability and absorption in beyond rule of five chemical space," Med Chem Commun., 2:669-674 (2011).
Alvaro, G., et al., "A Novel Activity of Immobilized Penicillin G Acylase: Removal of Benzyloxycarbonyl Amino Protecting Group," Biocatalysis and Biotransformation, 18(3):253-238 (2000).

(Continued)

Primary Examiner — Samantha L Shterengarts
Assistant Examiner — Sagar Patel
(74) Attorney, Agent, or Firm — Nixon & Vanderhye P.C.

(57) ABSTRACT

It was discovered that a cyclic sulfamidate can be produced by reacting an amino acid derivative with a cyclization reagent. In addition, it was discovered that an O-substituted serine derivative can be produced by reacting a cyclic sulfamidate with an alcohol.

16 Claims, No Drawings

(56) References Cited

U.S. PATENT DOCUMENTS

| | | |
|---|---|---|
| 2020/0277327 A1 | 9/2020 | Nomura et al. |
| 2020/0339623 A1 | 10/2020 | Nomura et al. |
| 2021/0061860 A1 | 3/2021 | Kariyuki et al. |
| 2021/0087572 A1 | 3/2021 | Ohta et al. |
| 2022/0024972 A1 | 1/2022 | Iwasaki et al. |
| 2022/0144762 A1 | 5/2022 | Wadamoto |
| 2022/0205009 A1 | 6/2022 | Shinohara et al. |
| 2022/0411462 A1 | 12/2022 | Hou et al. |
| 2023/0026641 A1 | 1/2023 | Nomura et al. |
| 2023/0056969 A1 | 2/2023 | Kondo et al. |
| 2023/0096766 A1 | 3/2023 | Muraoka et al. |
| 2023/0108274 A1 | 4/2023 | Kagotani et al. |
| 2023/0138226 A1 | 5/2023 | Nomura et al. |
| 2023/0151060 A1 | 5/2023 | Tanada et al. |
| 2023/0295221 A1 | 9/2023 | Iwasaki et al. |
| 2023/0303619 A1 | 9/2023 | Iwasaki et al. |
| 2023/0406879 A1 | 12/2023 | Nomura et al. |
| 2024/0052340 A1 | 2/2024 | Nishimura et al. |
| 2024/0067674 A1 | 2/2024 | Sekita et al. |
| 2024/0124517 A1 | 4/2024 | Morita et al. |
| 2024/0158446 A1 | 5/2024 | Kawada et al. |
| 2024/0166689 A1 | 5/2024 | Kariyuki et al. |

FOREIGN PATENT DOCUMENTS

| | | |
|---|---|---|
| EP | 1277755 A1 | 1/2003 |
| EP | 1424395 A1 | 6/2004 |
| EP | 1964916 A1 | 9/2008 |
| EP | 2088202 A1 | 8/2009 |
| EP | 2141175 A1 | 1/2010 |
| EP | 2177533 A1 | 4/2010 |
| EP | 2380596 A1 | 10/2011 |
| EP | 2492344 A1 | 8/2012 |
| EP | 2610348 A1 | 7/2013 |
| EP | 2615455 A1 | 7/2013 |
| EP | 2088202 B1 | 8/2013 |
| EP | 2647720 A1 | 10/2013 |
| EP | 2813512 A1 | 12/2014 |
| EP | 2492344 B1 | 4/2016 |
| EP | 3031915 A1 | 6/2016 |
| EP | 2141175 B1 | 7/2016 |
| EP | 3031915 B1 | 3/2019 |
| EP | 3563833 A1 | 11/2019 |
| EP | 2813512 B1 | 3/2021 |
| JP | S4935607 A | 4/1974 |
| JP | S57159747 A | 10/1982 |
| JP | S60169451 A | 9/1985 |
| JP | S62289 A | 1/1987 |
| JP | S62143698 A | 6/1987 |
| JP | S63260946 A | 10/1988 |
| JP | H01222795 A | 9/1989 |
| JP | H01250396 A | 10/1989 |
| JP | H0259146 B2 | 12/1990 |
| JP | H0681759 B2 | 10/1994 |
| JP | 2513775 B2 | 7/1996 |
| JP | 2001048866 A | 2/2001 |
| JP | 2001522862 A | 11/2001 |
| JP | 2003508408 A | 3/2003 |
| JP | 2003531199 A | 10/2003 |
| JP | 2005095013 A | 4/2005 |
| JP | 2007319064 A | 12/2007 |
| JP | 2008125396 A | 6/2008 |
| JP | 2009096791 A | 5/2009 |
| JP | 2009528824 A | 8/2009 |
| JP | 4490663 B2 | 6/2010 |
| JP | 4502293 B2 | 7/2010 |
| JP | 2011139667 A | 7/2011 |
| JP | 2012506909 A | 3/2012 |
| JP | 2012510486 A | 5/2012 |
| JP | 2012525348 A | 10/2012 |
| JP | 5200241 B2 | 6/2013 |
| JP | 5592893 B2 | 9/2014 |
| JP | 5808882 B2 | 11/2015 |
| JP | 2018509172 A | 4/2018 |
| WO | WO9214706 A1 | 9/1992 |
| WO | WO9831700 A1 | 7/1998 |
| WO | WO9924460 A2 | 5/1999 |
| WO | WO0181325 A2 | 11/2001 |
| WO | WO02085923 A2 | 10/2002 |
| WO | WO03014354 A1 | 2/2003 |
| WO | WO03068990 A1 | 8/2003 |
| WO | WO03089454 A2 | 10/2003 |
| WO | WO2005063791 A2 | 7/2005 |
| WO | WO2006061136 A2 | 6/2006 |
| WO | WO2007066627 A1 | 6/2007 |
| WO | WO2007103307 A2 | 9/2007 |
| WO | WO2007120614 A2 | 10/2007 |
| WO | WO2008117833 A1 | 10/2008 |
| WO | WO 2010053050 A1 | 5/2010 |
| WO | WO2010062590 A2 | 6/2010 |
| WO | WO2010063604 A1 | 6/2010 |
| WO | WO2010125079 A2 | 11/2010 |
| WO | WO2011049157 A1 | 4/2011 |
| WO | WO2011051692 A1 | 5/2011 |
| WO | WO2011058122 A1 | 5/2011 |
| WO | WO2012026566 A1 | 3/2012 |
| WO | WO2012033154 A1 | 3/2012 |
| WO | WO2012074130 A1 | 6/2012 |
| WO | WO2012122059 A1 | 9/2012 |
| WO | WO2013100132 A1 | 7/2013 |
| WO | WO2014033466 A1 | 3/2014 |
| WO | WO2014181888 A1 | 11/2014 |
| WO | WO2015019192 A2 | 2/2015 |
| WO | WO2015019999 A1 | 2/2015 |
| WO | WO2015092740 A2 | 6/2015 |
| WO | WO2015155676 A1 | 10/2015 |
| WO | WO2015179434 A1 | 11/2015 |
| WO | WO2015185162 A1 | 12/2015 |
| WO | WO2016115168 A1 | 7/2016 |
| WO | WO2016148044 A1 | 9/2016 |
| WO | WO2016154675 A1 | 10/2016 |
| WO | WO2017150732 A1 | 9/2017 |
| WO | WO2017181061 A1 | 10/2017 |
| WO | WO2018100561 A1 | 6/2018 |
| WO | WO2018124162 A1 | 7/2018 |
| WO | WO2018143145 A1 | 8/2018 |
| WO | WO2018225851 A1 | 12/2018 |
| WO | WO2018225864 A1 | 12/2018 |
| WO | WO2019117274 A1 | 6/2019 |
| WO | WO2020095983 A1 | 5/2020 |
| WO | WO2020111238 A1 | 6/2020 |
| WO | WO2020122182 A1 | 6/2020 |
| WO | WO2020138336 A1 | 7/2020 |
| WO | WO2020189540 A1 | 9/2020 |
| WO | WO2021090855 A1 | 5/2021 |
| WO | WO2021090856 A1 | 5/2021 |
| WO | WO2021132545 A1 | 7/2021 |
| WO | WO2021132546 A1 | 7/2021 |
| WO | WO2021246471 A1 | 12/2021 |
| WO | WO2021261577 A1 | 12/2021 |
| WO | WO2022138891 A1 | 6/2022 |
| WO | WO2022145444 A1 | 7/2022 |
| WO | WO2022234853 A1 | 11/2022 |
| WO | WO2023127869 A1 | 7/2023 |
| WO | WO2023214576 A1 | 11/2023 |

OTHER PUBLICATIONS

Bastiaans, H. M. M., et al., "Flexible and Convergent Total Synthesis of Cyclotheonamide B," J Org Chem., 62:3880-3889 (1997).

Beck, J. G., et al., "Intestinal Permeability of Cyclic Peptides: Common Key Backbone Motifs Identified," J Amer Chem Soc., 134(29):12125-12133 (2012).

Behrendt, R., et al., "Advances in Fmoc Solid-phase Peptide Synthesis," J Pep Sci., 22(1):4-27 (2016).

Bock, J. E., et al., "Getting in Shape: Controlling Peptide Bioactivity and Bioavailability Using Conformational Constraints," ACS Chem Biol., 8(3):488-499 (2013).

Bockus, A. T., et al., "Form and Function in Cyclic Peptide Natural Products: A Pharmacokinetic Perspective," Curr Top Med Chem., 13:821-836 (2013).

Brunner, J., et al., "Biosynthetic Incorporation of Non-natural Amino Acids Into Proteins," Chem Soc Rev., 22(3):183-189 (1993).

(56) References Cited

OTHER PUBLICATIONS

Carpino, L. A., et al., "Dramatically Enhanced N→O Acyl Migration During the Trifluoroacetic Acid-based Deprotection Step in Solid Phase Peptide Synthesis," Tetrahedron Letters, 46(8):1361-1364 (2005).
Chatterjee, J., et al., "N-methylation of Peptides: a New Perspective in Medicinal Chemistry," Accounts of Chemical Research, 41(10):1331-1342 (2008).
Chen, C. C., et al., "A Mild Removal of Fmoc Group Using Sodium Azide," Amino Acids, 46(2):367-374 (2014).
Chen, J. F., et al., "Effect of Alanine-293 Replacement on the Activity, ATP Binding, and Editing of *Escherichia coli* Leucyl-tRNA Synthetase," Biochemistry, 40(5):1144-1149 (2001).
Chen, S., et al., "Structurally Diverse Cyclisation Linkers Impose Different Backbone Conformations in Bicyclic Peptides," J Chem Biol., 13(7):1032-1038 (2012).
Cobb, S. L. and Vederas, J. C., "A concise stereoselective synthesis of orthogonally protected lanthionine and β-methyllanthionine," Org Biomol Chem. 5:1031-1038 (2007).
Cornella, J., et al., "Practical Ni-Catalyzed Aryl-Alkyl Cross-Coupling of Secondary Redox-Active Esters," J Amer Chem Soc., 138(7):2174-2177 (2016).
Cox, A. A., et al., "Drugging the Undruggable RAS: Mission Possible?," Nat Rev Drug Dis., 13(11):828-851 (2014).
Creighton, C. J., et al., "Mechanistic Studies of an Unusual Amide Bond Scission," J Amer Chem Soc., 121(29):6786-6791 (1999).
Cudic, M. and Fields, G. B., "Solid-Phase Peptide Synthesis," Molecular Biomethods Handbook, 515-546 (2008).
Cusack, S., et al., "The 2 a Crystal Structure of Leucyl-tRNA Synthetase and Its Complex With a Leucyl-adenylate Analogue," The EMBO Journal, 19(10):2351-2361 (2000).
Dailler, D., et al., "Divergent Synthesis of Aeruginosas Based on a C(sp(3)-H Activation Strategy," Chem Eur J., 21(26):9370-9379 (2015).
Dawson, P. E., et al., "Synthesis of Proteins by Native Chemical Ligation," Science, 266(5186):776-779 (1994).
Doi, Y., et al., "Elongation Factor Tu Mutants Expand Amino Acid Tolerance of Protein Biosynthesis System," J Amer Chem Soc., 129(46):14458-14462 (2007).
Doublie, S., et al., "Tryptophanyl-tRNA Synthetase Crystal Structure Reveals an Unexpected Homology to Tyrosyl-tRNA Synthetase," Structure, 3(1):17-31 (1995).
Eberhard, H., et al., "N--O-acyl Shift in Fmoc-based Synthesis of Phosphopeptides," Org Biomol Chem., 6(8):1349-1355 (2008).
Fang, W. J., et al., "Deletion of Ac-NMePhe(1) From [NMePhe(1)] Arodyn Under Acidic Conditions, Part 1: Effects of Cleavage Conditions and N-terminal Functionality," Biopolymers, 96(1):97-102 (2011).
Frankel, A., et al., "Encodamers: Unnatural Peptide Oligomers Encoded in RNA," Chemistry & Biology, 10(11):1043-1050 (2003).
Fujii, N., et al., "Trimethylsilyl Trifluoromethanesulphonate as a Useful Deprotecting Reagent in Both Solution and Solid Phase Peptide Syntheses," Journal of the Chemical Society, Chemical Communications, 4:274-275 (1987).
Fujino, M., et al., "Further Studies on the Use of Multi-substituted Benzenesulfonyl Groups for Protection of the Guanidino Function of Arginine," Chemical and Pharmaceutical Bulletin, 29(10):2825-2831 (1981).
Fujino, T., et al., "Reevaluation of the D-amino Acid Compatibility With the Elongation Event in Translation," Journal of the American Chemical Society, 135(5):1830-1837 (2013).
Fujino, T., et al., "Ribosomal Synthesis of Peptides with Multiple β-Amino Acids," Journal of the American Chemical Society, 138(6):1962-1969 (2016).
Fukai, S., et al., "Mechanism of Molecular Interactions for Trna(Val) Recognition by Valyl-trna Synthetase," RNA, 9(1):100-111 (2003).
Fukai, S., et al., "Structural Basis for Double-sieve Discrimination of L-valine From L-isoleucine and L-threonine by the Complex of Trna(Val) and Valyl-trna Synthetase," Cell, 103(5):793-803 (2000).
Fukunaga, R., et al., "Structural Basis for Non-cognate Amino Acid Discrimination by the Valyl-trna Synthetase Editing Domain," J Biol Chem., 280(33):29937-29945 (2005).
Ganesan, A., et al., "The Impact of Natural Products Upon Modern Drug Discovery," Current Opinion in Chemical Biology, 12(3):306-317 (2008).
GenBank, "Valine-tRNA ligase [Thermus thermophilus]," Accession No. P96142, accessed on Jan. 27, 2021.
Gilon, C., et al., "Backbone Cyclization: a New Method for Conferring Conformational Constraint on Peptides," Biopolymers, 31(6):745-750 (1991).
Goto, et al., "Ribosomal Synthesis of Combinatorial Polypeptides Containing Unusual Amino Acid Blocks," Kagaku Kogyo, 58(4):255-262 (2007).
Goto, Y., et al., "Flexizymes for Genetic Code Reprogramming," Nature Protocols, 6(6):779-790 (2011).
Goto, Y., et al., "Translation Initiation With Initiator Trna Charged With Exotic Peptides," J Amer Chem Soc., 131(14):5040-5041 (2009).
Grosjean, H. and Björk, G. R., "Enzymatic conversion of cytidine to lysidine in anticodon of bacterial tRNA$^{Ile}$—an alternative way of RNA editing," Trends Biochem Sci., 29(4):165-168 (2004).
Hartman, M. C. T., et al., "An Expanded Set of Amino Acid Analogs for the Ribosomal Translation of Unnatural Peptides," PLoS One, 2(10):e972 (2007).
Hartman, M. C. T., et al., "Enzymatic Aminoacylation of Trna With Unnatural Amino Acids," PNAS, 103(12):4356-4361 (2006).
Hayashi, G., et al., "Ribosomal Synthesis of Nonstandard Cyclic Peptides and Its Application to Drug Discovery," The Journal of Japanese Biochemical Society, 82(6):505-514 (2010).
Hecht, S. M., et al., "Chemical Aminoacylation of tRNA's," J Biol Chem., 253(13):4517-4520 (1978).
Heinis, C., et al., "Phage-encoded Combinatorial Chemical Libraries Based on Bicyclic Peptides," Nature Chemical Biology, 5(7):502-507 (2009).
Higuchi, T. and Suga, H., "Programmed Synthesis of Natural Product-Like Non-Standard Peptides Using the Translation System and Its Application," Journal of Synthetic Organic Chemistry, 68(3):217-227 (2010).
Hoogenboom, H. R., et al., "Selecting and Screening Recombinant Antibody Libraries," Nature Biotechnology, 23(9):1105-1116 (2005).
Hountondji, C., et al., "Crucial Role of Conserved Lysine 277 in the Fidelity of tRNA Aminoacylation by *Escherichia coli* Valyl-tRNA Synthetase," Biochemistry, 41(50):14856-14865 (2002).
Hountondji, C., et al., "Valyl-tRNA Synthetase From *Escherichia coli* MALDI-MS Identification of the Binding Sites for L-Valine or for Noncognate Amino Acids Upon Qualitative Comparative Labeling With Reactive Amino-Acid Analogs," European Journal of Biochemistry, 267(15):4789-4798 (2000).
Hruby, V. J., et al., "Emerging Approaches in the Molecular Design of Receptor-selective Peptide Ligands: Conformational, Topographical and Dynamic Considerations," The Biochemical Journal, 268(2):249-262 (1990).
Huihui, K. M. M., et al., "Decarboxylative Cross-Electrophile Coupling of N-Hydroxyphthalimide Esters with Aryl Iodides," J Am Chem Soc., 138(15):5016-5019 (2016).
Ikeuchi, Y., et al., "Agmatine-conjugated Cytidine in a tRNA Anticodon Is Essential for AUA Decoding in Archaea," Nature Chemical Biology, 6(4):277-282 (2010).
Ikeuchi, Y., et al., "Molecular Mechanism of Lysidine Synthesis that Determines tRNA Identity and Codon Recognition," Mol Cell, 19:235-246 (2005).
Isidro-Llobet, A., et al., "Amino Acid-protecting Groups," Chemical Reviews, 109(6):2455-2504 (2009).
Itoh, Y., et al., "Crystallographic and Mutational Studies of Seryl-trna Synthetase From the Archaeon Pyrococcus Horikoshii," RNA Biology, 5(3):169-177 (2008).
Iwane, Y., et al., "Expanding the amino acid repertoire of ribosomal polypeptide synthesis via the artificial division of codon boxes," Nat Chem., 8:317-325 (2016).

(56) References Cited

OTHER PUBLICATIONS

Jaradat, D. M. M., "Thirteen decades of peptide synthesis: key developments in solid phase peptide synthesis and amide bond formation utilized in peptide ligation," Amino Acids, 50:39-68 (2018).
Jones, A. B., et al., "A Formal Synthesis of FK-506. Exploration of Some Alternatives to Macrolactamization," J Org Chem., 55:2786-2797 (1990).
Josephson, K., et al., "mRNA Display: From Basic Principles to Macrocycle Drug Discovery," Drug Discovery Today, 19(4):388-399 (2014).
Josephson, K., et al., "Ribosomal Synthesis of Unnatural Peptides," J Amer Chem Soc., 127(33):11727-11735 (2005).
Kato, et al., Yakubutsutaishagaku, 2nd edition, 9-13 (2000).
Kato, et al., Yakubutsutaishagaku, 3rd edition, 43-46 (2010).
Katoh, T., et al., "Ribosomal Synthesis of Backbone Macrocyclic Peptides," Chemical Communications, 47(36):9946-9958 (2011).
Kawakami, T. and Aimoto, S., "Sequential Peptide Ligation by Using a Controlled Cysteinyl Prolyl Ester (CPE) Autoactivating Unit," Tetrahedron Letters, 48(11):1903-1905 (2007).
Kawakami, T., et al., "Diverse Backbone-cyclized Peptides via Codon Reprogramming," Nature Chemical Biology, 5(12):888-890 (2009).
Kawakami, T., et al., "In Vitro Selection of Multiple Libraries Created by Genetic Code Reprogramming to Discover Macrocyclic Peptides That Antagonize VEGFR2 Activity in Living Cells," ACS Chemical Biology, 8(6):1205-1214 (2013).
Kawakami, T., et al., "Incorporation of Electrically Charged N-alkyl Amino Acids Into Ribosomally Synthesized Peptides via Post-translational Conversion," Chemical Science, 5(3):887-893 (2014).
Kawakami, T., et al., "Messenger RNA-programmed Incorporation of Multiple N-methyl-amino Acids Into Linear and Cyclic Peptides," Chemistry & Biology, 15(1):32-42 (2008).
Kawakami, T., et al., "Ribosomal Synthesis of Polypeptoids and Peptoid-peptide Hybrids," J Amer Chem Soc., 130(50):16861-16863 (2008).
Kiho, T., et al., "Total Synthesis of Pleofugin A, a Potent Inositol Phosphorylceramide Synthase Inhibitor," Org Lett., 20:4637-4640 (2018).
Kleineweischede, R., et al., "Chemoselective Peptide Cyclization by Traceless Staudinger Ligation," Angewandte Chemie (International ed. in English), 47(32):5984-5988 (2008).
Kobayashi, T., et al., "Recognition of Non-alpha-amino Substrates by Pyrrolysyl-tRNA Synthetase," J Mol Biol., 385(5):1352-1360 (2009).
Kopina, B. J. and Lauhon, C. T., "Efficient Preparation of 2, 4-Diaminopyrimidine Nucleosides: Total Synthesis of Lysidine and Agmatidine," Org Lett., 14(16):4118-4121 (2012).
Kuhn, B., et al., "Intramolecular Hydrogen Bonding in Medicinal Chemistry," J Med Chem., 53:2601-2611 (2010).
Lajoie, M. J., et al., "Overcoming Challenges in Engineering the Genetic Code," J Mol Biol., 428:1004-1021 (2016).
Lassak, J., et al., "Stall No More at Polyproline Stretches With the Translation Elongation Factors EF-P and IF-5A," Molecular Microbiology, 99(2):219-235 (2016).
Laufer, B., et al., "The Impact of Amino Acid Side Chain Mutations in Conformational Design of Peptides and Proteins," Chemistry, 16(18):5385-5390 (2010).
Lee, K. W., et al., "Molecular Modeling Study of the Editing Active Site of Escherichia coli Leucyl-tRNA Synthetase: Two Amino Acid Binding Sites in the Editing Domain," Proteins, 54(4):693-704 (2004).
Lejeune, V., et al., "Towards a Selective Boc Deprotection on Acid Cleavable Wang Resin," Tetrahedron Letters, 44(25):4757-4759 (2003).
Lenzi, A., et al., "Synthesis of N-Boc-α-amino Acids With Nucleobase Residues as Building Blocks for the Preparation of Chiral PNA (Peptidic Nucleic Acids)," Tetrahedron Letters, 36(10):1713-1716 (1995).
Li, H., et al., "Ni-Catalyzed Electrochemical Decarboxylative C—C Couplings in Batch and Continuous Flow," Org Lett., 20:1338-1341 (2018).
Li, S., et al., "In Vitro Selection of Mrna Display Libraries Containing an Unnatural Amino Acid," J Amer Chem Soc., 124(34):9972-9973 (2002).
Li, X., et al., "Salicylaldehyde Ester-induced Chemoselective Peptide Ligations: Enabling Generation of Natural Peptidic Linkages at the Serine/threonine Sites," Org Lett., 12(8):1724-1727 (2010).
Liniger, M., et al., "Total Synthesis and Characterization of 7-Hypoquinuclidonium Tetrafluoroborate and 7-Hypoquinuclicone $BF_3$ Complex," J Am Chem Soc., 138:969-974 (2016).
Liu, D. R., et al., "Engineering a tRNA and Aminoacyl-tRNA Synthetase for the Site-specific Incorporation of Unnatural Amino Acids Into Proteins in Vivo," PNAS, 94(19):10092-10097 (1997).
Liu, Z., et al., "N-Boc Deprotection and Isolation Method for Water-soluble Zwitterionic Compounds," The Journal of Organic Chemistry, 79(23):11792-11796 (2014).
Lodder, M., et al., "The N-pentenoyl Protecting Group for Aminoacyl-tRNAs," Methods, 36(3):245-251 (2005).
Loos, P., et al., "Unified Azoline and Azole Syntheses by Optimized Aza-Wittig Chemistry," European Journal of Organic Chemistry, 2013(16):3290-3315 (2013).
Lundquist, K. Y., et al., "Improved Solid-phase Peptide Synthesis Method Utilizing Alpha-azide-protected Amino Acids," Org Lett., 3(5):781-783 (2001).
Luo, D., et al., "Total Synthesis of the Potent Marine-Derived Elatase Inhibitor Lyngbyastatin 7 and in Vitro Biological Evaluation in Model Systems for Pulmonary Disease," J Org Chem., 81:532-544 (2016).
Maini, R., et al., "Protein Synthesis with Ribosomes Selected for the Incorporation of β-Amino Acids," Biochemistry, 54(23):3694-3706 (2015).
Maini, R., et al., "Ribosome-mediated Synthesis of Natural Product-like Peptides via Cell-free Translation," Current Opinion in Chemical Biology, 34:44-52 (2016).
Malhotra, R., et al., "Efficient asymmetric synthesis of N-protected-β-aryloxyamino acids via regioselective ring opening of serine sulfamidate carboxylic acid," Org Biomol Chem., 12:6507 (2014).
Manfredini, S., et al., "Design and synthesis of phosphonoacetic acid (PPA) ester and amide bioisosters of ribofuranosylnucleoside diphosphates as potential ribonucleotide reductase inhibitors and evaluation of their enzyme inhibitory, cytostatic and antiviral activity," Antivir Chem Chemother., 14:183-194 (2003).
Marcucci, E., "Solid-Phase Synthesis of NMe-IB-01212, a Highly N-Methylated Cyclic Peptide," Org Lett., 14(2):612-615 (2012).
Mas-Moruno, C., et al., "Cilengitide: The First Anti-Angiogenic Small Molecule Drug Candidate Design, Synthesis, and Clinical Evaluation," Anti-Cancer Agents in Medicinal Chemistry, 10(10):753-768 (2010).
Meinnel, T., et al., "Methionine as Translation Start Signal: a Review of the Enzymes of the Pathway in Escherichia coli," Biochimie, 75(12):1061-1075 (1993).
Mermershtain, I., et al., "Idiosyncrasy and Identity in the Prokaryotic Phe-system: Crystal Structure of E. coli Phenylalanyl-tRNA Synthetase Complexed With Phenylalanine and AMP," Protein Science, 20(1):160-167 (2011).
Merryman, C. and Green, R., "Transformation of Aminoacyl tRNAs for the in Vitro Selection of "Drug-Like" Molecules," Chemistry & Biology, 11(4):575-582 (2004).
Millward, S. W., et al., "A General Route for Post-translational Cyclization of mRNA Display Libraries," J Amer Chem Soc., 127(41):14142-14143 (2005).
Millward, S. W., et al., "Design of Cyclic Peptides That Bind Protein Surfaces With Antibody-like Affinity," ACS Chemical Biology, 2(9):625-634 (2007).
Miyake, A., et al., "Design and Synthesis of N-[N-(S)-1-Ethoxycarbonyl-3-pheylpropyl]-L-alanyl]-N-(indan-2-yl)glycine (CV-3317), a New, Potent Angiotensin Converting Enzyme Inhibitor," Chem Pharm Bull., 34(7):2852-2858 (1986).
Montalbetti, C. A. G. N. and Falque, V., "Amide Bond Formation and Peptide Coupling," Tetrahedron, 61(46):10827-10852 (2005).

(56) References Cited

OTHER PUBLICATIONS

Muramatsu, T., et al., "A Novel Lysine-substituted Nucleoside in the First Position of the Anticodon of Minor Isoleucine tRNA from *Escherichia coli*," J Biol Chem., 263(19):9261-9267 (1988).
Murashige, R., et al., "Asymmetric and Efficient Synthesis of Homophenylalanine Derivatives via Friedel-Crafts Reaction With Trifluoromethanesulfonic Acid," Tetrahedron Letters, 49(46):6566-6568 (2008).
Niida, A., et al., "Investigation of the Structural Requirements of K-ras(G12d) Selective Inhibitory Peptide Krpep-2d Using Alanine Scans and Cysteine Bridging," Bioorganic & Medicinal Chemistry Letters, 27(12):2757-2761 (2017).
Ohta, A., et al., "Synthesis of Polyester by Means of Genetic Code Reprogramming," Chemistry & Biology, 14(12):1315-1322 (2007).
Ohtsuki, T., et al., "Phototriggered Protein Syntheses by Using (7-diethylaminocoumarin-4-yl) Methoxycarbonyl-Caged Aminoacyl tRNAs," Nature Communications, 7:12501 (2016).
Ohwada, T., et al., "On the Planarity of Amide Nitrogen. Intrinsic Pyramidal Nitrogen of N-acyl-7-azabicyclo[2.2.1]heptanes," Tetrahedron Letters, 39(8):865-868 (1998).
Orain, D., et al., "Protecting Groups in Solid-Phase Organic Synthesis," J Comb Chem., 4(1):1-16 (2002).
Osawa, T., et al., "Structural basis of tRNA agmatinylation essential for AUA codon decoding," Nat Struct Mol Biol., 18(11):1275-1280 (2011).
Ostrem, J. M. L. and Shokat, K. M., "Direct small-molecule inhibitors of KRAS: from structural insights to mechanism-based design," Nat Rev Drug Discov., 15:771-785 (2016).
Ovadia, O., et al., "Improvement of Drug-Like Properties of Peptides: The Somatostatin Paradigm," Expert Opinion on Drug Discovery, 5(7):655-671 (2010).
Parthasarathy, R., et al., "Sortase a as a Novel Molecular "Stapler" for Sequence-specific Protein Conjugation," Bioconjugate Chemistry, 18(2):469-476 (2007).
Peacock, J. R., et al., "Amino Acid-dependent Stability of the Acyl Linkage in Aminoacyl-tRNA," RNA, 20(6):758-764 (2014).
Perona, J. J., et al., "Structural Diversity and Protein Engineering of the Aminoacyl-tRNA Synthetases," Biochemistry, 51(44):8705-29 (2012).
Peschke, B., et al., "New highly potent dipeptidic growth hormone secretagogues with low molecular weight," Eur J Med Chem., 35:599-618 (2000).
Piszkiewicz, D., et al., "Anomalous Cleavage of Aspartyl-proline Peptide Bonds During Amino Acid Sequence Determination," Biochemical and Biophysical Research Communications, 40(5):1173-1178 (1970).
Räder, A. F. B., et al., "Orally Active Peptides: Is There a Magic Bullet?," Angew Chem Int Ed., 57:14414-14438 (2018).
Rafi, S. B., et al., "Predicting and Improving the Membrane Permeability of Peptidic Small Molecules," J Med Chem., 55:3163-3169 (2012).
Reddy, P. R., et al., "Synthesis of Small Cyclic Peptides via Intramolecular Heck Reactions," Tetrahedron Letters, 44(2):353-356 (2003).
Rezai, T., et al., "Testing the Conformational Hypothesis of Passive Membrane Permeability Using Synthetic Cyclic Peptide Diastereomers," J Amer Chem Soc., 128(8):2510-2511 (2006).
Rodriguez, H., et al., "A Convenient Microwave-Enhanced Solid-phase Synthesis of Short Chain N-Methyl-Rich Peptides," Journal of Peptide Science, 16(3):136-140 (2010).
Roodbeen, R., et al., "Microwave Heating in the Solid-Phase Synthesis of N-Methylated Peptides: When Is Room Temperature Better?," European Journal of Organic Chemistry, 2012(36):7106-7111 (2012).
Sakamoto, K., et al., "K-Ras(G12D)-selective inhibitory peptides generated by random peptide T7 phage display technology," Biochem Biophys Res Commun., 484:605-611 (2017).
Salowe, S. P., et al., "The Catalytic Flexibility of tRNA$^{Ile}$-lysidine Synthetase Can Generate Alternative tRNA Substrates for Isoleucyl-tRNA Synthetase," J Biol Chem., 284(15):9656-9662 (2009).
Samatar, A. A. and Poulikakos, P. I., "Targeting RAS-ERK signaling in cancer: promises and challenges," Nat Rev Drug Discov., 13:928-942 (2014).
Sang-Aroon, W. and Ruangpornvisuti, V., "Theoretical study on isomerization and peptide bond cleavage at aspartic residue," J Mol Model, 19:3627-3636 (2013).
Sankaranarayanan, R., et al., "The Structure of Threonyl-tRNA Synthetase-tRNA(Thr) Complex Enlightens Its Repressor Activity and Reveals an Essential Zinc Ion in the Active Site," Cell, 97(3):371-381 (1999).
Satyanarayanajois, S. D. and Hill, R. A., "Medicinal Chemistry for 2020," Future Medicinal Chemistry, 3(14):1765-1786 (2011).
Schlippe, Y. V. G., et al., "In Vitro Selection of Highly Modified Cyclic Peptides That Act as Tight Binding Inhibitors," J Amer Chem Soc., 134(25):10469-10477 (2012).
Sever, S., et al., "*Escherichia coli* Tryptophanyl-tRNA Synthetase Mutants Selected for Tryptophan Auxotrophy Implicate the Dimer Interface in Optimizing Amino Acid Binding," Biochemistry, 35(1):32-40 (1996).
Shimizu, Y., et al., "Cell-free translation reconstituted with purified components," Nat Biotechnol., 19(8):751-755 (2001).
Shukla, G. S. and Krag, D. N., "Phage-Displayed Combinatorial Peptide Libraries in Fusion to Beta-Lactamase as Reporter for an Accelerated Clone Screening: Potential Uses of Selected Enzyme-Linked Affinity Reagents in Downstream Applications," Combinatorial Chemistry & High Throughput Screening, 13(1):75-87 (2010).
Sogabe, S., et al., "Crystal Structure of a Human K-Ras G12D Mutant in Complex with GDP and the Cyclic Inhibitory Peptide KRpep-2D," ACS Med Chem Lett., 8:732-736 (2017).
Starosta, A.L., et al., "A Conserved Proline Triplet in Val-tRNA Synthetase and the Origin of Elongation Factor P," Cell Reports, 9(2):476-483 (2014).
Stetsenko, D. A., et al., "Removal of Acid-Labile Protecting or Anchoring Groups in the Presence of Polyfluorinated Alcohol: Application to Solid-Phase Peptide Synthesis, " Russian Journal of Bioorganic Chemistry, 42(2):143-152 (2016).
Struck, A.-W., et al., "An Enzyme Cascade for Selective Modification of Tyrosine Residues in Structurally Diverse Peptides and Proteins," J Am Chem Soc., 138:3038-3045 (2016).
Subtelny, A. O., et al., "Optimal Codon Choice Can Improve the Efficiency and Fidelity of N-methyl Amino Acid Incorporation Into Peptides by in-vitro Translation," Angewandte Chemie (International ed. English), 50(14):3164-3167 (2011).
Subtelny, A. O., et al., "Ribosomal Synthesis of N-methyl Peptides," J Amer Chem Soc., 130(19):6131-6136 (2008).
Suenaga, K., et al., "Aurilide, a cytotoxic depsipeptide from the sea hare *Dolabella auricularia*: isolation, structure determination, synthesis, and biological activity," Tetrahedron, 60:8509-8527 (2004).
Suenaga, K., et al., "Synthesis and cytotoxicity of aurilide analogs," Bioorg Med Chem Lett., 18:3902-3905 (2008).
Suzuki, T. and Miyauchi, K., "Discovery and characterization of tRNA$^{Ile}$ lysidine synthetase (TilS)," FEBS Lett., 584:272-277 (2010).
Suzuki, "The Genetic Code Deciphering Mechanism in Archaea," Kagaku to Seibutsu, 50(1):36-43 (2012).
Tam, J.P., et al., "Cyclohexyl Ester as a New Protecting Group for Aspartyl Peptides to Minimize Aspartimide Formation in Acidic and Basic Treatments," Tetrahedron Letters, 20(42):4033-4036 (1979).
Tan, Z., et al., "Amino Acid Backbone Specificity of the *Escherichia coli* Translation Machinery," J Amer Chem Soc., 126(40):12752-12753 (2004).
Teixido, M., et al., "Solid-phase Synthesis and Characterization of N-methyl-rich Peptides," The Journal of Peptide Research, 65(2):153-166 (2005).
Terasaka, et al., "Construction of Nonstandard Peptide Library by Genetic Code Reprogramming and Bioactive Peptide Discovery," Experimental Medicine, 29(7):1063-70 (2011).
Terasaka, N., et al., "Recent Developments of Engineered Translational Machineries for the Incorporation of Non-canonical Amino Acids Into Polypeptides," International Journal of Molecular Sciences, 20;16(3):6513-6531 (2015).
Toriyama, F., et al., "Redox-Active Esters in Fe-Catalyzed C—C Coupling," J Am Chem Soc., 138(35):11132-11135 (2016).

(56) References Cited

OTHER PUBLICATIONS

Tsuda, et al., "Amino Acids, Peptides and Proteins in Organic Chemistry," 3:201-406, 495-517, 549-569 (2011).
Tsukiji, S. and Nagamune, T., "Sortase-mediated Ligation: A Gift From Gram-positive Bacteria to Protein Engineering," Chembiochem, 10(5):787-798 (2009).
Urban, J., et al., "Lability of N-alkylated Peptides Towards TFA Cleavage," International Journal of Peptide and Protein Research, 47(3):182-189 (1996).
Vaisar, T. and Urban, J., "Gas-phase Fragmentation of Protonated Mono-N-methylated Peptides. Analogy with Solution-phase Acid-catalyzed Hydrolysis," J Mass Spectrometry, 33:505-524 (1998).
Van Der Auwera, C. and Anteunis, M. J. O., "Easy cleavage of C'-terminal iminoacids from peptide acids through acidic hydrolysis," Int J Peptide Protein Res., 31:186-191 (1988).
Wang, J., et al., "Kinetics of Ribosome-Catalyzed Polymerization Using Artificial Aminoacyl-tRNA Substrates Clarifies Inefficiencies and Improvements," ACS Chemical Biology, 10(10):2187-2192 (2015).
Wang, S., et al., "Iridium/f-Amphox-Catalyzed Asymmetric Hydrogenation of Styrylglyoxylamides," Synlett., 29(16):2203-2207 (2018).
Wang, T. and Danishefsky, S. J., "Revisiting Oxytocin through the Medium of Isonitriles," J Am Chem Soc., 134:13244-13247 (2012).
Watanabe, E., et al., "A Practical Method for Continuous Production of sp3-Rich Compounds from (Hetero)Aryl Halides and Redox-Active Esters," Chemistry, 26(1):186-191 (2020).
Weber, F., et al., "A potato mitochondrial isoleucine tRNA is coded for by a mitochondrial gene possessing a methionine anticodon," Nucleic Acid Res., 18(17):5027-5030 (1990).
Wells, J. A. and McClendon, C. L., "Reaching for High-Hanging Fruit in Drug Discovery at Protein-Protein Interfaces," Nature, 450(7172):1001-1009 (2007).
Wenschuh, H., et al., "Stepwise Automated Solid Phase Synthesis of Naturally Occurring Peptaibols Using FMOC Amino Acid Fluorides," The Journal of Organic Chemistry, 60(2):405-410 (1995).
Wermuth, C. G., editor, "The Practice of Medicinal Chemistry," $2^{nd}$ Edition, 52-53, 87-88 (2003).
White, C.J. and Yudin, A.K., "Contemporary Strategies for Peptide Macrocyclization," Nature Chemistry, 3(7):509-524 (2011).
White, T. R., et al., "On-resin N-methylation of Cyclic Peptides for Discovery of Orally Bioavailable Scaffolds," Nature Chemical Biology, 7(11):810-817 (2011).
Wu, J. and Lebrilla, C. B., "Intrinsic Basicity of Oligomeric Peptides that Contain Glycine, Alanine, and Valine—The Effects of the Alkyl Side Chain on Proton Transfer Reactions," J Am Soc Mass Spectrom. 6:91-101 (1995).
Wu, N., et al., "A genetically encoded photocaged amino acid," J Amer Chem Soc., 126(44):14306-14307 (2004).
Yajima, H., et al., "New Strategy for the Chemical Synthesis of Proteins," Tetrahedron, 44(3):805-819 (1988).
Yamagishi, Y., et al., "Natural Product-like Macrocyclic N-methyl-peptide Inhibitors Against a Ubiquitin Ligase Uncovered From a Ribosome-expressed De Novo Library," Chemistry & Biology, 18(12):1562-1570 (2011).
Yamanoi, K. and Ohfune, Y., "Synthesis of Trans- and Cis-α-(Carboxycyclopropyl)Glycines. Novel Neuroinhibitory Amino Acids as L-Glutamate Analogue," Tetrahedron Lett., 29(10):1181-1184 (1988).
Yanagisawa, T., et al., "Multistep Engineering of Pyrrolysyl-tRNA Synthetase to Genetically Encode N(Epsilon)-(O-azidobenzyloxycarbonyl) Lysine for Site-specific Protein Modification," Chemistry & Biology, 15(11):1187-97 (2008).
Yang, Y., "Side Reactions in Peptide Synthesis," 1-31 (2015).
Yang, Y., "Side Reactions in Peptide Synthesis," 246 (2016).
Yao, G., et al., "Efficient Synthesis and Stereochemical Revision of Coibamide A," J Am Chem Soc., 137:13488-13491 (2015).
Zhai, Y. and Martinis, S. A., "Two Conserved Threonines Collaborate in the *Escherichia coli* Leucyl-tRNA Synthetase Amino Acid Editing Mechanism," Biochemistry, 44(47):15437-15443 (2005).
Zhang, A. J., et al., "A Method for Removal of N-BOC Protecting Groups from Substrates on TFA-Sensitive Resins," Tetrahedron Letters, 39(41):7439-7442 (1998).
Zhang, B., et al., "Specificity of Translation for N-alkyl Amino Acids," Journal of the American Chemical Society, 129(37):11316-11317 (2007).
Zhang, K., et al., "Ab Initio Studies of Neutral and Protonated Triglycines: Comparison of Calculated and Experimental Gas-Phase Basicity," Journal of the American Chemical Society, 116(25):11512-11521 (1994).
U.S. Appl. No. 07/251,176, filed Sep. 30, 1988, Schuetz, et al.
U.S. Appl. No. 10/345,664, filed Jan. 16, 2003, Olejnik et al.
U.S. Appl. No. 11/682,272, filed Mar. 5, 2007, Wang et al.
U.S. Appl. No. 13/505,625, filed Oct. 22, 2012, Strom et al.
U.S. Appl. No. 13/816,911, filed Feb. 13, 2013, Suga et al.
U.S. Appl. No. 14/125,906, filed Mar. 10, 2014, Gao et al.
U.S. Appl. No. 14/368,564, filed Jun. 25, 2014, Kariyuki et al., related application.
U.S. Appl. No. 14/889,868, filed Mar. 7, 2016, Murakami et al.
U.S. Appl. No. 15/166,550, filed May 27, 2016, Kariyuki et al., related application.
U.S. Appl. No. 15/557,532, filed Sep. 12, 2017, Ohta et al., related application.
U.S. Appl. No. 16/081,522, filed Jul. 8, 2019, Nakano et al., related application.
U.S. Appl. No. 16/479,736, filed Jul. 22, 2019, Tanaka et al., related application.
U.S. Appl. No. 16/619,014, filed Dec. 3, 2019, Muraoka et al., related application.
U.S. Appl. No. 16/619,388, filed Dec. 4, 2019, Nomura et al., related application.
U.S. Appl. No. 16/771,335, filed Jun. 10, 2020, Nomura et al., related application.
U.S. Appl. No. 17/011,815, filed Sep. 3, 2020, Kariyuki et al., related application.
U.S. Appl. No. 17/024,944, filed Sep. 18, 2020, Ohta et al., related application.
U.S. Appl. No. 17/297,231, filed May 26, 2021, Iwasaki et al., related application.
U.S. Appl. No. 17/312,296, filed Jun. 9, 2021, Muraoka et al., related application.
U.S. Appl. No. 17/417,822, filed Jun. 24, 2021, Shinohara et al., related application.
U.S. Appl. No. 17/437,535, filed Sep. 9, 2021, Wadamoto et al., related application.
U.S. Appl. No. 17/738,283, filed May 6, 2022, Hou et al., related application.
U.S. Appl. No. 17/773,733, filed May 2, 2022, Tanada et al., related application.
U.S. Appl. No. 17/773,734, filed May 2, 2022, Nomura et al., related application.
U.S. Appl. No. 17/787,809, filed Jun. 21, 2022, Kagotani et al., related application.
U.S. Appl. No. 17/788,506, filed Jun. 23, 2022, Kondo et al., related application.
U.S. Appl. No. 17/928,759, filed Nov. 30, 2022, Iwasaki et al., related application.
U.S. Appl. No. 17/976,942, filed Oct. 31, 2022, Nomura et al., related application.
U.S. Appl. No. 18/010,608, filed Dec. 15, 2022, Nishimura et al., related application.
U.S. Appl. No. 18/203,371, filed May 30, 2023, Iwasaki et al., related application.
U.S. Appl. No. 18/268,737, filed Jun. 21, 2023, Morita et al., related application.
U.S. Appl. No. 18/269,334, filed Jun. 23, 2023, Sekita et al., related application.
U.S. Appl. No. 18/289,592, filed Nov. 6, 2023, Kawada et al., related application.
U.S. Appl. No. 18/459,998, filed Sep. 1, 2023, Nomura et al., related application.
U.S. Appl. No. 18/460,300, filed Sep. 1, 2023, Kariyuki et al., related application.

(56) References Cited

OTHER PUBLICATIONS

Bolek, S. and Ignatowska, J., "Ring opening reactions of cyclic sulfamidates. Synthesis of β-fluoroaryl alanines and derivatives of 4,4-difluoroglutamic acid," J Fluorine Chem., 217:13-21 (2019).

Burkholder, T. P., et al., "Acid-Catalyzed O-Allylation of β-Hydroxy-α-Amino Acids: An Entry Into Conformationally Constrained Dipeptide Surrogates," Bioorganic & Medicinal Chemistry Letters, 2(6):579-582 (1992).

Gracia, S. R., et al., "Synthesis of chemically modified bioactive peptides: recent advances, challenges and developments for medicinal chemistry," Future Med Chem., 1(7):1289-1310 (2009).

Gravestock, D., et al., "Novel branched isocyanides as useful building blocks in the Passerini-amine deprotection-acyl migration (PADAM) synthesis of potential HIV-1 protease inhibitors," Tetrahedron Letters, 53:3225-3229 (2012).

Malhotra, R., et al., "Efficient asymmetric synthesis of N-protected-β-aryloxyamino acids via regioselective ring opening of serine sulfamidate carboxylic acid," Org Biomol Chem., 12:6507-6515 (2014).

Mangold, S. L., et al., "Z-Selective Olefin Metathesis on Peptides: Investigation of Side-Chain Influence, Preorganization, and Guidelines in Substrate Selection," J Am Chem., 136:12469-12478 (2014).

Morieux, P., et al., "The Structure-Activity Relationship of the 3-Oxy Site in the Anticonvulsant (R)-N-Benzyl 2-Acetamido-3-methoxypropionamide," J Med Chem., 53:5716-5726 (2010).

Navo, C. D., et al., "Oxygen by Carbon Replacement at the Glycosidic Linkage Modulates the Sugar Conformation in Tn Antigen Mimics," ACS Omega, 3:18142-18152 (2018).

U.S. Appl. No. 18/723,993, filed Jun. 25, 2024, Komiya et al., related application.

U.S. Appl. No. 18/773,066, filed Jul. 15, 2024, Tanada et al., related application.

U.S. Appl. No. 18/781,112, filed Jul. 23, 2024, Wadamoto, related application.

U.S. Appl. No. 18/829,566, filed Sep. 10, 2024, Kawada et al., related application.

CAS Registry No. 1508128-17-3, et al., STN Database, Dec. 31, 2013, 2 pages.

CAS Registry No. 1689875-13-5, et al., STN Database, Apr. 23, 2015, 13 pages.

O-SUBSTITUTED SERINE DERIVATIVE PRODUCTION METHOD

CROSS-REFERENCE TO RELATED APPLICATIONS

This application is a U.S. National Phase of PCT Application No. PCT/JP2019/043626, filed Nov. 7, 2019, which claims the benefit of Japanese Patent Application No. 2018-209602, filed Nov. 7, 2018, each of which is incorporated herein by reference in its entirety.

TECHNICAL FIELD

The present invention relates to O-substituted serine derivatives useful as pharmaceutical intermediates and cyclic sulfamidates useful for producing them, and methods for producing those compounds.

BACKGROUND ART

Regarding access to tough targets represented by the inhibition of protein-protein interactions, middle molecule compounds (molecular weight of 500-2,000) may be superior to small molecule compounds. Middle molecule compounds may also be superior to antibodies in that they can be internalized into cells. Among the bioactive middle molecule compounds, peptide pharmaceuticals are valuable molecular species, and more than 40 types are already in the market (Non-Patent Literature (NPL) 1). Representative examples of peptide pharmaceuticals include cyclosporin A and polymyxin B. By focusing on their structures, it can be understood that they are peptide compounds comprising some unnatural amino acids. Unnatural amino acids refer to amino acids that are not coded on mRNAs in nature, and it is very interesting that naturally occurring cyclosporin A and polymyxin B contain unnatural amino acids, and that these unnatural structural sites interact with sites of action in a living body to develop pharmacological activities. As an example of the interaction between an unnatural amino acid and a site of action in a living body, the study of the interaction between O-substituted serine on lacosamide and sodium channel (NPL 2) is known.

Among the methods for producing O-substituted serine derivatives, the following methods are known as methods for producing O-alkyl substituted serine derivatives.

1. The method for producing O-alkyl substituted serine derivatives from serine and alkyl halide in the presence of a base using Williamson ether synthesis, or the modified method thereof (NPL 3).
2. The synthetic method for producing O-alkyl substituted serine derivatives from serine and trichloroacetimidate in the presence of an acid catalyst by applying Schmidt Glycosylation (NPL 4).
3. The synthetic method for producing O-alkyl substituted serine derivatives from serine and allyl carbonate ester in the presence of a palladium catalyst (NPL 5).

The above are methods in which an alkyl group is directly incorporated into serine.

4. The synthetic method for producing O-alkyl substituted serine derivatives in which an aziridine compound derived from serine is reacted with an alcohol in the presence of a Lewis acid or a Broensted acid catalyst (Patent Literature (PTL) 1, 2).
5. The method for producing O-alkyl substituted serine derivatives in which a cyclic sulfamidate derived from serine is reacted with an alcohol in the presence of a base (NPL 6).

The above are methods for producing O-alkyl substituted serine derivatives via an intermediate derived from serine.

CITATION LIST

Patent Literature

[PTL 1] Japanese Patent Application Kokai Publication No. (JP-A): S57-159747 (unexamined, published Japanese patent application)
[PTL 2] WO 2010/053050

Non-Patent Literature

[NPL 1] Future Med. Chem. 2009, 1, 1289-1310
[NPL 2] J. Med. Chem., 2010, 53(15), 5716-5726
[NPL 3] Tetrahedron Letters, 2012, 53, 3225-3229
[NPL 4] Bioorganic & Medicinal Chemistry Letters, 1992, 2, 579-582
[NPL 5] Journal of the American Chemical Society, 2014, 136, 12469-12478
[NPL 6] Organic and Biomolecular Chemistry, 2014, 12, 6507-6515

SUMMARY OF INVENTION

Technical Problem

The method using an aziridine derived from serine described in PTL 1 and 2 has a problem regarding the regioselectivity of the reactive site.

The method using an aziridine derived from serine described in NPL 2 has a problem regarding the regioselectivity of the reactive site.

In the method performed in the presence of a base described in NPL 3, it is known that the hydroxyl group in serine is eliminated, and the method is limited to the production of a highly reactive benzyl ether.

In the method of production from trichloroacetimidate described in NPL 4, the substituent on the oxygen in the producible O-substituted serine derivative is limited to an allyl group.

In the method based on the coupling reaction of an allyl ether described in NPL 5, the substituent on the oxygen in the producible O-substituted serine derivative is limited to an allyl group.

In the method using a sulfamidate derived from serine described in NPL 6, the O-substituted serine derivative that is producible in high yield is limited only to those substituted with an aromatic ring such as phenol, and only one case has been reported regarding synthesis of O-alkyl substituted serine derivative obtained by the reaction with an alkyl alcohol where the yield was only 16%. That is, synthetic examples of O-alkyl substituted serine derivatives that achieved satisfactory regioselectivity, yield, and optical purity by reacting cyclic sulfamidate with alcohol are extremely limited.

The objective of the present invention is to provide methods for producing O-substituted serine derivatives useful as pharmaceutical intermediates and sulfamidates useful for producing them with satisfactory regioselectivity, chemical yield, and optical purity.

Solution to Problem

The present inventors dedicatedly investigated the reaction of a cyclic sulfamidate derived from an amino acid derivative with an alcohol, and as a result, discovered methods for producing O-substituted serine derivative (I) with excellent regioselectivity and chemical yield, while keeping high optical purity, using the following Scheme 1 or Scheme 2, and completed the present invention.

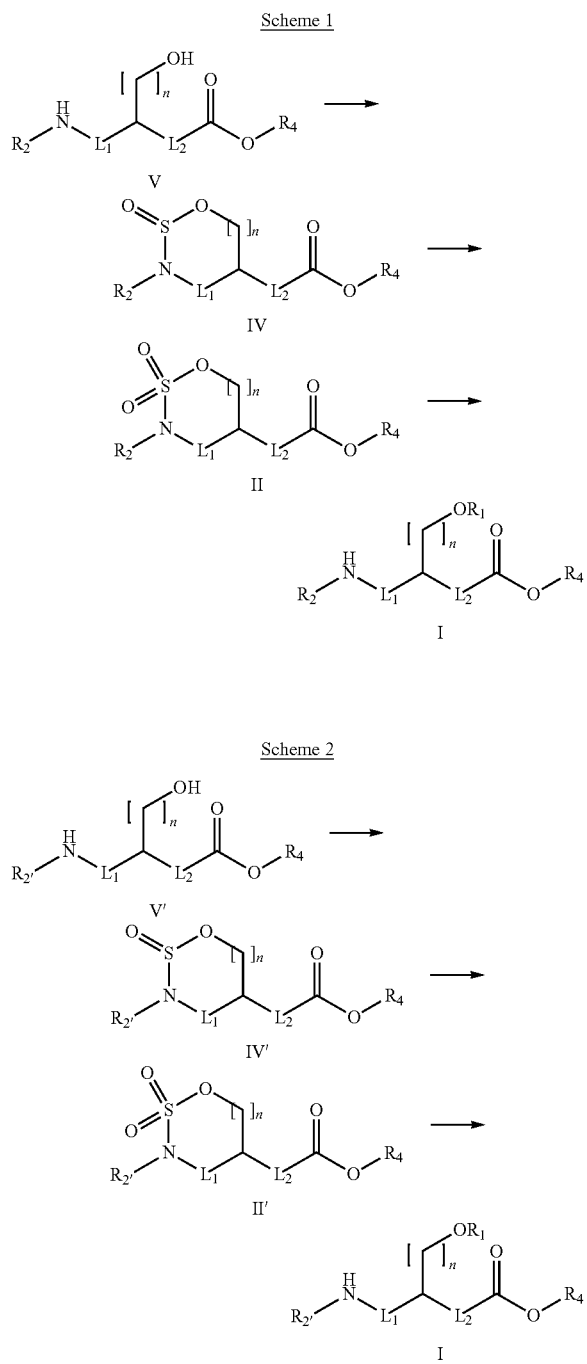

In one non-limiting and specific embodiment, the present invention comprises the following.

[1] A method for producing a compound represented by general formula (I):

(I)

[wherein,
R1 is optionally substituted C1-C6 alkyl, optionally substituted C3-C8 cycloalkyl, optionally substituted aralkyl, or optionally substituted heteroaralkyl,
R2 is C1-C6 alkyl or an amino protecting group,
R4 is a carboxyl protecting group,
L1 is a single bond or —CH2-,
L2 is a single bond or —CH2-, and
n is 1 or 2,
with the proviso that when L1 is —CH2-, L2 is a single bond, and when L2 is —CH2-,
L1 is a single bond],
its chemically acceptable salt, or a solvate thereof,
the method comprising the following steps:
Step A: reacting a compound represented by general formula (V):

(V)

(V)

[wherein, $R_2$, $R_4$, $L_1$, $L_2$, and n are synonymous with those described above],
its chemically acceptable salt, or a solvate thereof with a cyclization reagent to obtain
a compound represented by general formula (IV):

(IV)

[wherein, R2, R4, L1, L2, and n are synonymous with those described above],
its chemically acceptable salt, or a solvate thereof,
Step B: reacting the compound represented by general formula (IV), its chemically acceptable salt, or a solvate thereof with an oxidizing agent to obtain a compound represented by general formula (II):

(II)

[wherein, R2, R4, L1, L2, and n are synonymous with those described above],
its chemically acceptable salt, or a solvate thereof, and Step C: reacting the compound represented by general formula (II), its chemically acceptable salt, or a solvate thereof with R1OH (wherein, R1 is synonymous with those described above) to obtain the compound represented by general formula (I), its chemically acceptable salt, or a solvate thereof.

[2] A method for producing a compound represented by general formula (I):

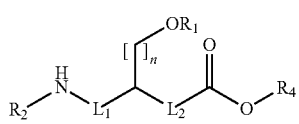
(I)

[wherein,
$R_1$ is optionally substituted $C_1$-$C_6$ alkyl, optionally substituted $C_3$-$C_8$ cycloalkyl, optionally substituted aralkyl, or optionally substituted heteroaralkyl,
$R_2$ is a hydrogen,
$R_4$ is a carboxyl protecting group,
$L_1$ is a single bond or —$CH_2$—,
$L_2$ is a single bond or —$CH_2$—, and
n is 1 or 2,
with the proviso that when $L_1$ is —$CH_2$—, $L_2$ is a single bond, and when $L_2$ is —$CH_2$—, $L_1$ is a single bond],
its chemically acceptable salt, or a solvate thereof,
the method comprising the following steps:

Step A: reacting a compound represented by general formula (V'):

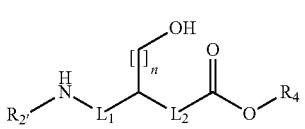
(V')

[wherein, R2' is an amino protecting group, and R4, L1, L2, and n are synonymous with those described above],
its chemically acceptable salt, or a solvate thereof with a cyclization reagent to obtain a compound represented by general formula (IV'):

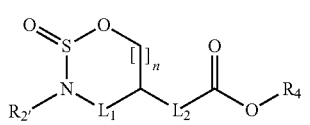
(IV')

[wherein, R2', R4, L1, L2, and n are synonymous with those described above],
its chemically acceptable salt, or a solvate thereof, Step B: reacting the compound represented by general formula (IV'), its chemically acceptable salt, or a solvate thereof with an oxidizing agent to obtain a compound represented by general formula (II'):

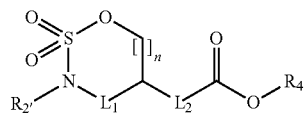
(II')

[wherein, R2', R4, L1, L2, and n are synonymous with those described above],
its chemically acceptable salt, or a solvate thereof, and Step C: reacting the compound represented by general formula (II'), its chemically acceptable salt, or a solvate thereof with R1OH (wherein, R1 is synonymous with that described above) to obtain the compound represented by general formula (I), its chemically acceptable salt, or a solvate thereof.

[3] The method of [1] or [2], further comprising a step (Step D) of deprotecting the carboxyl protecting group represented by R4 of the compound represented by general formula (I), its chemically acceptable salt, or a solvate thereof to obtain a compound represented by general formula (I'):

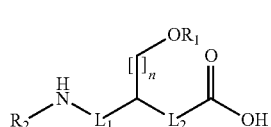
(I')

[wherein, R1, R2, L1, L2, and n are synonymous with those in [1] or [2]],
its chemically acceptable salt, or a solvate thereof.

[4] The method of [3], further comprising a step (Step E) of introducing a group represented by R3 to the amino group of the compound represented by general formula (I'), its chemically acceptable salt, or a solvate thereof to obtain a compound represented by general formula (I"):

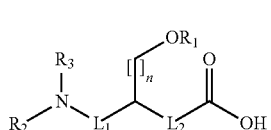
(I")

[wherein, R1, R2, L1, L2, and n are synonymous with those in [1] or [2], and R3 is an amino protecting group or C1-C4 alkyl],
its chemically acceptable salt, or a solvate thereof.

[5] The method of [1], [3], or [4], wherein
R1 is C1-C6 alkyl, C3-C8 cycloalkyl, aralkyl, or heteroaralkyl, which is optionally substituted with one or more substituents independently selected from halogen, aryl that is optionally substituted with halogen, or hydroxyl,
R2 is selected from Boc, Fmoc, Cbz, or Alloc, and
R4 is benzyl or tert-Bu.

[6] The method of any one of [2] to [4], wherein
R1 is C1-C6 alkyl, C3-C8 cycloalkyl, aralkyl, or heteroaralkyl, which is optionally substituted with one or more substituents independently selected from halogen, aryl that is optionally substituted with halogen, or hydroxyl,
R2' is selected from Boc, Fmoc, Cbz, or Alloc, and
R4 is benzyl or tert-Bu.

[7] The method of [4], wherein R3 is selected from Boc, Fmoc, Cbz, Alloc, or methyl.
[8] The method of any one of [1] to [7], wherein the cyclization reagent used in Step A is thionyl chloride.
[9] The method of any one of [1] to [8], wherein the oxidizing agent used in Step B is a combination of periodate and ruthenium catalyst.
[10] The method of [9], wherein periodate that is 1.5 to 5 equivalents and ruthenium catalyst that is 0.01 to 0.2 equivalents to the compound represented by general formula (IV), its chemically acceptable salt, or a solvate thereof, or to the compound represented by general formula (IV'), its chemically acceptable salt, or a solvate thereof, are used.
[11] The method of any one of [1] to [10], wherein Step B is performed in a solvent mixture of acetonitrile and water.
[12] The method of any one of [1] to [11], wherein Step C is performed in the presence of an acid salt.
[13] The method of [12], wherein the acid salt is NaH2PO4, KH2PO4, or CsH2PO4.
[14] The method of [13], wherein NaH2PO4, KH2PO4, or CsH2PO4 that is 2 to 5 equivalents to the compound represented by general formula (II), its chemically acceptable salt, or a solvate thereof, or to the compound represented by general formula (II'), its chemically acceptable salt, or a solvate thereof, are used.
[15] The method of any one of [1] to [14], wherein Step C is performed in 2,2,2-trifluoroethanol, 1,1,1,3,3,3-hexafluoro-2-propanol, or 2-methyltetrahydrofuran.
[16] The method of any one of [1] to [15], wherein Step C is performed at a temperature from −20° C. to about the boiling point of the solvent used in the step.
[17] The method of any one of [1] to [16], wherein Step C further comprises a step of extracting the reaction mixture with an organic solvent, and the extract is used in Step D without concentration to dryness.
[18] The method of any one of [3] to [17], wherein Step D is performed in the presence of a Pd catalyst.
[19] The method of [18], wherein Step D is performed in the presence of hydrogen gas, formic acid, or ammonium formate.
[20] The method of any one of [1] to [19], wherein Step A is performed in ethyl acetate, isopropyl acetate, or butyl acetate, and thionyl chloride that is 1.5 to 5 equivalents to the compound represented by general formula (V), its chemically acceptable salt, or a solvate thereof, or to the compound represented by general formula (V'), its chemically acceptable salt, or a solvate thereof is used.
[21] The method of [20], wherein Step A is performed at a temperature from −30° C. to 0° C.

Effects of the Invention

According to the present invention, unnatural amino acids useful for exploring peptide pharmaceuticals, and/or for supplying active ingredients of pharmaceuticals can be provided with high regioselectivity, chemical yield, and optical purity.

DESCRIPTION OF EMBODIMENTS

Abbreviations used herein are shown below:
AcOEt: ethyl acetate
Alloc group: allyloxycarbonyl group
t-Bu group: tert-butyl group
Boc group: tert-butoxycarbonyl group
Cbz group: benzyloxycarbonyl group
DIPEA: N,N-diisopropylethylamine
DMA: N,N-dimethylacetamide
DME: 1,2-dimethoxyethane
DMF: N,N-dimethylformamide
DMSO: dimethylsulfoxide
EtOH: ethanol
Fmoc group: 9-fluorenylmethyloxycarbonyl group
MeCN: acetonitrile
NMP: N-methylpyrrolidone
TEA: triethylamine
TFE: 2,2,2-trifluoroethanol
THF: tetrahydrofuran As used herein, "alkyl" means a monovalent group induced by removing an arbitrary hydrogen atom from an aliphatic hydrocarbon, which does not contain hetero atoms (atoms other than carbon and hydrogen atoms) or unsaturated carbon-carbon bonds, and which has a subset of hydrocarbyl or hydrocarbon group structure containing hydrogen and carbon atoms. The alkyl groups include straight-chain or branched-chain groups. The alkyl groups include alkyl groups of 1 to 20 carbon atoms ($C_1$-$C_{20}$, and herein below, "$C_p$-$C_q$" means that the number of carbon atoms is from p to q), preferably $C_1$-$C_6$ alkyl groups. The alkyl groups specifically include methyl, ethyl, propyl, butyl, pentyl, hexyl, isopropyl, tert-butyl group, and sec-butyl group.

As used herein, "cycloalkyl" means a saturated or partially saturated cyclic monovalent aliphatic hydrocarbon group, and includes monocyclic, bicyclic, and spirocyclic ring. Preferable examples include $C_3$-$C_8$ cycloalkyl. The cycloalkyl group may be partially unsaturated. The cycloalkyls specifically include, for example, cyclopropyl, cyclobutyl, cyclopentyl, and cyclohexyl.

As used herein, "aryl" means a monovalent aromatic hydrocarbon ring, and preferably includes $C_6$-$C_{10}$ aryl. The aryls specifically include, for example, phenyl and naphthyl (e.g., 1-naphthyl and 2-naphthyl).

As used herein, "heteroaryl" means a group of a monovalent aromatic ring containing preferably 1 to 4 hetero atoms among those which compose the ring (also referred to as "in the ring" herein), and may be partially saturated. The ring may be a monocyclic ring, or a fused ring of two (e.g., bicyclic heteroaryl fused with benzene or monocyclic heteroaryl). The number of atoms which compose the ring is preferably from 5 to 10 (5 to 10 membered heteroaryl). The heteroaryls specifically include, for example, furyl, thienyl, pyrrolyl, imidazolyl, pyrazolyl, thiazolyl, pyridyl, pyrimidyl, pyridazinyl, pyrazinyl, benzofuranyl, benzothienyl, quinolyl, isoquinolyl, quinazolinyl, and quinoxalinyl.

As used herein, "arylalkyl (aralkyl)" means a group containing both an aryl and an alkyl, that is for example a group in which at least one hydrogen atom in the alkyl is replaced with an aryl, and preferably includes "$C_6$-$C_{10}$ aryl-$C_1$-$C_6$ alkyl". The arylalkyl groups specifically include, for example, benzyl and phenethyl.

As used herein, "heteroarylalkyl (heteroaralkyl)" means a group containing both a heteroaryl and an alkyl, that is for example a group in which at least one hydrogen atom in the alkyl is replaced with a heteroaryl, and preferably includes "5 to 10 membered heteroaryl-$C_1$-$C_6$ alkyl". The heteroarylalkyls specifically include, for example, pyridylmethyl, thienylmethyl, and furanylmethyl.

As used herein, "alkylene" means a bivalent group induced by further removing an arbitrary hydrogen atom from the "alkyl", and preferably the alkylene includes $C_1$-$C_6$ alkylene. Such alkylenes specifically include, for example, methylene, 1,2-ethylene, 1,1-ethylene, 1,3-propylene, tetramethylene, pentamethylene, and hexamethylene.

As used herein, "phosphate salt" means a salt in which the negative ion is a phosphate ion ($PO_4^{3-}$) or a hydrogen phosphate ion ($H_2PO_4^-$ or $HPO_4^{2-}$), and the positive ion is a metal ion. The metal ion is selected from alkaline metal ions or alkaline earth metal ions, and is preferably an alkaline metal ion, preferably a sodium, potassium, or cesium ion. The phosphate salts preferably include disodium hydrogen phosphate anhydride, dipotassium hydrogen phosphate anhydride, or dicesium hydrogen phosphate anhydride, and hydrates thereof.

As used herein, "acid salt" means a salt that yields hydrogen ions when dissolved in a solvent, and includes sodium dihydrogen phosphate anhydride ($NaH_2PO_4$), potassium dihydrogen phosphate anhydride ($KH_2PO_4$), cesium dihydrogen phosphate anhydride ($CsH_2PO_4$), disodium hydrogen phosphate anhydride, dipotassium hydrogen phosphate anhydride, dicesium hydrogen phosphate anhydride, sodium hydrogen sulfate anhydride, potassium hydrogen sulfate anhydride, cesium hydrogen sulfate anhydride, and hydrates thereof.

In the production methods described below, if the group defined herein undergoes an undesired chemical conversion under the conditions of the methods of implementation, production of the compounds of the present invention can be performed using techniques such as protection and deprotection of functional groups. Selection of protecting groups and deprotection procedures include, for example, the methods described in "Greene's, "Protective Groups in Organic Synthesis" (fifth edition, John Wiley & Sons 2014)", which may be appropriately used according to the reaction conditions. The order of the reaction steps such as the introduction of the substituents can be changed as needed. For example, protecting groups of an amino group include Fmoc, Boc, Cbz, or Alloc groups. These carbamate groups can be introduced by reacting amino groups with a carbamating agent in the presence of a base catalyst. Carbamating agents include, for example, $Boc_2O$, BocOPh, FmocOSu, FmocCl, CbzCl, and AllocCl. Base catalysts include, for example, lithium carbonate, sodium carbonate, sodium hydrogen carbonate, potassium carbonate, potassium hydrogen carbonate, cesium carbonate, cesium hydrogen carbonate, lithium hydroxide, sodium hydroxide, potassium hydroxide, cesium hydroxide, sodium phosphate, potassium phosphate, N-methylmorpholine, triethylamine, diisopropylethylamine, and N,N-dimethylaminopyridine. Carbamate groups, which are amino protecting groups, can be removed under basic conditions, under acidic conditions, or under hydrolysis conditions.

Protecting groups a carboxyl group include alkyl and benzyl groups. The protecting groups such as alkyl and benzyl groups can be removed by hydrolysis reaction under basic or acidic conditions, or hydrolysis reaction in the presence of a transition metal catalyst and the like.

The compounds of the present invention represented by each formula may be their chemically acceptable salts, or chemically acceptable solvates thereof. Chemically acceptable salts of the compound represented by each formula include, for example, hydrochloride; hydrobromide; hydroiodide; phosphate; phosphonate; sulfate; sulfonate such as methanesulfonate and p-toluenesulfonate; carboxylate such as acetate, citrate, malate, tartrate, succinate, and salicylate; or alkaline metal salt such as sodium salt and potassium salt; alkaline earth metal salt such as magnesium salt and calcium salt; ammonium salt such as ammonium salt, alkyl ammonium salt, dialkyl ammonium salt, trialkyl ammonium salt, and tetraalkyl ammonium salt. These salts can be produced by contacting the compounds with an acid or a base usable in the production of pharmaceuticals. Chemically acceptable solvates of the compounds of the present invention represented by each formula imply a phenomenon in which a solute molecule strongly attracts a solvent molecule in a solution to form a molecular group, and the term hydrates is used when the solvent is water. Solvates of the compounds of the present invention include solvates not only with a single solvent such as water, alcohol (e.g., methanol, ethanol, 1-propanol, and 2-propanol), and dimethylformamide, but also with multiple solvents.

"Amino acids" herein include natural amino acids and unnatural amino acids (amino acid derivatives). The compounds of the present invention may be amino acids, preferably amino acid derivatives. "Natural amino acids" herein refer to Gly, Ala, Ser, Thr, Val, Leu, Ile, Phe, Tyr, Trp, His, Glu, Asp, Gln, Asn, Cys, Met, Lys, Arg, and Pro. Unnatural amino acids include, but not limited to, N-alkyl-amino acids, β-amino acids, γ-amino acids, D-amino acids, N-substituted serine, α,α-disubstituted serine, amino acids with side chains different from those in natural amino acids, and O-substituted serine. There is no limitation on the selection of a substituent attached to the amino acid backbone (referred to as a side chain of the amino acid) and may be freely selected from, for example, alkyl, aryl, heteroaryl, aralkyl, heteroaralkyl, or cycloalkyl groups, in addition to a hydrogen atom, and 1 or 2 methylene groups in these substituents that are not directly attached to the amino acid backbone are optionally substituted with atoms or groups selected from the group consisting of an oxygen atom, a nitrogen atom, a carbonyl group (—CO—), and a sulfonyl group (—$SO_2$—), each of which is optionally substituted with any substituents, and the substituents are also not limited. Examples include optionally substituted alkyl, aryl, heteroaryl, aralkyl, heteroaralkyl, cycloalkyl, or alkoxyalkyl groups (e.g., methoxymethyl group). Also, the amino acids herein may be compounds having carboxy and amino groups in the same molecule. The amino acids in the present specification may have any configuration.

An amino group in the amino acid backbone may be unsubstituted ($NH_2$), or optionally substituted. A carboxyl group in the amino acid backbone may be unsubstituted ($CO_2H$), or optionally substituted. "Amino acids" herein include all isotopic compounds corresponding to each one. Isotopic compounds of "amino acids" are those in which at least one atom is replaced with an atom that has the same atomic number (proton number) and different mass number (sum of numbers of proton and neutron). Examples of the isotopes included in the "amino acids" herein are a hydrogen, carbon, nitrogen, oxygen, phosphorus, sulfur, fluorine, and chlorine atom, and include $^2H$, $^3H$, $^{13}C$, $^{14}C$, $^{17}O$, $^{18}O$, $^{32}P$, $^{35}S$, $^{18}F$, and $^{36}Cl$, respectively.

As used herein, "halogen atom" means a fluorine, chlorine, bromine, and an iodine atom.

In the present specification, when a halogen atom is a substituent of an aromatic carbocyclic ring, an aromatic heterocyclic ring, or the like, a preferable halogen atom includes a fluorine or chlorine atom. Specific examples include 2-fluorophenyl group, 3-fluorophenyl group, 4-fluorophenyl group, 2-chlorophenyl group, 3-chlorophenyl group, 4-chlorophenyl group, 5-fluoro-2-pyridyl group, or 5-fluoro-3-pyridyl group.

In the present specification, when a halogen atom is a substituent of an alkyl or alkoxy group, a preferable halogen atom includes a fluorine atom. Specific examples include trifluoromethyl group, 2,2,2-trifluoroethyl group, pentafluoroethyl group, 2,2,3,3-tetrafluoropropyl group, heptafluoropropyl group, trifluoromethoxy group, 2,2,2-trifluoroethoxy group, pentafluoroethoxy group, 2,2,3,3-tetrafluoropropoxy group, or heptafluoropropoxy group.

As used herein, "having a hetero atom in a ring" means to contain a hetero atom among the atoms which compose the ring, and such groups include heteroaryl groups such as pyridyl group or thienyl group, piperidyl group, and morpholino group. When the hetero atom is an oxygen atom, it is referred to as "having an oxygen atom in a ring" or the like.

In the present specification, an "oxidizing agent" is used for a reaction in which a sulfur atom in a ring of a cyclic sulfamidite is oxidized from a sulfoxide to a sulfone to yield a cyclic sulfamidate, and examples include hydrogen peroxide, organic peroxide, persulfate, halogen oxide, or a combination of halogen oxide and transition metal catalyst. Preferably, examples include 3-chloroperbenzoic acid, oxone, and a combination of periodate and ruthenium catalyst. Periodate includes sodium periodate or potassium periodate. Ruthenium catalyst includes ruthenium trichloride anhydride or ruthenium trichloride hydrate.

One embodiment of the present invention is to provide unnatural amino acids useful for exploring peptide pharmaceuticals. Another embodiment of the present invention is to provide methods for producing high quality unnatural amino acids for supplying active ingredients of pharmaceuticals.

(General Production Method)

General production methods of the compounds of the present invention are explained.

In a certain aspect, the compound represented by formula (I) can be produced according, for example, to Production Method 1 comprising Step C (ring-opening addition reaction) shown below.

Production Method 1:

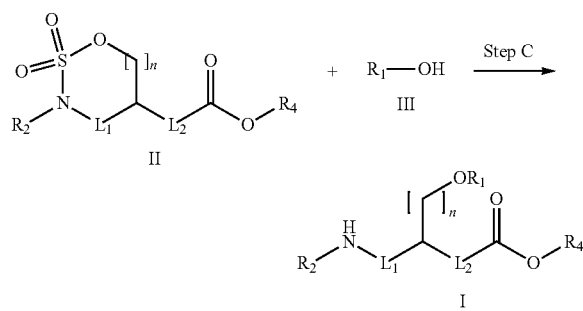

$R_1$ in the formula above is optionally substituted $C_1$-$C_6$ alkyl, optionally substituted $C_3$-$C_5$ cycloalkyl, optionally substituted aralkyl, or optionally substituted heteroaralkyl. $R_1$ is preferably $C_1$-$C_6$ alkyl, $C_3$-$C_8$ cycloalkyl, aralkyl, or heteroaralkyl, which is optionally substituted with one or more substituents independently selected from halogen, aryl (the aryl is optionally substituted with halogen or the like), or hydroxyl. $R_1$ specifically includes, for example, methyl, ethyl, i-propyl, n-propyl, n-butyl, i-pentyl, 3,3,3-trifluoro-2-hydroxypropyl, 2,2,3,3-tetrafluoropropyl, 2-hydroxypropyl, 2-hydroxy-2-methyl-propyl, 3-hydroxy-3-methyl-butyl, cyclopropyl, benzyl, fluorobenzyl, thienylmethyl, and furanylmethyl.

$R_2$ in the formula above is $C_1$-$C_6$ alkyl or a protecting group of an amino group. Such $R_2$ includes, for example, methyl, ethyl, benzyl, Fmoc, Boc, Cbz, or Alloc group.

$R_4$ in the formula above is a protecting group of a carboxyl group. Such $R_4$ includes, for example, alkyl such as t-butyl, and trityl, cumyl, allyl, and benzyl.

$L_1$ in the formula above is a single bond or —$CH_2$—, and $L_2$ is a single bond or —$CH_2$—. Herein, when $L_1$ is —$CH_2$—, $L_2$ is a single bond, and when $L_2$ is —$CH_2$—, $L_1$ is a single bond. Namely, a combination of $L_1$ and $L_2$ specifically includes the following three: (i) $L_1$=a single bond and $L_2$=a single bond; (ii) $L_1$=—$CH_2$— and $L_2$=a single bond; and (iii) $L_1$=a single bond and $L_2$=—$CH_2$—.

In the formula above, n represents the number of methylene group, and n is 1 or 2.

Step C (ring-opening addition reaction) in Production Method 1 is a step in which $R_1$ is introduced by a nucleophilic substitution reaction of cyclic sulfamidate derivative (II) with alcohol derivative (III) to produce O-substituted serine derivative (I). This step can be performed by stirring the reaction mixture for 1 to 48 hours in the presence or absence of a dissolution aid solvent, in the presence or absence of an acid salt, and at a temperature from −20° C. to about the boiling point of the solvent, preferably from 0° C. to 180° C.

As the alcohol derivative (III) represented by $R_1$—OH, any alcohol derivative having $R_1$ defined above can be used. Non-limiting examples of such alcohol derivative include methanol, ethanol, 1-propanol, 2-propanol, 1-butanol, 3-methylbutanol, 3,3,3-trifluoropropane-1,2-diol, 2,2,3,3-tetrafluoropropylalcohol, 2-hydroxypropylalcohol, 2-methylpropane-1,2-diol, 3-hydroxy-3-methyl-butylalcohol, cyclopropylalcohol, benzylalcohol, 3-fluorobenzylalcohol, 2-thiophenemethanol, and 2-furfurylalcohol.

Dissolution aid solvents include, for example, halogenated solvent such as 2,2,2-trifluoroethanol, 1,1,1,3,3,3-hexafluoro-2-propanol, dichloromethane, and chloroform, ether type solvent such as diethyl ether, tetrahydrofuran, 2-methyltetrahydrofuran, dioxane, methyl tert-butyl ether, cyclopentyl methyl ether, and dimethoxyethane, benzene type solvent such as toluene and benzotrifluoride, ester type solvent such as ethyl acetate, isopropyl acetate, and butyl acetate, ketone type solvent such as acetone and methyl ethyl ketone, among which 2,2,2-trifluoroethanol, 1,1,1,3,3,3-hexafluoro-2-propanol, or 2-methyltetrahydrofuran is used preferably.

Acid salts include, for example, sodium dihydrogen phosphate anhydride ($NaH_2PO_4$), potassium dihydrogen phosphate anhydride ($KH_2PO_4$), cesium dihydrogen phosphate anhydride ($CsH_2PO_4$), disodium hydrogen phosphate anhydride, dipotassium hydrogen phosphate anhydride, dicesium hydrogen phosphate anhydride, sodium hydrogen sulfate anhydride, potassium hydrogen sulfate anhydride, cesium hydrogen sulfate anhydride, and hydrates thereof, among which $NaH_2PO_4$, $KH_2PO_4$, or $CsH_2PO_4$ is preferable. Preferably, these acid salt are used at 2 to 5 equivalents to the starting material. By using acid salts, the objective compounds can be obtained efficiently.

Step C can further comprise a step of extracting the reaction mixture with an organic solvent, and the extract can be used in the next step without concentration to dryness.

In a certain aspect, the compound of the present invention represented by formula (I) above can be produced according, for example, to Production Method 2 comprising Step C (ring-opening addition reaction) shown below.

Production Method 2:

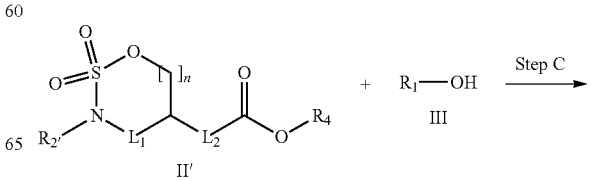

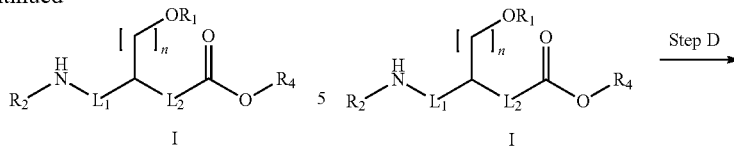

$R_1$ in the formula above is optionally substituted $C_1$-$C_6$ alkyl, optionally substituted $C_3$-$C_8$ cycloalkyl, optionally substituted aralkyl, or optionally substituted heteroaralkyl. $R_1$ is preferably $C_1$-$C_6$ alkyl, $C_3$-$C_8$ cycloalkyl, aralkyl, or heteroaralkyl, which is optionally substituted with one or more substituents independently selected from halogen, aryl (the aryl is optionally substituted with halogen or the like), or hydroxyl. $R_1$ specifically includes, for example, methyl, ethyl, i-propyl, n-propyl, n-butyl, i-pentyl, 3,3,3-trifluoro-2-hydroxypropyl, 2,2,3,3-tetrafluoropropyl, 2-hydroxypropyl, 2-hydroxy-2-methyl-propyl, 3-hydroxy-3-methyl-butyl, cyclopropyl, benzyl, fluorobenzyl, thienylmethyl, and furanylmethyl.

$R_2$ in the formula above is a hydrogen.

$R_{2'}$ in the formula above is a protecting group of an amino group. Such $R_{2'}$ includes, for example, Fmoc, Boc, Cbz, or Alloc group.

$R_4$ in the formula above is a protecting group of a carboxyl group. Such $R_4$ includes, for example, alkyl such as t-butyl, and trityl, cumyl, allyl, and benzyl.

$L_1$ in the formula above is a single bond or —$CH_2$—, and $L_2$ is a single bond or —$CH_2$—. Herein, when $L_1$ is —$CH_2$—, $L_2$ is a single bond, and when $L_2$ is —$CH_2$—, $L_1$ is a single bond. Namely, a combination of $L_1$ and $L_2$ specifically includes the following three: (i) $L_1$=a single bond and $L_2$=a single bond; (ii) $L_1$=—$CH_2$— and $L_2$=a single bond; and (iii) $L_1$=a single bond and $L2$=—$CH_2$—.

In the formula above, n represents the number of methylene group, and n is 1 or 2.

Step C (ring-opening addition reaction) in Production Method 2 is a step in which $R_1$ is introduced by a nucleophilic substitution reaction of cyclic sulfamidate derivative (II') with alcohol derivative (III), and $R_{2'}$ is removed to produce O-substituted serine derivative (I) having a free amino group. This reaction can be performed by stirring the reaction mixture for 1 to 48 hours in the presence or absence of a dissolution aid solvent, in the presence or absence of an acid salt, and at a temperature from –20° C. to about the boiling point of the solvent, preferably from 0° C. to 180° C.

As alcohol derivative (III) represented by $R_1$—OH, any alcohol derivative having $R_1$ defined above can be used. Non-limiting examples of such alcohol derivative include methanol, ethanol, 1-propanol, 2-propanol, 1-butanol, 3-methylbutanol, 3,3,3-trifluoropropane-1,2-diol, 2,2,3,3-tetrafluoropropylalcohol, 2-hydroxypropylalcohol, 2-methylpropane-1,2-diol, 3-hydroxy-3-methyl-butylalcohol, cyclopropylalcohol, benzylalcohol, 3-fluorobenzylalcohol, 2-thiophenemethanol, and 2-furfurylalcohol.

The same dissolution aid solvents as in Step C in Production Method 1 can be used.

The same acid salts as in Step C in Production Method 1 can be used.

Step C can further comprise a step of extracting the reaction mixture with an organic solvent, and the extract can be used in the next step without concentration to dryness.

The compound of formula (I) obtained via Step C can further be subjected to Step D (deprotection reaction) shown below, and this step is also comprised in Production Method 1 or Production Method 2.

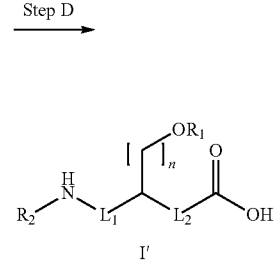

$R_1$, $R_2$, $R_4$, $L_1$, $L_2$, and n in the formula above are synonymous with $R_1$, $R_2$, $R_4$, $L_1$, $L_2$, and n in Production Method 1 and Production Method 2, respectively.

This step is a step in which the carboxyl protecting group of O-substituted serine derivative of formula (I) ($R_4$) is deprotected to produce O-substituted serine derivative (I'). This reaction can be performed by stirring the reaction mixture for 1 to 24 hours in the presence or absence of a metal catalyst, preferably a Pd catalyst, or an acid catalyst, in the presence or absence of a hydrogen source, and at a temperature from 0° C. to about the boiling point of the solvent.

Metal catalysts include, for example, those in which metal catalyst is carried on a solid support represented by active carbon, such as palladium on carbon and palladium hydroxide on carbon, and palladium oxide, platinum oxide, Raney nickel, tetrakis(triphenylphosphine) palladium, bis(triphenylphosphine) palladium dichloride, tris(dibenzylideneacetone) dipalladium, and palladium acetate.

Acid catalysts include, for example, hydrochloric acid, hydrobromic acid, trifluoromethanesulfonic acid, and sulfuric acid.

Hydrogen sources include hydrogen gas, formic acid, or ammonium formate.

The reaction can be performed in a solvent such as ethyl acetate, isopropyl acetate, butyl acetate, methanol, and ethanol.

The compound of formula (I') obtained via Step D can further be subjected to Step E ($R_3$-introduction reaction) shown below, and this step is also comprised in Production Method 1 or Production Method 2.

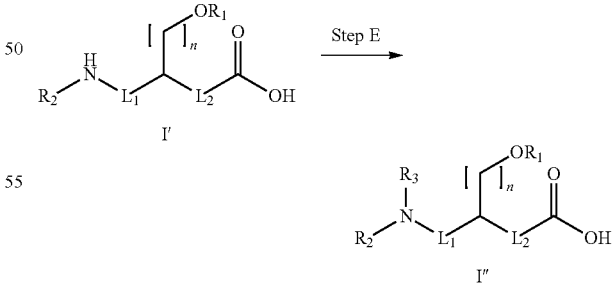

$R_1$, $R_2$, $L_1$, $L_2$, and n in the formula above are synonymous with $R_1$, $R_2$, $L_1$, $L_2$, and n in Production Method 1 and Production Method 2, respectively.

$R_3$ in the formula above is an amino protecting group or $C_1$-$C_4$ alkyl. Amino protecting groups preferably include Boc group, Fmoc group, Cbz group, or Alloc group, and $C_1$-$C_4$ alkyl is preferably methyl, ethyl, or propyl.

The introduction of a protecting group (R3) to the amino group can be performed by reacting the α-amino group portion of O-substituted serine derivative (I') with a carbamating agent. This reaction can be performed by stirring the reaction mixture for 1 to 24 hours in the presence or absence of a base catalyst, and at a temperature from −10° C. to about the boiling point of the solvent.

Carbamating agents include, for example, Boc2O, BocOPh, FmocOSu, FmocCl, CbzCl, and AllocCl.

Base catalysts include, for example, lithium carbonate, sodium carbonate, sodium hydrogen carbonate, potassium carbonate, potassium hydrogen carbonate, cesium carbonate, cesium hydrogen carbonate, lithium hydroxide, sodium hydroxide, potassium hydroxide, cesium hydroxide, sodium phosphate, potassium phosphate, N-methylmorpholine, triethylamine, diisopropylethylamine, and N,N-dimethylamino pyridine.

As a solvent, acetonitrile, DMF, NMP, or the like can preferably be used.

The introduction of an alkyl group (R3) to the amino group can be performed using the method of Freidinger et al. (U.S. Pat. No. 4,535,167), in which the α-amino group portion of O-substituted serine derivative (I') is reacted with alkylaldehyde in a solvent in the presence of an acid catalyst to form oxazolidinone ring, and then reductive ring-opening is carried out using trialkylsilane in the presence of an acid. These reactions can be performed by stirring the reaction mixture for 1 to 24 hours at a reaction temperature from 0° C. to about the boiling point of the solvent.

Regarding the step of forming an oxazolidinone ring, alkylaldehydes include formaldehyde, acetaldehyde, propanal, butanal, and 2-methylpropanal, trialkylsilanes include triethylsilane, acid catalysts include 4-toluenesulfonic acid and camphorsulfonic acid, and solvents include toluene and THF. Regarding the reductive ring-opening step, acids include trifluoroacetic acid.

The introduction of an alkyl group (R3) to the amino group can also be performed using the method of Shimokawa et al. (Bioorg. Med. Chem. Lett., 2009, 19(1), 92-95) or Prashad et al. (Org. Lett., 2003, 5(2), 125-128), in which an amino acid with a protected N-terminal is reacted with an alkylating agent in an organic solvent in the presence of a base to yield N-alkyl amino acid. This reaction can be performed by stirring the reaction mixture for 1 to 24 hours at a reaction temperature from 0° C. to about the boiling point of the solvent.

In this case, alkylating agents include, for example, alkyl halide such as methyl iodide, ethyl iodide, propyl iodide, and butyl iodide, or dialkyl sulfuric acid such as dimethyl sulfuric acid, diethyl sulfuric acid, dipropyl sulfuric acid, and dibutyl sulfuric acid, organic solvents include THF, DMF, DMA, or NMP, and bases include sodium hydride, sodium carbonate, potassium carbonate, and cesium carbonate.

In a certain aspect, the compound of the present invention can be produced according to Production Method 3 shown below. This production method is one embodiment of Production Method 1, in which the compound of formula (I'b) is obtained via Step C and Step D, using the compound of formula (IIb), i.e., the compound of formula (II) where R2 is Fmoc, as a starting material.

Production Method 3:

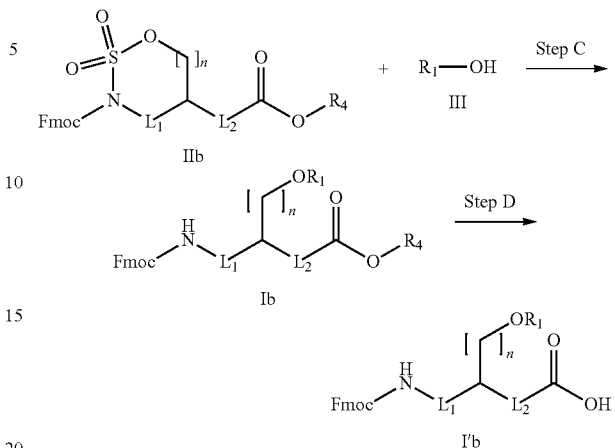

$R_1$, $R_4$, $L_1$, $L_2$, and n in the formula above are synonymous with $R_1$, $R_4$, $L_1$, $L_2$, and n in Production Method 1, respectively.

Step C (ring-opening addition reaction) is a step in which R1 is introduced by a nucleophilic substitution reaction of cyclic sulfamidate derivative (IIb) that is protected with Fmoc group with alcohol derivative (III) to produce O-substituted serine derivative (Ib) that is protected with Fmoc group. This reaction can be performed by stirring the reaction mixture for 1 to 48 hours in the presence or absence of a dissolution aid solvent, in the presence or absence of an acid salt, and at a temperature from −20° C. to about the boiling point of the solvent, preferably from 0° C. to 180° C.

The same dissolution aid solvents and the same acid salts as in Step C in Production Method 1 can be used, respectively. In this production method, it is preferable to use trifluoroethanol, hexafluoroisopropyl alcohol, dioxane, tetrahydrofuran, or NMP as a dissolution aid solvent, and NaH2PO4, KH2PO4, or CsH2PO4 as an acid salt.

Step D (deprotection reaction) is a step of producing O-substituted serine derivative (I'b), in which the carboxyl group is deprotected while the amino group remains protected with Fmoc group, by deprotecting the carboxyl protecting group (R4) of O-substituted serine derivative (Ib) that is protected with Fmoc group. This reaction can be performed by stirring the reaction mixture for 1 to 24 hours in the presence or absence of a metal catalyst, preferably a Pd catalyst, or an acid catalyst, in the presence or absence of a hydrogen source, and at a temperature from 0° C. to about the boiling point of the solvent.

The same metal catalysts, acid catalysts, hydrogen sources, and solvents as in Step D in Production Method 1 can be used, respectively. In this production method, it is preferable to use, for example, metal catalysts carried on a solid support represented by active carbon, such as palladium on carbon and palladium hydroxide on carbon, and palladium oxide, platinum oxide, Raney nickel, tetrakis(triphenylphosphine) palladium, bis(triphenylphosphine) palladium dichloride, tris(dibenzylideneacetone) dipalladium, and palladium acetate as a metal catalyst; for example, hydrochloric acid, hydrobromic acid, trifluoromethanesulfonic acid, and sulfuric acid as an acid catalyst; hydrogen gas, formic acid, or ammonium formate, and the like as a hydrogen source; and short-chain alkyl alcohol such as methanol and ethanol, and acetate ester derivative such as ethyl acetate and isopropyl acetate as a solvent.

In a certain aspect, the compound of the present invention can be produced according to Production Method 4-1 shown below. This production method is one embodiment of Production Method 1, in which the compound of formula (I'c) that is N-alkyl amino acid is obtained via Step C and Step D, using the compound of formula (IIc), i.e., the compound of formula (II) where R2 is alkyl, as a starting material, and then the compound of formula (I"c) is obtained via Step E.

Production Method 4-1:

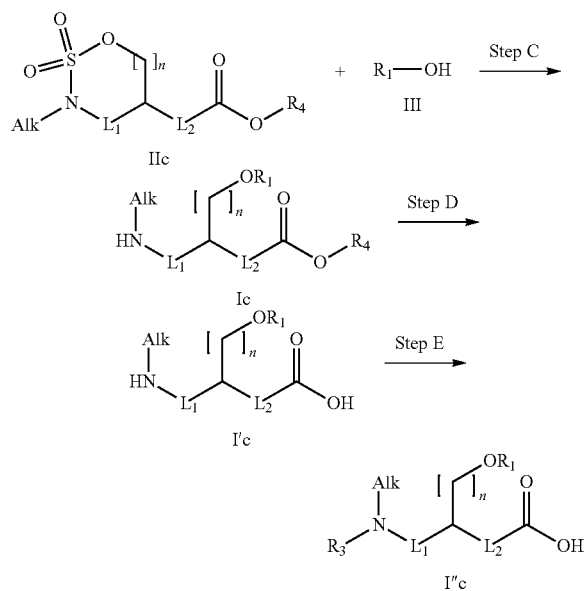

$R_1$, $R_3$, $R_4$, $L_1$, $L_2$, and n in the formula above are synonymous with $R_1$, $R_3$, $R_4$, $L_1$, $L_2$, and n in Production Method 1, respectively, and Alk is $C_1$-$C_4$ alkyl.

Step C (ring-opening addition reaction) is a step in which $R_1$ is introduced by a nucleophilic substitution reaction of alcohol derivative (III) with cyclic sulfamidate derivative (IIc) that is substituted with alkyl group to produce O-substituted serine derivative (Ic) that is substituted with alkyl group. This reaction can be performed by stirring the reaction mixture for 1 to 48 hours in the presence or absence of a dissolution aid solvent, in the presence or absence of an acid salt, and at a temperature from −20° C. to about the boiling point of the solvent, preferably from 0° C. to 180° C.

The same dissolution aid solvents and the same acid salts as in Step C in Production Method 1 can be used, respectively. In this production method, it is preferable to use trifluoroethanol, hexafluoroisopropyl alcohol, dioxane, tetrahydrofuran, or NMP as a dissolution aid solvent, and NaH2PO4, KH2PO4, or CsH2PO4 as an acid salt.

Step D (deprotection reaction) is a step of producing O-substituted serine derivative (I'c), in which the carboxyl group is deprotected while the amino group remains substituted with alkyl group, by deprotecting the carboxyl protecting group (R4) of O-substituted serine derivative (Ic) that is substituted with alkyl group. This reaction can be performed by stirring the reaction mixture for 1 to 24 hours in the presence or absence of a metal catalyst, preferably a Pd catalyst, or an acid catalyst, in the presence or absence of a hydrogen source, and at a temperature from 0° C. to about the boiling point of the solvent.

The same metal catalysts, acid catalysts, hydrogen sources, and solvents as in Step D in Production Method 1 can be used, respectively. In this production method, it is preferable to use, for example, metal catalysts carried on a solid support represented by active carbon, such as palladium on carbon and palladium hydroxide on carbon, and palladium oxide, platinum oxide, Raney nickel, tetrakis (triphenylphosphine) palladium, bis(triphenylphosphine) palladium dichloride, tris(dibenzylideneacetone) dipalladium, and palladium acetate as a metal catalyst; for example, hydrochloric acid, hydrobromic acid, trifluoromethanesulfonic acid, and sulfuric acid as an acid catalyst; hydrogen gas, formic acid, or ammonium formate, and the like as a hydrogen source; and short-chain alkyl alcohol such as methanol and ethanol, and acetate ester derivative such as ethyl acetate and isopropyl acetate as a solvent.

Step E (protecting group-introduction reaction) is a step in which a protecting group (R3) is introduced to an amino group by reacting the amino group of O-substituted serine derivative (I' c), where the amino group is substituted with alkyl group and the carboxyl group is deprotected, with a carbamating agent, to produce O-disubstituted serine derivative (I"c). This reaction can be performed by stirring the reaction mixture for 1 to 24 hours in the presence or absence of a base catalyst, and at a temperature from −10° C. to about the boiling point of the solvent.

The same carbamating agents, base catalysts, and solvents as in Step E in Production Method 1 can be used, respectively. In this production method, it is preferable to use, for example, Boc2O, BocOPh, FmocOSu, FmocCl, CbzCl, and AllocCl as a carbamating agent; for example, lithium carbonate, sodium carbonate, sodium hydrogen carbonate, potassium carbonate, potassium hydrogen carbonate, cesium carbonate, cesium hydrogen carbonate, lithium hydroxide, sodium hydroxide, potassium hydroxide, cesium hydroxide, sodium phosphate, potassium phosphate, N-methylmorpholine, triethylamine, diisopropylethylamine, and N,N-dimethylaminopyridine as a base catalyst; and acetonitrile, dichloromethane, tetrahydrofuran, dioxane, dimethylformamide, dimethylacetamide, and NMP as a solvent.

In a certain aspect, the compound of the present invention can be produced according to Production Method 4-2 shown below. This production method is one embodiment of Production Method 2, in which the compound of formula (I') having a free amino group that is synthesized via Step C and Step D is subjected to Step E to produce the compound of formula (I"c) that is N-alkyl amino acid.

Production Method 4-2:

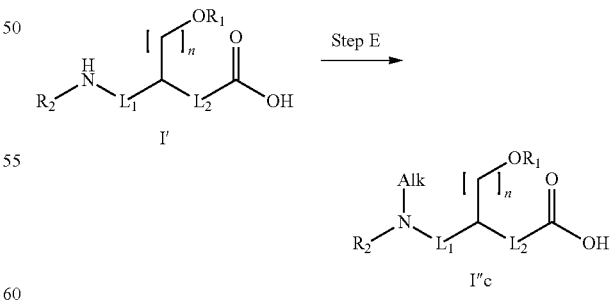

$R_1$, $R_2$, L1, L2, and n in the formula above are synonymous with R1, R2, L1, L2, and n in Production Method 2, respectively, and Alk is C1-C4 alkyl.

Step E (alkyl group-introduction reaction) can be performed using the method of Freidinger et al. (U.S. Pat. No. 4,535,167), or the method of Shimokawa et al. (Bioorg.

Med. Chem. Lett., 2009, 19(1), 92-95) or Prashad et al. (Org. Lett., 2003, 5(2), 125-128), as described above.

In a certain aspect, the compound of the present invention can be produced according to Production Method 5-1 shown below. This production method is one embodiment of Production Method 1, in which the compound of formula (I'd) is obtained via Step C, using the compound of formula (IId), i.e., the compound of formula (II) where R4 is —C(R5)3, as a starting material.

Production Method 5-1:

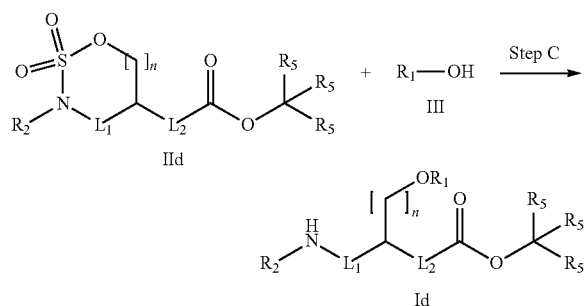

$R_1$, $R_2$, $L_1$, $L_2$, and n in the formula above are synonymous with $R_1$, $R_2$, $L_1$, $L_2$, and n in Production Method 1, respectively.

R5 in the formula above is optionally substituted C1-C6 alkyl group or an aromatic ring. Such R5 includes, for example, methyl, ethyl, and phenyl.

This Step C (ring-opening addition reaction) is a step in which N,O-disubstituted serine derivative (I'd) is produced by a nucleophilic substitution reaction of cyclic sulfamidate derivative (IId) with alcohol derivative (III). This reaction can be performed by stirring the reaction mixture for 1 to 48 hours in the presence or absence of a dissolution aid solvent, in the presence or absence of an acid salt, and at a temperature from −20° C. to about the boiling point of the solvent, preferably from 0° C. to 180° C.

The same dissolution aid solvents and the same acid salts as in Step C in Production Method 1 can be used, respectively. In this production method, it is preferable to use trifluoroethanol, hexafluoroisopropyl alcohol, dioxane, tetrahydrofuran, or NMP as a dissolution aid solvent, and NaH2PO4, KH2PO4, or CsH2PO4 as an acid salt.

In a certain aspect, the compound of the present invention can be produced according to Production Method 5-2 shown below. This production method is one embodiment of Production Method 2, in which the compound of formula (I'd) is obtained via Step C, using the compound of formula (II'd), i.e., the compound of formula (II) where $R_4$ is —C($R_5$)3, as a starting material.

Production Method 5-2:

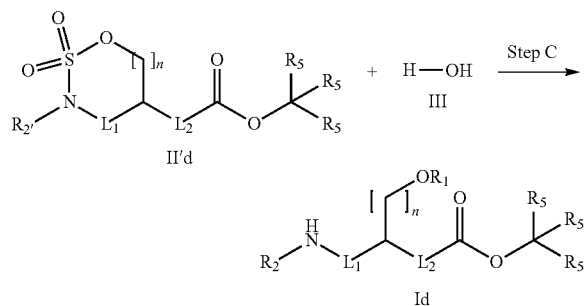

$R_1$, R2, R2', L1, L2, and n in the formula above are synonymous with R1, R2, R2', L1, L2, and n in Production Method 2, respectively.

R5 in the formula above is optionally substituted C1-C6 alkyl group or an aromatic ring. Such R5 includes, for example, methyl, ethyl, and phenyl.

This Step C (ring-opening addition reaction) is a step in which O-substituted serine derivative (Id) is produced by a nucleophilic substitution reaction of cyclic sulfamidate derivative (II'd) with alcohol derivative (III). This reaction can be performed by stirring the reaction mixture for 1 to 48 hours in the presence or absence of a dissolution aid solvent, in the presence or absence of an acid salt, and at a temperature from −20° C. to about the boiling point of the solvent, preferably from 0° C. to 180° C.

The same dissolution aid solvents and the same acid salts as in Step C in Production Method 2 can be used, respectively. In this production method, it is preferable to use trifluoroethanol, hexafluoroisopropyl alcohol, dioxane, tetrahydrofuran, or NMP as a dissolution aid solvent, and NaH2PO4, KH2PO4, or CsH2PO4 as an acid salt.

In a certain aspect, the compound of the present invention can be produced according, for example, to Production Method 6 shown below. This production method is one embodiment of Production Method 2, in which the compound of formula (I'e) is produced via Steps C to E, using as a starting material the compound of formula (II'e), i.e., the compound of formula (II') where R2' is a Boc group, and $R_4$ is C($R_5$)3.

Production Method 6:

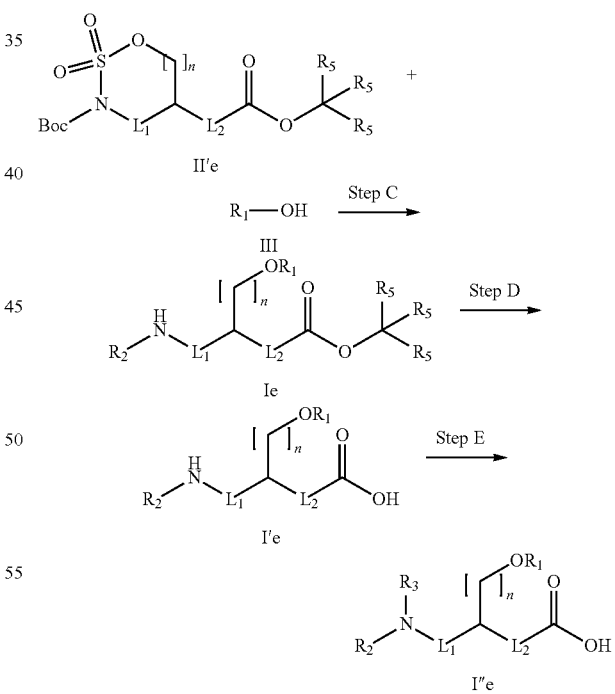

$R_1$, $R_2$, $R_3$, L1, L2, and n in the formula above are synonymous with R1, R2, R3, L1, L2, and n in Production Method 2, respectively.

R5 in the formula above is optionally substituted C1-C6 alkyl or an aromatic ring. Such R5 includes, for example, methyl, ethyl, and phenyl.

Step C (ring-opening addition reaction) is a step in which O-substituted serine derivative (Ie) having a free amino group is produced by a nucleophilic substitution reaction of N-Boc cyclic sulfamidate derivative (II'e) with alcohol derivative (III). This reaction can be performed by stirring the reaction mixture for 1 to 48 hours in the presence or absence of a dissolution aid solvent, in the presence or absence of an acid salt, and at a temperature from −20° C. to about the boiling point of the solvent, preferably from 0° C. to 180° C.

The same dissolution aid solvents and the same acid salts as in Step C in Production Method 2 can be used, respectively. In this production method, it is preferable to use trifluoroethanol, hexafluoroisopropyl alcohol, dioxane, tetrahydrofuran, or NMP as a dissolution aid solvent, and NaH2PO4, KH2PO4, or CsH2PO4 as an acid salt.

Step D (deprotection reaction) is a step in which O-substituted serine derivative (I'e) having a free amino group and a free carboxyl group is produced by deprotecting the carboxyl protecting group (C(R5)3) of O-substituted serine derivative (Ie). This reaction can be performed by stirring the reaction mixture for 1 to 24 hours in the presence or absence of a metal catalyst, preferably a Pd catalyst, or an acid catalyst, in the presence or absence of a hydrogen source, and at a temperature from 0° C. to about the boiling point of the solvent.

The same metal catalysts, acid catalysts, hydrogen sources, and solvents as in Step D in Production Method 1 can be used, respectively. In this production method, it is preferable to use, for example, metal catalysts carried on a solid support represented by active carbon, such as palladium on carbon and palladium hydroxide on carbon, and palladium oxide, platinum oxide, Raney nickel, tetrakis(triphenylphosphine) palladium, bis(triphenylphosphine) palladium dichloride, tris(dibenzylideneacetone) dipalladium, and palladium acetate as a metal catalyst; for example, hydrochloric acid, hydrobromic acid, trifluoromethanesulfonic acid, and sulfuric acid as an acid catalyst; hydrogen gas, formic acid, or ammonium formate, and the like as a hydrogen source; and short-chain alkyl alcohol such as methanol and ethanol, and acetate ester derivative such as ethyl acetate and isopropyl acetate as a solvent.

Step E (protecting group-introduction reaction) is a step in which R3 (i.e., an amino protecting group or an alkyl group) is introduced to an amino group of O-substituted serine derivative (I'e) to produce O-substituted serine derivative (I'e) having a free carboxyl group.

When introducing an amino protecting group, a carbamating agent is reacted to an α-amino group portion of O-substituted serine derivative (I'e). This reaction can be performed by stirring the reaction mixture for 1 to 24 hours in the presence or absence of a base catalyst and at a temperature from −10° C. to about the boiling point of the solvent.

The same carbamating agents, base catalysts, and solvents as in Step E in Production Method 2 can be used, respectively. In this production method, it is preferable to use, for example, Boc2O, BocOPh, FmocOSu, FmocCl, CbzCl, and AllocCl as a carbamating agent; for example, lithium carbonate, sodium carbonate, sodium hydrogen carbonate, potassium carbonate, potassium hydrogen carbonate, cesium carbonate, cesium hydrogen carbonate, lithium hydroxide, sodium hydroxide, potassium hydroxide, cesium hydroxide, sodium phosphate, potassium phosphate, N-methylmorpholine, triethylamine, diisopropylethylamine, and N,N-dimethylaminopyridine as a base catalyst; and acetonitrile, dichloromethane, tetrahydrofuran, dioxane, dimethylformamide, dimethylacetamide, and NMP as a solvent.

When introducing an alkyl group, the method of Freidinger et al. (U.S. Pat. No. 4,535,167), or the method of Shimokawa et al. (Bioorg. Med. Chem. Lett., 2009, 19(1), 92-95) or Prashad et al. (Org. Lett., 2003, 5(2), 125-128), as described above, can be used.

In a certain aspect, cyclic sulfamidate derivative (II) of the present invention used as a starting material in Step C in Production Method 1 can be produced according to a method comprising Step A and Step B shown below, using a known compound as a starting material.

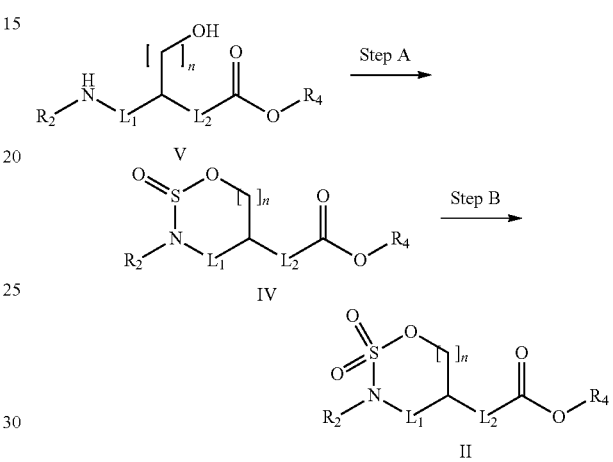

$R_2$ in the formula above is $C_1$-$C_6$ alkyl group or an amino protecting group. Such $R_2$ includes, for example, methyl, ethyl, benzyl, Fmoc, Boc, Cbz, or Alloc groups.

R4 in the formula above is a carboxyl protecting group. Such R4 includes, for example, alkyl such as t-butyl, and trityl, cumyl, allyl, and benzyl.

L1 in the formula above is a single bond or —CH2-, and L2 is a single bond or —CH2-. Herein, when L1 is —CH2-, L2 is a single bond, and when L2 is —CH2-, L1 is a single bond. Namely, a combination of L1 and L2 includes the following three: (i) L1=a single bond and L2=a single bond; (ii) L1=—CH2- and L2=a single bond; and (iii) L1=a single bond and L2=—CH2-.

In the formula above, n represents the number of methylene group, and n is 1 or 2.

Step A is a step in which α-amino acid (V) having a hydroxyl group is cyclized using a cyclization reagent to produce cyclic sulfamidite derivative (IV). This reaction can be performed by stirring the reaction mixture for 1 to 24 hours in the presence or absence of a solvent, in the presence or absence of a base, and at a temperature from −40° C. to 25° C., preferably from −40° C. to 0° C.

Cyclization reagents specifically include thionyl chloride, sulfuryl chloride, and such, and thionyl chloride is preferably used. A cyclization reagent that is 1.5 to 5 equivalents to the starting material can preferably be used.

Solvents include ethyl acetate, isopropyl acetate, butyl acetate, dichloromethane, and acetonitrile.

Bases include pyridine, TEA, and DIPEA, and pyridine can preferably be used.

Step B is a step in which a sulfur atom in a ring of cyclic sulfamidite derivative (IV) is oxidized to a sulfone using an oxidizing agent to produce cyclic sulfamidate derivative (II). This reaction can be performed by stirring the reaction mixture for 1 to 24 hours in the presence or absence of a solvent and at a temperature from −20° C. to 25° C.

Oxidizing agents specifically include hydrogen peroxide, organic peroxide, persulfate, halogen oxide, or a combination of halogen oxide and transition metal catalyst. Of these, 3-chloroperbenzoic acid, oxone, or a combination of periodate and ruthenium catalyst is preferably used, and as periodate, more specifically, sodium periodate or potassium periodate can preferably be used. As ruthenium catalyst, more specifically, ruthenium trichloride anhydride or ruthenium trichloride hydrate is preferably used. When a combination of periodate and ruthenium catalyst is used as an oxidizing agent, periodate that is 1.5 to 5 equivalents to the starting material and ruthenium catalyst that is 0.01 to 0.2 equivalents to the starting material are preferably used.

As a solvent, acetonitrile, water, ethyl acetate, isopropyl acetate, and a combination thereof is preferably used, and a solvent mixture of acetonitrile and water is more preferably used.

In a certain aspect, cyclic sulfamidate derivative (II') of the present invention used as a starting material in Step C in Production Method 2 can be produced according to a method comprising Step A and Step B shown below, using a known compound as a starting material.

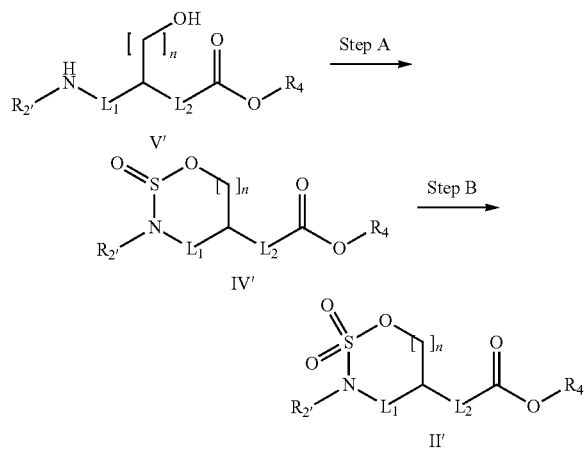

$R_{2'}$ in the formula above is an amino protecting group. Such $R_{2'}$ includes, for example, Fmoc, Boc, Cbz, or Alloc groups.

R4 in the formula above is a carboxyl protecting group. Such R4 includes, for example, alkyl such as t-butyl, and trityl, cumyl, allyl, and benzyl.

L1 in the formula above is a single bond or —CH2-, and L2 is a single bond or —CH2-. Herein, when L1 is —CH2-, L2 is a single bond, and when L2 is —CH2-, L1 is a single bond. Namely, a combination of L1 and L2 includes the following three: (i) L1=a single bond and L2=a single bond; (ii) L1=—CH2- and L2=a single bond; and (iii) L1=a single bond and L2=—CH2-.

In the formula above, n represents the number of methylene group, and n is 1 or 2.

Step A is a step in which α-amino acid (V') having a hydroxyl group is cyclized using a cyclization reagent to produce cyclic sulfamidite derivative (IV'). This reaction can be performed by stirring the reaction mixture for 1 to 24 hours in the presence or absence of a solvent, in the presence or absence of a base, and at a temperature from −40° C. to 25° C., preferably from −40° C. to 0° C.

Cyclization reagents specifically include thionyl chloride and sulfuryl chloride, and thionyl chloride is preferably used. A cyclization reagent that is 1.5 to 5 equivalents to the starting material can preferably be used.

Solvents include ethyl acetate, isopropyl acetate, butyl acetate, dichloromethane, and acetonitrile.

Bases include pyridine, TEA, and DIPEA, and pyridine can preferably be used.

Step B is a step in which a sulfur atom in a ring of cyclic sulfamidite derivative (IV') is oxidized to a sulfone using an oxidizing agent to produce cyclic sulfamidate derivative (II'). This reaction can be performed by stirring the reaction mixture for 1 to 24 hours in the presence or absence of a solvent and at a temperature from −20° C. to 25° C.

Oxidizing agents specifically include hydrogen peroxide, organic peroxide, persulfate, halogen oxide, or a combination of halogen oxide and transition metal catalyst. Of these, 3-chloroperbenzoic acid, oxone, or a combination of periodate and ruthenium catalyst is preferably used, and as periodate, more specifically, sodium periodate or potassium periodate can preferably be used. As ruthenium catalyst, more specifically, ruthenium trichloride anhydride or ruthenium trichloride hydrate is preferably used. When a combination of periodate and ruthenium catalyst is used as an oxidizing agent, periodate that is 1.5 to 5 equivalents to the starting material and ruthenium catalyst that is 0.01 to 0.2 equivalents to the starting material are preferably used.

As a solvent, acetonitrile, water, ethyl acetate, isopropyl acetate, and a combination thereof is preferably used, and a solvent mixture of acetonitrile and water is more preferably used.

In a certain aspect, cyclic sulfamidate derivative (IId or IIe) used as a starting material in Step C can be produced according to a method comprising Step A and Step B shown below, using a known compound as a starting material.

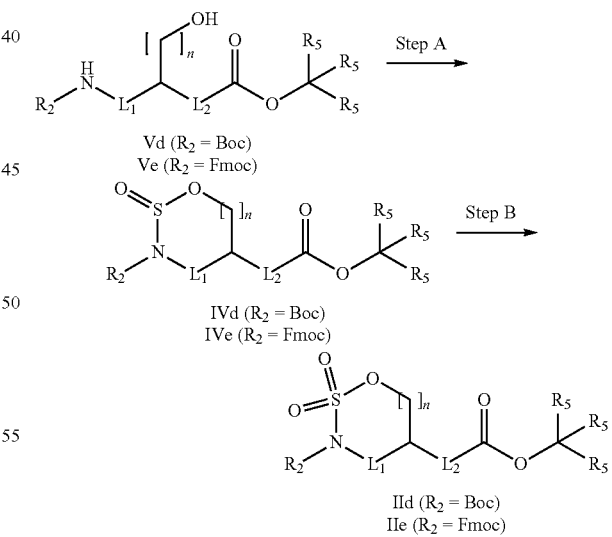

$R_5$ in the formula above is optionally substituted C1-C6 alkyl or an aromatic ring, preferably, for example, methyl, ethyl, and phenyl.

L1 in the formula above is a single bond or —CH2-, and L2 is a single bond or —CH2-. Herein, when L1 is —CH2-, L2 is a single bond, and when L2 is —CH2-, L1 is a single bond. Namely, a combination of L1 and L2 includes the following three: (i) L1=a single bond and L2=a single bond; (ii) L1=—CH2- and L2=a single bond; and (iii) L1=a single bond and L2=—CH2-.

In the formula above, n represents the number of methylene group, and n is 1 or 2.

Step A is a step in which α-amino acid (Vd) or (Ve) having a hydroxyl group is cyclized using a cyclization reagent to produce cyclic sulfamidite derivative (IVd) or (IVe). This reaction can be performed by stirring the reaction mixture for 1 to 24 hours in the presence or absence of a solvent, in the presence or absence of a base, and at a temperature from −40° C. to 25° C., preferably from −40° C. to 0° C.

Step B is a step in which a sulfur atom in a ring of cyclic sulfamidite derivative (IVd) or (IVe) is oxidized to a sulfone using an oxidizing agent to produce cyclic sulfamidate derivative (IId) or (IIe). This reaction can be performed by stirring the reaction mixture for 1 to 24 hours in the presence or absence of a solvent and at a temperature from −20° C. to 25° C.

In Step A and Step B, the reactions can be performed using a cyclization reagent, an oxidizing agent, a solvent, and a base, respectively described above. The cyclic sulfamidate derivative (IId) or (IIe) obtained can be used as a starting material not only in Production Method 1 but also in Production Method 2. In this case, R2 in the formula above is read as R2'.

The isolation and purification of the objective compounds obtained via each reaction step described above can be performed using conventional chemical operations such as extraction, concentration, distillation, crystallization, filtration, recrystallization, and various chromatography techniques.

The compounds of the present invention and the chemically acceptable salts thereof include all of the stereoisomers (e.g., enantiomers and diastereomers (including cis- and trans-geometrical isomers)) of the objective compounds obtained via each reaction step described above, the racemate of the isomers, and other mixtures. For example, the compounds of the present invention of formula (I), (I'), (I"), and (II) above may have one or more asymmetric points, and the racemic mixture, diastereomeric mixture, and enantiomers of such compounds are included in the present invention.

When the compounds of the present invention are obtained as the free forms, the compounds can be converted to the salts which may be formed with the compounds, or the hydrates or the solvates thereof, according to conventional methods.

When the compounds of the present invention are obtained as the salts, the hydrates, or the solvates of the compounds, they can be converted to the free forms thereof according to conventional methods.

All of the prior art literatures cited herein are incorporated herein by reference.

EXAMPLE

Herein below, the present invention is explained in further detail with reference to Examples, but it is not to be construed as being limited thereto.

Condition 1 for High Performance Liquid Chromatography
  Equipment: UPLC ACQUITY, Waters Corporation;
  Column: BEH (1.7 μm, 2.1 mm I.D.×50 mm, Waters Corporation);
  Mobile phase: water containing 0.05% trifluoroacetic acid (A) and acetonitrile containing 0.05% trifluoroacetic acid (B);
  Elution: stepwise solvent gradient elution with 5% B to 100% B (4.0 min.), hold at 100% B (0.5 min.);
  Flow rate: 0.5 mL/min.
  Column temperature: 35° C.

Condition 2 for High Performance Liquid Chromatography
  Equipment: UPLC ACQUITY, Waters Corporation;
  Column: BEH (1.7 μm, 2.1 mm I.D.×50 mm, Waters Corporation);
  Mobile phase: water containing 0.1% formic acid (A) and acetonitrile containing 0.1% formic acid (B);
  Elution: stepwise solvent gradient elution with 5% B to 100% B (4.0 min.), hold at 100% B (0.5 min.);
  Flow rate: 0.5 mL/min.
  Column temperature: 25° C.

Condition 3 for High Performance Liquid Chromatography
  Equipment: UPLC ACQUITY, Waters Corporation;
  Column: CHIRALCELL OD-3R (3.0 μm, 4.6 mm I.D.×50 mm, Daicel Corporation); Mobile phase: water containing 0.1% formic acid (A) and acetonitrile containing 0.1% formic acid (B);
  Elution: stepwise solvent gradient elution with 5% B to 100% B (4.0 min.), hold at 100% B (0.5 min.);
  Flow rate: 1.5 mL/min.
  Column temp.: 25° C.

Condition 4 for High Performance Liquid Chromatography
  Equipment: UPLC ACQUITY, Waters Corporation;
  Column: CHIRALPAK IA-3 (3.0 μm, 4.6 mm I.D.×50 mm, Daicel Corporation);
  Mobile phase: water containing 10 mM ammonium acetate (A) and methanol containing 10 mM ammonium acetate (B);
  Elution: stepwise solvent gradient elution with 5% B to 60% B (0.5 min.), 60% B to 80% B (3.0 min.), 80% B to 100% B (0.5 min.), hold at 100% B (0.5 min.);
  Flow rate: 1.2 mL/min.
  Column temperature: 25° C.

Condition 5 for High Performance Liquid Chromatography
  Equipment: UPLC ACQUITY, Waters Corporation;
  Column: CHIRALPAK IG-3 (3.0 μm, 4.6 mm I.D.×50 mm, Daicel Corporation);
  Mobile phase: water containing 10 mM ammonium acetate (A) and methanol containing 10 mM ammonium acetate (B);
  Elution: stepwise solvent gradient elution with 5% B to 60% B (0.1 min.), 60% B to 100% B (3.4 min.), hold at 100% B (1.0 min.);
  Flow rate: 1.2 mL/min.
  Column temperature: 25° C.

$^1$H-NMR spectrum was measured using AVANCE III HD 400 BBFO-SMART probe (Bruker corporation), where the chemical shift of Me$_4$Si used as an internal standard was set to be 0 ppm, and the deuterium lock signal from the sample solvent was used as a reference. The chemical shifts of the signals of the analyte compound were expressed in ppm. The abbreviations for signal splitting were: s=singlet, brs=broad singlet, d=doublet, t=triplet, q=quartet, dd=double doublet, and m=multiplet, and the separation in a split signal was expressed in J (Hz). The integrated value of a signal was calculated based on the ratio of signal area intensity of the signals. Production example using Boc-Ser-OBzl as a starting material.

Example 1: benzyl (4S)-5-t-butoxycarbonyl-1,2,5-sulfamidate-4-carboxylate

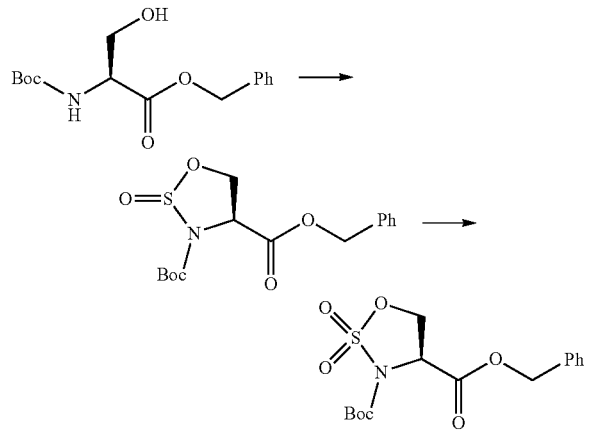

1) To a solution consisting of thionyl chloride 16.1 g (135 mmol) and ethyl acetate 400 mL cooled to −15° C., a solution consisting of Boc-Ser-OBzl 20 g (68 mmol) and ethyl acetate 50 mL was added dropwise over 5 minutes. The reaction mixture was stirred at the same temperature for 5 minutes, and then pyridine 26.8 g (338 mmol) was added dropwise over 5 minutes. The reaction mixture was stirred at the same temperature for 15 minutes, and then at room temperature for 22 hours. To the reaction mixture, water 200 mL was added, and the organic layer and the aqueous layer were separated. The organic layer obtained was washed with 1N-hydrochloric acid 200 mL and 10% brine 200 mL, and concentrated under reduced pressure to give a crude product of benzyl (4S)-5-t-butoxycarbonyl-1,2,5-sulfamiditecarboxylate 23.9 g as a diastereomeric mixture.

2) To a solution consisting of the crude product of benzyl (4S)-5-t-butoxycarbonyl-1,2,5-sulfamiditecarboxylate 23.9 g and acetonitrile 100 mL cooled to 0° C., a solution consisting of sodium periodate 21.7 g (101 mmol), ruthenium chloride hydrate 0.14 g (0.68 mmol), and water 300 mL was added dropwise over 8 minutes. The reaction mixture was stirred at the same temperature for 22 minutes, and then at room temperature for 1 hour. To the reaction mixture, 10% aqueous sodium carbonate 60 mL, water 100 mL, and ethyl acetate 220 mL were added, and the organic layer and the aqueous layer were separated. To the aqueous layer obtained, ethyl acetate 100 mL was added again, and the organic layer and the aqueous layer were separated. The organic layers obtained were combined, washed with 10% brine 200 mL, and concentrated under reduced pressure to give benzyl (4S)-5-t-butoxycarbonyl-1,2,5-sulfamidatecarboxylate 22.3 g as a crude product.

3) To a mixture consisting of the crude product of benzyl (4S)-5-t-butoxycarbonyl-1,2,5-sulfamidatecarboxylate 22.3 g and ethyl acetate 70 mL heated to 50° C., hexane 280 mL was added, and after a precipitate appeared, the reaction mixture was stirred at room temperature for 2 hours, and the precipitate was collected by filtration under reduced pressure. The crystals obtained were dried under reduced pressure to give benzyl (4S)-5-t-butoxycarbonyl-1,2,5-sulfamidatecarboxylate 19.8 g (yield: 81.6% in 2 steps) as white crystals.

Benzyl (4S)-5-t-butoxycarbonyl-1,2,5-sulfamidate-4-carboxylate

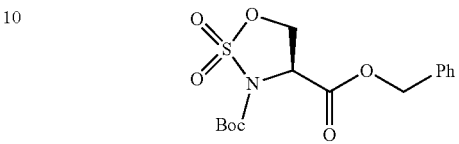

Optical purity: 99.9% ee (detection wavelength 205 nm, retention time 2.87 min., condition 3 for high performance liquid chromatography) UV intensity ratio: 99.2% (detection wavelength 205 nm, retention time 2.77 min., condition 2 for high performance liquid chromatography)

$^1$H-NMR (CDCl$_3$, 400 MHz) δ: 1.50 (9H, s), 4.67 (1H, dd, J=9.6, 2.0), 4.76 (1H, dd, J=9.6, 6.4), 4.80-4.86 (1H, m), 5.23 (1H, d, J=12.0), 5.32 (1H, d, J=12.0), 7.30-7.42 (5H, m)

Example 2: Fmoc-Ser(n-Pr)—OH

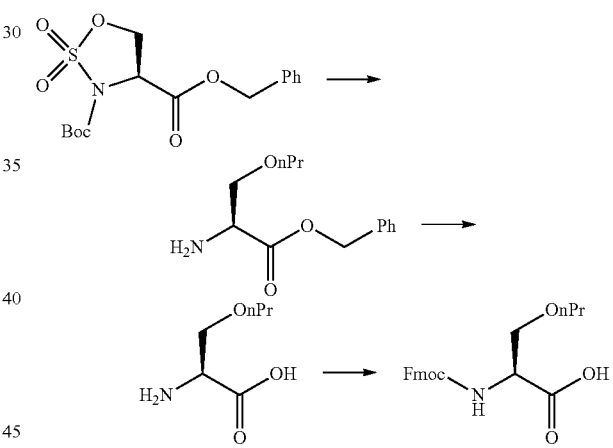

1) A mixture consisting of benzyl (4S)-5-t-butoxycarbonyl-1,2,5-sulfamidatecarboxylate 6.00 g (16.7 mmol) and 1-propanol 120 mL was stirred for 12 hours while heating at 90° C. To the reaction mixture, ethyl acetate 240 mL and 5% aqueous sodium hydrogen carbonate 240 mL were added, and the organic layer and the aqueous layer were separated. The organic layer obtained was washed with 10% brine 240 mL to give H-Ser(n-Pr)-OBzl as an ethyl acetate solution.

H-Ser(n-Pr)-OBzl

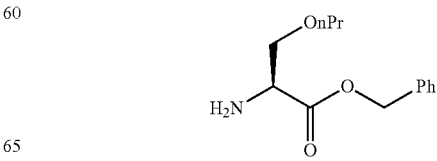

Optical purity: 99.5% ee (detection wavelength 205 nm, retention time 2.76 min., condition 4 for high performance liquid chromatography)

UV intensity ratio: 87.3% (detection wavelength 205 nm, retention time 1.42 min., condition 2 for high performance liquid chromatography)

2) To a solution of H-Ser(n-Pr)-OBzl in ethyl acetate, a mixture of 10% palladium on carbon 0.6 g and methanol 30 mL was added, and the reaction mixture was stirred under hydrogen gas atmosphere at room temperature for 2 hours. Palladium catalyst was filtered out using Celite under reduced pressure, and the mixture obtained was concentrated under reduced pressure to give H-Ser(n-Pr)—OH 7.82 g as a crude product.

3) To a solution consisting of H-Ser(n-Pr)—OH 7.82 g, water 96 mL, and sodium carbonate 4.80 g (45.2 mmol) cooled to 0° C., a solution consisting of FmocOSu 4.00 g (11.8 mmol) and acetonitrile 96 mL was added dropwise over 5 minutes. The reaction mixture was stirred at room temperature for 24 hours, 2N-hydrochloric acid 48 mL and water 48 mL were added thereto over 10 minutes and after a precipitate appeared, the reaction mixture was stirred at room temperature for 2 hours. To the reaction mixture, water 24 mL was added, and the mixture was stirred for 1 hour, additional water 24 mL was added, and the mixture was stirred for 2 hours, and then the precipitate was collected by filtration under reduced pressure. The crystals obtained were dried under reduced pressure to give Fmoc-Ser(n-Pr)—OH 3.60 g (yield: 58.4% in 3 steps) as white crystals.

Fmoc-Ser(n-Pr)—OH

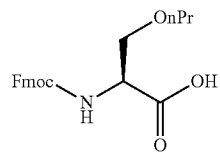

Optical purity: 99.6% ee (detection wavelength 205 nm, retention time 3.35 min., condition 3 for high performance liquid chromatography) UV intensity ratio: 96.2% (detection wavelength 205 nm, retention time 2.74 min., condition 2 for high performance liquid chromatography)

$^1$H-NMR (DMSO-d6, 400 MHz) δ: 0.84 (3H, t, J=7.2), 1.42-1.56 (2H, m), 3.28-3.42 (2H, m), 3.56-3.70 (2H, m), 4.16-4.34 (4H, m), 7.32 (2H, dt, J=7.2, 0.8), 7.42 (2H, t, J=7.6), 7.61 (1H, d, J=8.0), 7.74 (2H, d, J=7.8), 7.89 (2H, d, J=7.6), 12.76 (1H, brs) yy Example 3: Fmoc-Ser(i-Pr)—OH

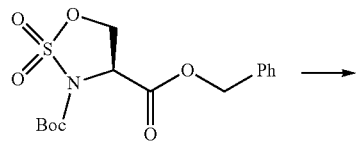

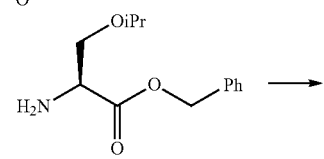

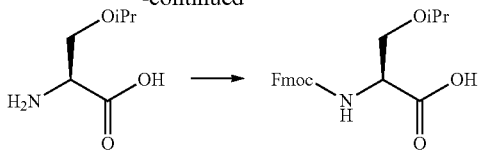

1) A mixture consisting of benzyl (4S)-5-t-butoxycarbonyl-1,2,5-sulfamidatecarboxylate 1.00 g (2.8 mmol) and 2-propanol 20 mL was stirred for 36 hours while heating at 80° C. To the reaction mixture, ethyl acetate 20 mL, 5% aqueous sodium hydrogen carbonate 20 mL, and 10% brine 20 mL were added, and the organic layer and the aqueous layer were separated. The organic layer was obtained as an ethyl acetate solution of H-Ser(i-Pr)-OBzl.

H-Ser(i-Pr)-OBzl

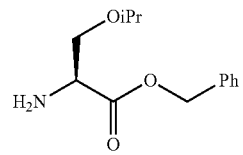

Optical purity: 99.9% ee (detection wavelength 205 nm, condition 4 for high performance liquid chromatography)

UV intensity ratio: 84.4% (detection wavelength 205 nm, retention time 1.38 min., condition 2 for high performance liquid chromatography)

2) To a solution of H-Ser(i-Pr)-OBzl in ethyl acetate, a mixture of 10% palladium on carbon 0.15 g and methanol 5 mL was added, and the reaction mixture was stirred under hydrogen gas atmosphere at room temperature for 2 hours. Palladium catalyst was filtered out using Celite under reduced pressure, and the mixture obtained was concentrated under reduced pressure to give H-Ser(i-Pr)—OH 842 mg as a crude product.

3) To a solution consisting of H-Ser(i-Pr)—OH 842 mg, water 6 mL, and sodium carbonate 0.31 g (2.9 mmol) cooled to 0° C., a solution consisting of FmocOSu 0.66 g (2.0 mmol) and acetonitrile 6 mL was added dropwise over 2 minutes. The reaction mixture was stirred at room temperature for 3 hours, 1N-hydrochloric acid 10 mL was added thereto over 5 minutes, and after a precipitate appeared, the reaction mixture was stirred at room temperature for 3 hours. After stirring the reaction mixture for 3 hours, the precipitate was collected by filtration under reduced pressure. The crystals obtained were dried under reduced pressure to give Fmoc-Ser(i-Pr)—OH 667 mg (yield: 63.5% in 3 steps) as white crystals.

Fmoc-Ser(i-Pr)—OH

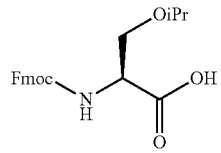

Optical purity: 99.9% ee (detection wavelength 205 nm, retention time 3.25 min., condition 3 for high performance liquid chromatography)

UV intensity ratio: 98.7% (detection wavelength 205 nm, retention time 2.74 min., condition 2 for high performance liquid chromatography)

¹H-NMR (DMSO-d6, 400 MHz) δ: 1.06 (3H, d, J=6.0), 1.08 (3H, d, J=6.0), 3.48-3.66 (3H, m), 4.10-4.32 (4H, m), 7.33 (2H, dt, J=7.6, 0.8), 7.42 (2H, t, J=7.0), 7.56 (1H, d, J=8.0), 7.74 (2H, d, J=7.8), 7.89 (2H, d, J=7.6), 12.73 (1H, brs)

Example 4: H-Ser(2-hydroxy-2-methylpropyl)-OBzl

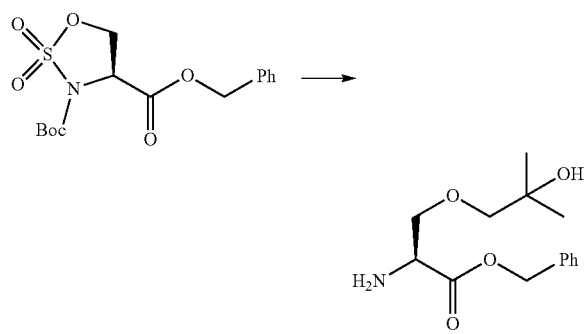

A mixture consisting of benzyl (4S)-5-t-butoxycarbonyl-1,2,5-sulfamidatecarboxylate 50 mg (0.10 mmol) and 2-methylpropane-1,2-diol 1.00 mL was stirred for 30 hours while heating at 80° C., and the reaction mixture was analyzed with HPLC.

H-Ser(2-hydroxy-2-methylpropyl)-OBzl

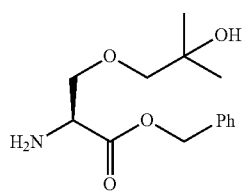 [SMILES: CC(C)(O)COC[C@H](N)C(=O)OCc1ccccc1]

Optical purity: 99.9% ee (detection wavelength 205 nm, retention time 1.78 min., condition 4 for high performance liquid chromatography)

UV intensity ratio: 73.3% (detection wavelength 205 nm, retention time 1.22 min., condition 2 for high performance liquid chromatography)

Example 5: H-Ser(n-Bu)-OBzl

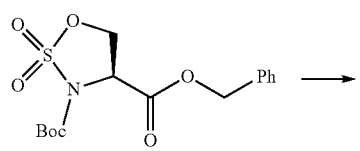

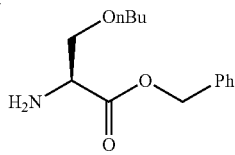

A mixture consisting of benzyl (4S)-5-t-butoxycarbonyl-1,2,5-sulfamidatecarboxylate 25 mg (0.07 mmol) and 1-butanol 0.50 mL was stirred for 24 hours while heating at 80° C., and the reaction mixture was analyzed with HPLC.

H-Ser(n-Bu)-OBzl

UV intensity ratio: 77.0% (detection wavelength 205 nm, retention time 1.83 min., condition 1 for high performance liquid chromatography)

ESI (LC/MS positive mode) m/z: 252.48 (M+H⁺)

Example 6: H-Ser(3-methylbutyl)-OBzl

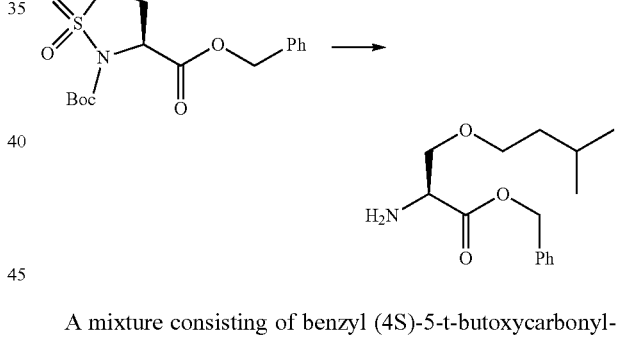

A mixture consisting of benzyl (4S)-5-t-butoxycarbonyl-1,2,5-sulfamidatecarboxylate 25 mg (0.07 mmol) and 3-methylbutanol 0.50 mL was stirred for 24 hours while heating at 80° C., and the reaction mixture was analyzed with HPLC.

H-Ser(3-methylbutyl)-OBzl

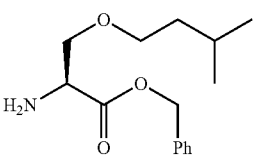 [SMILES: CC(C)CCOC[C@H](N)C(=O)OCc1ccccc1]

UV intensity ratio: 73.9% (detection wavelength 205 nm, retention time 2.00 min., condition 1 for high performance liquid chromatography)

ESI (LC/MS positive mode) m/z: 266.52 (M+H⁺)

Example 7: Benzyl (4S)-1,2,5-sulfamidate-4-carboxylate

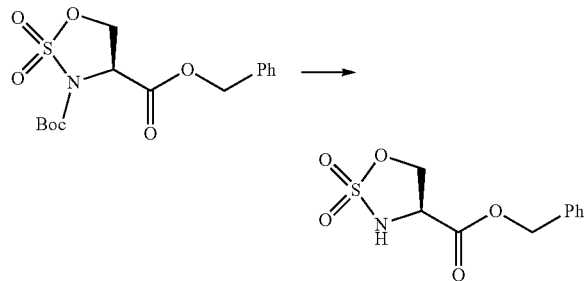

A mixture consisting of benzyl (4S)-5-t-butoxycarbonyl-1,2,5-sulfamidatecarboxylate 1.00 g (2.8 mmol) and 2,2,2-trifluoroethanol 10 mL was stirred for 4 hours while heating at 70° C. To the reaction mixture, ethyl acetate 20 mL and 5% brine 40 mL were added, and the organic layer and the aqueous layer were separated. The organic layer was concentrated under reduced pressure to give benzyl (4S)-1,2,5-sulfamidatecarboxylate 734 mg as a crude product.

The crude product obtained was purified with silica gel column chromatography (elution solvent: ethyl acetate-hexane) to give benzyl (4S)-1,2,5-sulfamidatecarboxylate 649 mg (yield: 90.2%) as a pale yellow solid.

Benzyl (4S)-1,2,5-sulfamidatecarboxylate

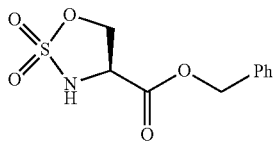 [SMILES: O=C(OCc1ccccc1)[C@@H]1COS(=O)(=O)N1]

UV intensity ratio: 99.6% (detection wavelength 205 nm, retention time 1.94 min., condition 1 for high performance liquid chromatography)

$^1$H-NMR (CDCl$_3$, 400 MHz) δ: 4.44-4.52 (1H, m), 4.56 (1H, dd, J=8.8, 5.6), 4.74 (1H, dd, J=8.8, 7.6), 5.09-5.18 (1H, m), 5.27 (1H, d, J=11.6), 5.30 (1H, d, J=11.6), 7.32-7.44 (5H, m)

Production example using D-Boc-Ser-OBzl as a starting material

Example 8: Benzyl (4R)-5-t-butoxycarbonyl-1,2,5-sulfamidate-4-carboxylate

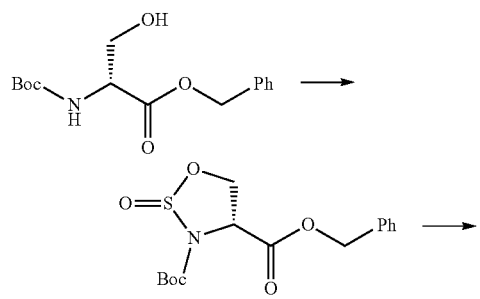

-continued

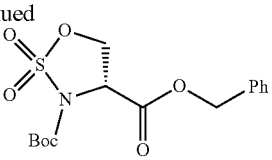

1) To a solution consisting of thionyl chloride 8.05 g (67.7 mmol) and acetonitrile 140 mL cooled to −40° C., a solution consisting of D-Boc-Ser-OBzl 10.0 g (33.8 mmol) and acetonitrile 30 mL was added dropwise over 5 minutes. The reaction mixture was stirred at the same temperature for 5 minutes, and then pyridine 13.4 g (169 mmol) was added dropwise over 5 minutes. The reaction mixture was stirred at the same temperature for 5 minutes, and then at room temperature for 4 hours. To the reaction mixture, water 340 mL and ethyl acetate 170 mL were added, and the organic layer and the aqueous layer were separated. The organic layer obtained was washed with 5% aqueous sodium hydrogen carbonate 170 mL, and with a mixed solution of 0.5N-hydrochloric acid 170 mL and 10% brine 170 mL, and concentrated under reduced pressure to give a crude product of benzyl (4R)-5-t-butoxycarbonyl-1,2,5-sulfamiditecarboxylate 10.76 g as a diastereomeric mixture.

2) To a solution consisting of the crude product of benzyl (4R)-5-t-butoxycarbonyl-1,2,5-sulfamiditecarboxylate 10.76 g and acetonitrile 160 mL cooled to 0° C., a solution consisting of sodium periodate 10.7 g (50 mmol), ruthenium chloride hydrate 62 mg (0.30 mmol), and water 160 mL was added dropwise over 15 minutes. The reaction mixture was stirred at the same temperature for 2 hours. To the reaction mixture, 5% aqueous sodium hydrogen carbonate 160 mL and ethyl acetate 160 mL were added, and the organic layer and the aqueous layer were separated. To the aqueous layer obtained, ethyl acetate 160 mL was added again, and the organic layer and the aqueous layer were separated. The organic layers obtained were combined, washed with 10% brine 160 mL, and concentrated under reduced pressure to give benzyl (4R)-5-t-butoxycarbonyl-1,2,5-sulfamidatecarboxylate 10.44 g as a crude product.

3) To a mixture consisting of the crude product of benzyl (4R)-5-t-butoxycarbonyl-1,2,5-sulfamidatecarboxylate 10.44 g and ethyl acetate 30 mL heated to 40° C., hexane 120 mL was added, and after a precipitate appeared, the reaction mixture was stirred at room temperature for 2 hours, and the precipitate was collected by filtration under reduced pressure. The crystals obtained were dried under reduced pressure to give benzyl (4R)-5-t-butoxycarbonyl-1,2,5-sulfamidatecarboxylate 9.00 g (yield: 74.5% in 2 steps) as white crystals.

Benzyl (4R)-5-t-butoxycarbonyl-1,2,5-sulfamidate-carboxylate

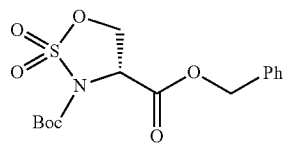 [SMILES: CC(C)(C)OC(=O)N1[C@@H](C(=O)OCc2ccccc2)COS1(=O)=O]

Optical purity: 99.9% ee (detection wavelength 205 nm, retention time 2.93 min., condition 3 for high performance liquid chromatography)

UV intensity ratio: 97.7% (detection wavelength 205 nm, retention time 2.77 min., condition 2 for high performance liquid chromatography)

¹H-NMR (CDCl₃, 400 MHz) δ: 1.49 (9H, s), 4.67 (1H, dd, J=9.6, 2.2), 4.76 (1H, dd, J=9.6, 6.4), 4.80-4.86 (1H, m), 5.23 (1H, d, J=12.0), 5.32 (1H, d, J=12.0), 7.30-7.42 (5H, m)

Example 9: Racemization of D-H-Ser(n-Pr)-OBzl

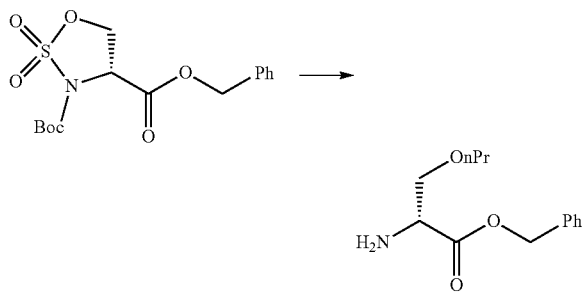

1) Reaction mixture: A mixture consisting of benzyl (4R)-5-t-butoxycarbonyl-1,2,5-sulfamidatecarboxylate 1.00 g (2.8 mmol) and 1-propanol 20 mL was stirred for 15 hours while heating at 90° C., and the reaction mixture was analyzed with HPLC.

D-H-Ser(n-Pr)-OBzl

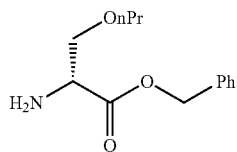

Optical purity: 99.9% ee (detection wavelength 205 nm, retention time 2.54 min., condition 4 for high performance liquid chromatography)

UV intensity ratio: 82.1% (detection wavelength 205 nm, retention time 1.40 min., condition 2 for high performance liquid chromatography)

2) Ethyl acetate solution 1: To the reaction mixture, ethyl acetate 40 mL and 5% aqueous sodium hydrogen carbonate 40 mL were added, and the organic layer and the aqueous layer were separated. The organic layer obtained was analyzed with HPLC.

Optical purity: 99.9% ee (detection wavelength 205 nm, retention time 2.55 min., condition 4 for high performance liquid chromatography)

UV intensity ratio: 84.7% (detection wavelength 205 nm, retention time 1.42 min., condition 2 for high performance liquid chromatography)

3) Ethyl acetate solution 2: The ethyl acetate solution 1 obtained was divided into two, and one part of them was washed twice with 10% brine 20 mL, and the organic layer obtained was analyzed with HPLC.

Optical purity: 99.8% ee (detection wavelength 205 nm, retention time 2.55 min., condition 4 for high performance liquid chromatography)

UV intensity ratio: 85.1% (detection wavelength 205 nm, retention time 1.42 min., condition 2 for high performance liquid chromatography)

4) Crude product 1: The ethyl acetate solution 2 obtained was divided into two, and one part of them was concentrated under reduced pressure in a water bath set at 25° C., and the crude product of D-H-Ser(n-Pr)-OBzl obtained was analyzed with HPLC.

Optical purity: 82.8% ee (detection wavelength 205 nm, retention time 2.54 min., condition 4 for high performance liquid chromatography)

UV intensity ratio: 79.7% (detection wavelength 205 nm, retention time 1.39 min., condition 2 for high performance liquid chromatography)

5) Crude product 2: The other part of the organic layer that was divided into two was concentrated under reduced pressure in a water bath set at 50° C., and the crude product of D-H-Ser(n-Pr)-OBzl obtained was analyzed with HPLC.

Optical purity: 72.6% ee (detection wavelength 205 nm, retention time 2.53 min., condition 4 for high performance liquid chromatography)

UV intensity ratio: 79.1% (detection wavelength 205 nm, retention time 1.39 min., condition 2 for high performance liquid chromatography)

Example 10: Stability of the Optical Purity of D-H-Ser(n-Pr)-OBzl

1) Two types of ethyl acetate solution prepared in Example 9 were left to stand at room temperature for 3 days, and were analyzed with HPLC.
Ethyl Acetate Solution 1:
Optical purity: 91.5% ee (detection wavelength 205 nm, retention time 2.54 min., condition 4 for high performance liquid chromatography)
Ethyl Acetate Solution 2:
Optical purity: 94.7% ee (detection wavelength 205 nm, retention time 2.54 min., condition 4 for high performance liquid chromatography)

2) Two types of ethyl acetate solution prepared in Example 9 were left to stand at room temperature for 5 days, and were analyzed with HPLC.
Ethyl Acetate Solution 1:
Optical purity: 85.6% ee (detection wavelength 205 nm, retention time 2.56 min., condition 4 for high performance liquid chromatography)
Ethyl Acetate Solution 2:
Optical purity: 88.9% ee (detection wavelength 205 nm, retention time 2.55 min., condition 4 for high performance liquid chromatography)

3) Two types of ethyl acetate solution prepared in Example 9 were left to stand at room temperature for 10 days, and were analyzed with HPLC.
Ethyl Acetate Solution 1:
Optical purity: 76.8% ee (detection wavelength 205 nm, retention time 2.55 min., condition 4 for high performance liquid chromatography)
Ethyl Acetate Solution 2:
Optical purity: 82.9% ee (detection wavelength 205 nm, retention time 2.54 min., condition 4 for high performance liquid chromatography)

Example 11: D-Fmoc-Ser(n-Pr)—OH

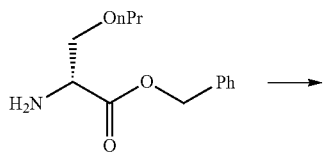

-continued

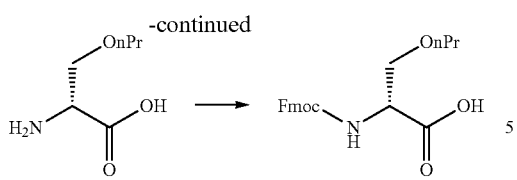

1) To the other part of the ethyl acetate solution 1, which was produced in Example 9 and divided into two, a mixture of 10% palladium on carbon 0.15 g and methanol 5 mL was added, and the reaction mixture was stirred under hydrogen gas atmosphere at room temperature for 2 hours. Palladium catalyst was filtered out using Celite under reduced pressure, and the mixture obtained was concentrated under reduced pressure to give D-H-Ser(n-Pr)—OH 854 mg as a crude product.

2) To a solution consisting of D-H-Ser(n-Pr)—OH 845 mg, water 8 mL, and sodium carbonate 0.40 g (3.77 mmol) cooled to 0° C., a solution consisting of FmocOSu 337 mg (1.00 mmol) and acetonitrile 8 mL was added dropwise over 5 minutes. The reaction mixture was stirred at room temperature for 3 hours, 1N-hydrochloric acid 8 mL was added thereto, and after a precipitate appeared, the reaction mixture was stirred at room temperature for 1 hour and 20 minutes. To the reaction mixture, 0.1N-hydrochloric acid 2 mL was added, and the mixture was stirred for additional 1 hour and 20 minutes, and then the precipitate was collected by filtration under reduced pressure. The crystals obtained were dried under reduced pressure to give D-Fmoc-Ser(n-Pr)—OH 3.60 g (yield: 58.4% in 3 steps) as white crystals.

D-Fmoc-Ser(n-Pr)—OH

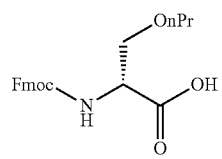

Optical purity: 99.9% ee (detection wavelength 205 nm, retention time 3.12 min., condition 3 for high performance liquid chromatography)

UV intensity ratio: 97.3% (detection wavelength 205 nm, retention time 2.74 min., condition 2 for high performance liquid chromatography)

$^1$H-NMR (DMSO-d6, 400 MHz) δ: 0.84 (3H, t, J=7.2), 1.42-1.56 (2H, m), 3.28-3.42 (2H, m), 3.56-3.70 (2H, m), 4.16-4.34 (4H, m), 7.32 (2H, dt, J=7.2, 0.8), 7.42 (2H, t, J=7.6), 7.61 (1H, d, J=8.0), 7.74 (2H, d, J=7.8), 7.89 (2H, d, J=7.6), 12.76 (1H, brs)

Example 12: D-Fmoc-Ser(i-Pr)—OH

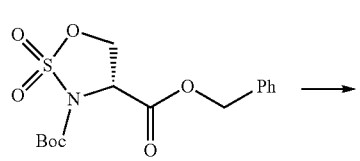

-continued

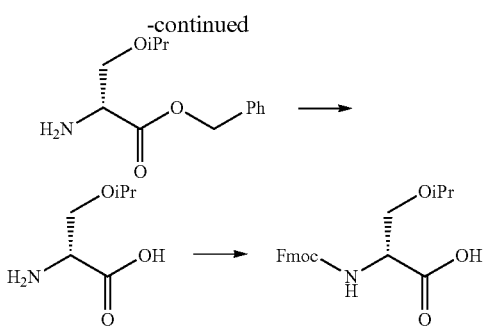

1) A mixture consisting of benzyl (4R)-5-t-butoxycarbonyl-1,2,5-sulfamidatecarboxylate 50 mg (0.14 mmol) and 2-propanol 1 mL was stirred for 30 hours while heating at 80° C. To the reaction mixture, ethyl acetate 1 mL, 5% aqueous sodium hydrogen carbonate 0.5 mL, and 10% brine 0.5 mL were added, and the organic layer and the aqueous layer were separated. The organic layer was obtained as an ethyl acetate solution of D-H-Ser(i-Pr)-OBzl.

D-H-Ser(i-Pr)-OBzl

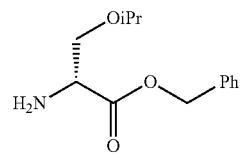 [SMILES: CC(C)OC[C@@H](N)C(=O)OCc1ccccc1]

Optical purity: 99.9% ee (detection wavelength 205 nm, retention time 2.21 min., condition 4 for high performance liquid chromatography)

UV intensity ratio: 78.5% (detection wavelength 205 nm, retention time 1.36 min., condition 2 for high performance liquid chromatography)

2) To a solution of D-H-Ser(i-Pr)-OBzl in ethyl acetate, a mixture of 10% palladium on carbon 15 mg and methanol 1 mL was added, and the reaction mixture was stirred under hydrogen gas atmosphere at room temperature for 1 hour. Palladium catalyst was filtered out using Celite under reduced pressure, and the mixture obtained was concentrated under reduced pressure to give D-H-Ser(i-Pr)—OH 27 mg as a crude product.

3) To a solution consisting of D-H-Ser(i-Pr)—OH 27 mg, water 0.5 mL, and sodium carbonate 25 mg (0.235 mmol) cooled to 0° C., a solution consisting of FmocOSu 33 mg (0.098 mmol) and acetonitrile 0.5 mL was added dropwise over 2 minutes. The reaction mixture was stirred at room temperature for 5 hours, 1N-hydrochloric acid 10 mL was added thereto over 5 minutes, and after a precipitate appeared, the reaction mixture was stirred at room temperature for 2 hours, and analyzed with HPLC.

D-Fmoc-Ser(i-Pr)—OH

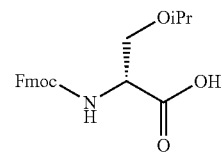

Example 13: D-H-Ser(2-hydroxy-2-methylpropyl)-OBzl

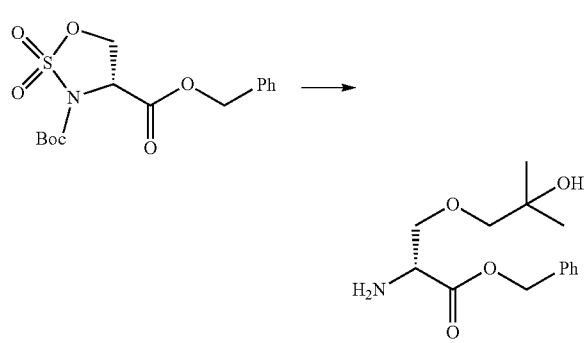

A mixture consisting of benzyl (4R)-5-t-butoxycarbonyl-1,2,5-sulfamidatecarboxylate 50 mg (0.14 mmol) and 2-methylpropane-1,2-diol 1 mL was stirred for 30 hours while heating at 80° C., and the reaction mixture was analyzed with HPLC.

D-H-Ser(2-hydroxy-2-methylpropyl)-OBzl

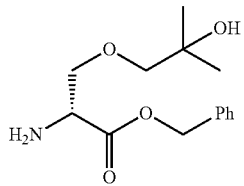 [SMILES: CC(C)(O)COC[C@@H](N)C(=O)OCc1ccccc1]

Optical purity: 99.9% ee (detection wavelength 205 nm, retention time 2.16 min., condition 4 for high performance liquid chromatography)

UV intensity ratio: 73.4% (detection wavelength 205 nm, retention time 1.22 min., condition 2 for high performance liquid chromatography)

Production example using Fmoc-Ser-OBzl as a starting material

Example 14: benzyl (4S)-5-(9-fluorenyl)methoxycarbonyl-1,2,5-sulfamidate-4-carboxylate

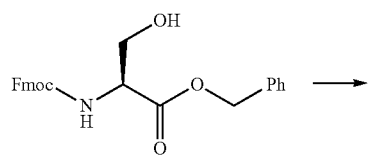

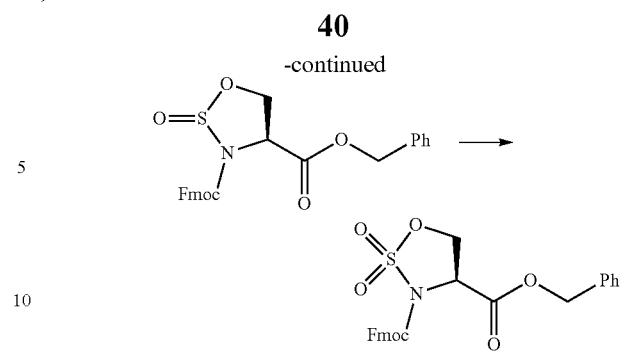

1) To a solution consisting of thionyl chloride 14.3 g (120 mmol) and ethyl acetate 350 mL cooled to −15° C., a solution consisting of Fmoc-Ser-OBzl 25 g (60 mmol) and ethyl acetate 100 mL was added dropwise over 10 minutes. The reaction mixture was stirred at the same temperature for 5 minutes, and then pyridine 23.7 g (300 mmol) was added dropwise over 10 minutes. The reaction mixture was stirred at the same temperature for 5 minutes, and then at room temperature for 24 hours. To the reaction mixture, water 200 mL was added, and the organic layer and the aqueous layer were separated. The organic layer obtained was washed with 1N-hydrochloric acid 200 mL and 10% brine 200 mL, and concentrated under reduced pressure to give a crude product of benzyl (4S)-5-(9-fluorenyl)methoxycarbonyl-1,2,5-sulfamiditecarboxylate 28.0 g as a diastereomeric mixture.

2) To a solution consisting of the crude product of benzyl (4S)-5-(9-fluorenyl)methoxycarbonyl-1,2,5-sulfamiditecarboxylate 28.0 g and acetonitrile 200 mL cooled to −10° C., a solution consisting of sodium periodate 19.3 g (90 mmol), ruthenium chloride hydrate 0.12 g (0.6 mmol), and water 300 mL was added dropwise over 15 minutes. The reaction mixture was stirred at the same temperature for 15 minutes, and then at room temperature for 23 hours. To the reaction mixture, water 100 mL and ethyl acetate 300 mL were added, and the organic layer and the aqueous layer were separated. The organic layer obtained was washed with 10% brine 200 mL, and concentrated under reduced pressure to give benzyl (4S)-5-(9-fluorenyl)methoxycarbonyl-1,2,5-sulfamidatecarboxylate 28.7 g as a crude product.

3) The crude product obtained was purified with silica gel column chromatography (elution solvent: ethyl acetate-hexane) to give benzyl (4S)-5-(9-fluorenyl)methoxycarbonyl-1,2,5-sulfamidatecarboxylate 15.2 g (yield: 53.0% in 2 steps) as a white powder.

Benzyl (4S)-5-(9-fluorenyl)methoxycarbonyl-1,2,5-sulfamidate-4-carboxylate

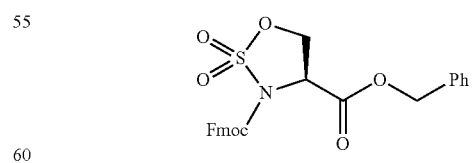

Optical purity: 99.9% ee (detection wavelength 205 nm, retention time 4.02 min., condition 3 for high performance liquid chromatography)

UV intensity ratio: 95.2% (detection wavelength 205 nm, retention time 3.31 min., condition 2 for high performance liquid chromatography)

1H-NMR (CDCl3, 400 MHz) δ: 4.22-4.34 (1H, m), 4.46 (1H, dd, J=10.4, 7.2), 4.58 (1H, dd, J=10.4, 7.2), 4.70-4.96 (3H, m), 5.20-5.32 (2H, m), 7.28-7.38 (7H, m), 7.42 (2H, t, J=7.6), 7.62-7.80 (4H, m)

Example 15: Fmoc-Ser(i-Pr)-OBzl (with sodium dihydrogenphosphate

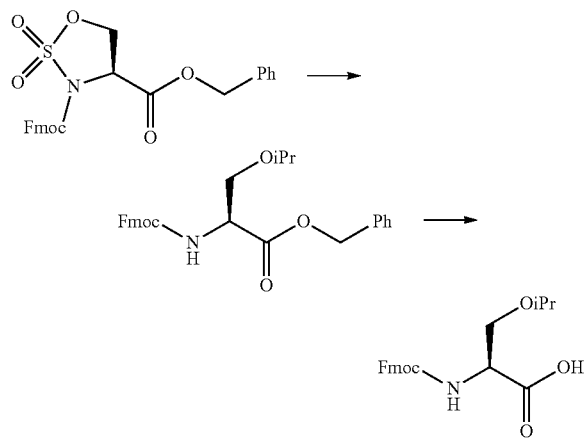

1) A mixture consisting of benzyl (4S)-5-(9-fluorenyl) methoxycarbonyl-1,2,5-sulfamidatecarboxylate 1.00 g (2.0 mmol), sodium dihydrogenphosphate 1.00 g, 2-propanol 4 mL, and 2,2,2-trifluoroethanol 2 mL was stirred for 6 hours while heating at 70° C. To the reaction mixture, ethyl acetate 20 mL and 10% brine 20 mL were added, and the organic layer and the aqueous layer were separated. The organic layer was obtained as an ethyl acetate solution of Fmoc-Ser (i-Pr)-OBzl.

Fmoc-Ser(i-Pr)-OBzl

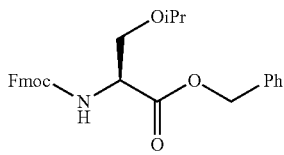

UV intensity ratio: 82.4% (detection wavelength 205 nm, retention time 3.54 min., condition 2 for high performance liquid chromatography)

Fmoc-Ser(i-Pr)—O(i-Pr)

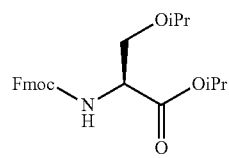

UV intensity ratio: 1.0% (detection wavelength 205 nm, retention time 3.41 min., condition 2 for high performance liquid chromatography)

Fmoc-Ser-OBzl

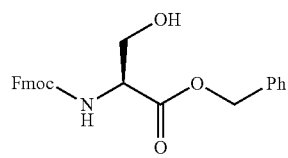

UV intensity ratio: 7.7% (detection wavelength 205 nm, retention time 2.87 min., condition 2 for high performance liquid chromatography)

The objective compound was produced in 82.4%, and Fmoc-Ser-OBzl that resulted from ring-opening of the sulfamidate without reaction with 2-propanol was produced in 7.7%. When an acid salt (in this case sodium dihydrogenphosphate) was used, the production of the byproduct was decreased by nearly 3 times compared to Example 16 in which the same starting material was used but an acid salt was not used.

2) To an ethyl acetate solution of Fmoc-Ser(i-Pr)—OBzl, a mixture of 10% palladium on carbon 0.10 g and methanol 4 mL was added, and the reaction mixture was stirred under hydrogen gas atmosphere at room temperature for 1 hour and 30 minutes. Palladium catalyst was filtered out using Celite under reduced pressure, and the mixture obtained was concentrated under reduced pressure to give Fmoc-Ser(i-Pr)—OH 0.80 g as a crude product.

Fmoc-Ser(i-Pr)—OH

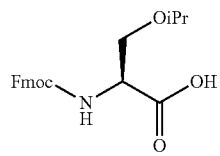

UV intensity ratio: 77.8% (detection wavelength 205 nm, retention time 2.70 min., condition 2 for high performance liquid chromatography)

3) A solution consisting of Fmoc-Ser(i-Pr)—OH 0.80 g, water 6 mL, sodium carbonate 0.30 g (2.8 mmol), and acetonitrile 2 mL was stirred at room temperature for 3 hours, and to the reaction mixture, ethyl acetate 5 mL was added, and the organic layer and the aqueous layer were separated. The aqueous layer was obtained as an aqueous solution of Fmoc-Ser(i-Pr)—OH. To the aqueous solution of Fmoc-Ser(i-Pr)—OH obtained, 1N-hydrochloric acid 6 mL was added, and after a precipitate appeared, the reaction mixture was stirred at room temperature for 4 hours. The precipitate was collected by filtration under reduced pressure, and the wet powder obtained was analyzed with HPLC.

Fmoc-Ser(i-Pr)—OH

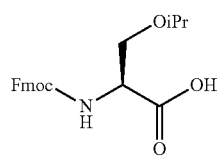

Optical purity: 99.9% ee (detection wavelength 205 nm, retention time 3.25 min., condition 3 for high performance liquid chromatography)

UV intensity ratio: 87.0% (detection wavelength 205 nm, retention time 2.70 min., condition 2 for high performance liquid chromatography)

Example 16: Fmoc-Ser(i-Pr)—OBzl (without sodium dihydrogenphosphate

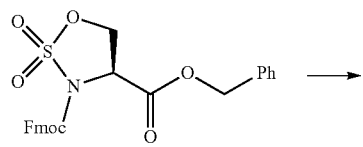

A mixture consisting of benzyl (4S)-5-(9-fluorenyl)methoxycarbonyl-1,2,5-sulfamidatecarboxylate 50 mg (0.10 mmol) and 2-propanol 0.30 mL was stirred for 2 hours while heating at 80° C., and the reaction mixture was analyzed with HPLC.

Fmoc-Ser(i-Pr)—OBzl

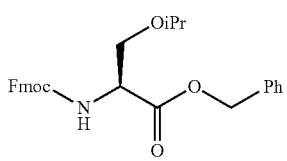

UV intensity ratio: 70.1% (detection wavelength 205 nm, retention time 3.53 min., condition 2 for high performance liquid chromatography)

Fmoc-Ser(i-Pr)—O(i-Pr)

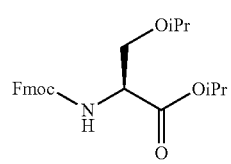

UV intensity ratio: 1.93% (detection wavelength 205 nm, retention time 3.42 min., condition 2 for high performance liquid chromatography)

Fmoc-Ser-OBzl

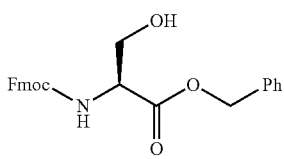

UV intensity ratio: 21.6% (detection wavelength 205 nm, retention time 2.87 min., condition 2 for high performance liquid chromatography)

Example 17: Fmoc-Ser(n-Pr)—OBzl (with sodium dihydrogenphosphate

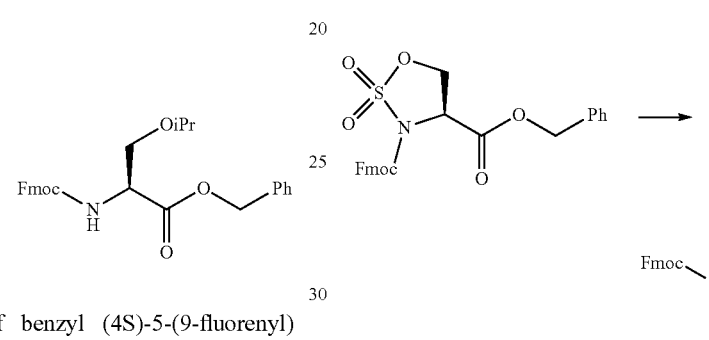

A mixture consisting of benzyl (4S)-5-(9-fluorenyl)methoxycarbonyl-1,2,5-sulfamidatecarboxylate 50 mg (0.10 mmol), sodium dihydrogenphosphate 24 mg, 1-propanol 0.20 mL, and 2,2,2-trifluoroethanol 0.10 mL was stirred for 2 hours while heating at 70° C., and the reaction mixture was analyzed with HPLC.

Fmoc-Ser(n-Pr)—OBzl

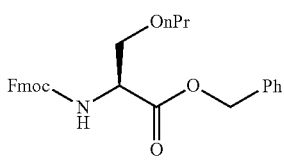

UV intensity ratio: 81.3% (detection wavelength 205 nm, retention time 3.56 min., condition 2 for high performance liquid chromatography)

Fmoc-Ser(n-Pr)—O(n-Pr)

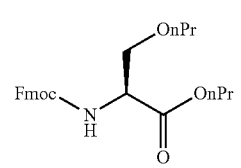

UV intensity ratio: 1.4% (detection wavelength 205 nm, retention time 3.46 min., condition 2 for high performance liquid chromatography)

Fmoc-Ser-OBzl

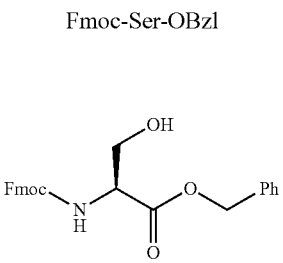

UV intensity ratio: 3.5% (detection wavelength 205 nm, retention time 2.87 min., condition 2 for high performance liquid chromatography)

The objective compound was produced in 81.3%, and a byproduct (Fmoc-Ser(n-Pr)—O(n-Pr)) that resulted from the additional reaction of the objective compound with 1-propanol to cause transesterification was produced in 1.4%. When an acid salt (in this case sodium dihydrogenphosphate) was used, the yield of the objective compound was improved by nearly 10%, and the production of the byproduct was decreased by nearly 6 times compared to Example 18 in which the same starting material was used but an acid salt was not used to perform the reaction.

Example 18: Fmoc-Ser(n-Pr)—OBzl (without sodium dihydrogenphosphate

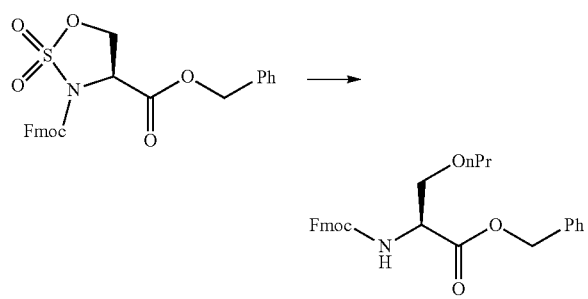

A mixture consisting of benzyl (4S)-5-(9-fluorenyl)methoxycarbonyl-1,2,5-sulfamidatecarboxylate 0.59 g (1.23 mmol), 1-propanol 2.4 mL, and 2,2,2-trifluoroethanol 1.2 mL was stirred for 2 hours while heating at 70° C., and the reaction mixture was analyzed with HPLC.

Fmoc-Ser(n-Pr)—OBzl

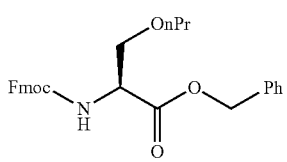

UV intensity ratio: 68.2% (detection wavelength 205 nm, retention time 3.56 min., condition 2 for high performance liquid chromatography)

Fmoc-Ser(n-Pr)—O(n-Pr)

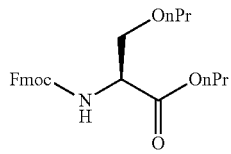

UV intensity ratio: 8.0% (detection wavelength 205 nm, retention time 3.46 min., condition 2 for high performance liquid chromatography)

Fmoc-Ser-OBzl

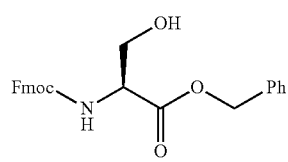

UV intensity ratio: 4.1% (detection wavelength 205 nm, retention time 2.87 min., condition 2 for high performance liquid chromatography)

Example 19:
Fmoc-Ser(2-hydroxy-2-methylpropyl)-OBzl (without sodium dihydrogenphosphate

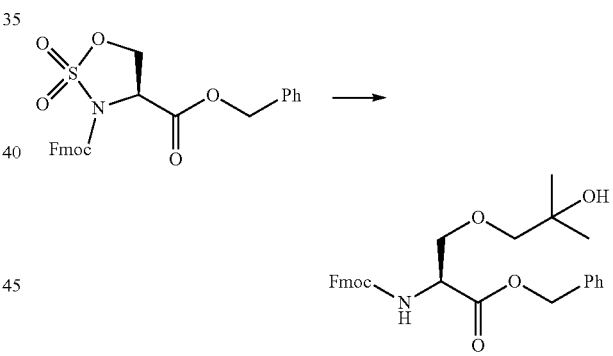

A mixture consisting of benzyl (4S)-5-(9-fluorenyl)methoxycarbonyl-1,2,5-sulfamidatecarboxylate 0.59 g (1.23 mmol), 2-methylpropane-1,2-diol 2.4 mL, and 2,2,2-trifluoroethanol 1.2 mL was stirred for 4 hours while heating at 70° C., and the reaction mixture was analyzed with HPLC.

Fmoc-Ser(2-hydroxy-2-methylpropyl)-OBzl

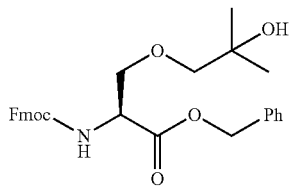

UV intensity ratio: 42.8% (detection wavelength 205 nm, retention time 3.09 min., condition 2 for high performance liquid chromatography)

Fmoc-Ser(2-hydroxy-2-methylpropyl)-OH

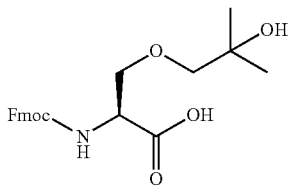

UV intensity ratio: 11.3% (detection wavelength 205 nm, retention time 2.31 min., condition 2 for high performance liquid chromatography)

Fmoc-Ser-OBzl

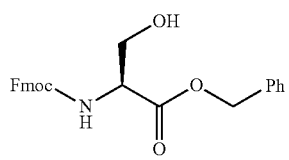

UV intensity ratio: 20.0% (detection wavelength 205 nm, retention time 2.87 min., condition 2 for high performance liquid chromatography)

Fmoc-Ser-OH

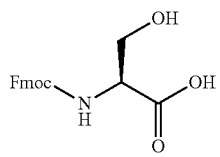

UV intensity ratio: 3.8% (detection wavelength 205 nm, retention time 2.08 min., condition 2 for high performance liquid chromatography)

Example 20: Fmoc-Ala(Cl)-OBzl

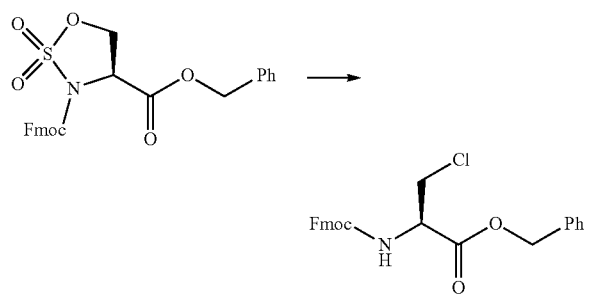

A mixture consisting of benzyl (4S)-5-(9-fluorenyl)methoxycarbonyl-1,2,5-sulfamidatecarboxylate 50 mg (0.1 mmol), pyridine hydrochloride 23 mg (0.2 mmol), 1-propanol 0.20 mL, and 2,2,2-trifluoroethanol 0.10 mL was stirred for 1 hour while heating at 70° C., and the reaction mixture was analyzed with HPLC.

Fmoc-Ala(Cl)—OBzl

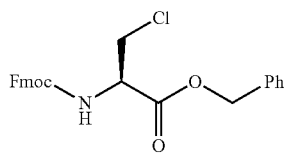

UV intensity ratio: 91.5% (detection wavelength 205 nm, retention time 3.36 min., condition 2 for high performance liquid chromatography)

ESI (LC/MS positive mode) m/z: 436.41 (M+H$^+$)

When pyridine hydrochloride was used as an acid salt, the starting material did not react with 1-propanol, and the chlorinated compound (Fmoc-Ala(Cl)—OBzl) that was ring-opened with chloride ion derived from pyridine hydrochloride was obtained. When sodium dihydrogenphosphate was used as an acid salt, the objective compound was found to be produced efficiently.

Production example using Fmoc-Ser-Ot-Bu as a starting material

Example 21: t-Butyl (4S)-5-(9-fluorenyl)methoxycarbonyl-1,2,5-sulfamidate-4-carboxylate

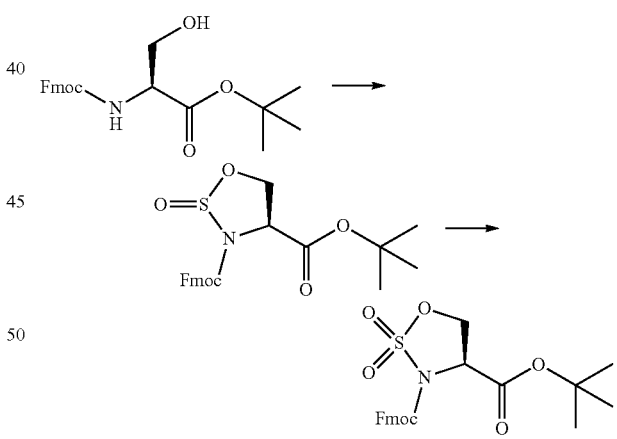

1) To a solution consisting of thionyl chloride 1.61 g (13.5 mmol) and dichloromethane 20 mL cooled to −40° C., a solution consisting of Fmoc-Ser-Ot-Bu 2.00 g (5.2 mmol) and dichloromethane 5 mL was added dropwise over 5 minutes. The reaction mixture was stirred at the same temperature for 15 minutes, and then pyridine 2.68 g (33.8 mmol) was added dropwise over 5 minutes. The reaction mixture was stirred at the same temperature for 20 minutes, then at 0° C. for 20 minutes and at room temperature for 1 hour and 30 minutes. To the reaction mixture, water 30 mL was added, and the organic layer and the aqueous layer were separated. To the aqueous layer obtained, dichloromethane 20 mL was added, and the organic layer and the aqueous layer were separated again. The organic layers obtained were combined, washed with 5% NaHCO$_3$ 30 mL and 10% brine 30 mL, and then concentrated under reduced pressure to give a crude product of t-butyl (4S)-5-(9-fluorenyl) methoxycarbonyl-1,2,5-sulfamiditecarboxylate 2.22 g as a diastereomeric mixture.

2) To a solution consisting of the crude product of t-butyl (4S)-5-(9-fluorenyl)methoxycarbonyl-1,2,5-sulfamiditecarboxylate 2.22 g and acetonitrile 30 mL cooled to 0° C., a solution consisting of sodium periodate 1.67 g (7.8 mmol), ruthenium chloride hydrate 11 mg (0.05 mmol), and water 30 mL was added dropwise over 5 minutes. The reaction mixture was stirred at the same temperature for 1 hour and 30 minutes, and then at room temperature for 20 minutes. To the reaction mixture, 5% NaHCO$_3$ 60 mL, water 60 mL, and ethyl acetate 40 mL were added, and the organic layer and the aqueous layer were separated. To the aqueous layer obtained, ethyl acetate 40 mL was added, and the organic layer and the aqueous layer were separated again. The organic layers obtained were combined, washed with 10% brine 30 mL, and then concentrated under reduced pressure to give t-butyl (4S)-5-(9-fluorenyl)methoxycarbonyl-1,2,5-sulfamidatecarboxylate 2.25 g as a crude product.

3) The crude product obtained was purified with silica gel column chromatography (elution solvent: ethyl acetate-hexane) to give t-butyl (4S)-5-(9-fluorenyl)methoxycarbonyl-1,2,5-sulfamidatecarboxylate 1.87 g (yield: 83.9% in 2 steps) as a white powder.

T-Butyl (4S)-5-(9-fluorenyl)methoxycarbonyl-1,2,5-sulfamidatecarboxylate

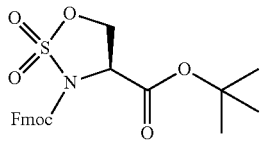

UV intensity ratio: 96.9% (detection wavelength 205 nm, retention time 3.24 min., condition 1 for high performance liquid chromatography)

1H-NMR (CDCl3, 400 MHz) δ: 1.50 (9H, s), 4.35 (1H, t, J=7.6), 4.48 (1H, dd, J=10.4, 7.6), 4.61 (1H, dd, J=10.4, 7.6), 4.70-4.88 (3H, m), 7.31-7.37 (2H, m), 7.39-7.45 (2H, m), 7.58-7.80 (4H, m)

ESI (LC/MS negative mode) m/z: 444.33 (M−H+)

Production example using H-MeSer-OBzl as a starting material

Example 22: Benzyl (4S)-5-methyl-1,2,5-sulfamidate-4-carboxylate

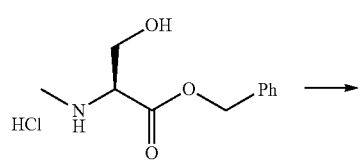

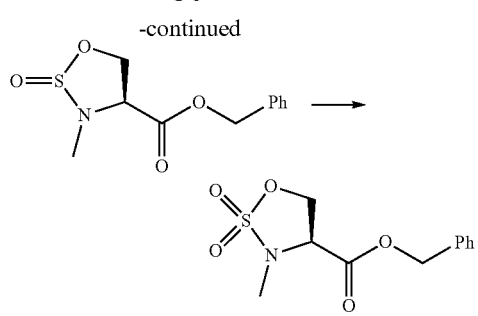

1) To a solution consisting of thionyl chloride 2.38 g (20 mmol) and dichloromethane 50 mL cooled to −15° C., H-MeSer-OBzl hydrochloride 2.50 g (10 mmol) was added. The reaction mixture was stirred at the same temperature for 5 minutes, and then pyridine 4.75 g (60 mmol) was added dropwise over 5 minutes. The reaction mixture was stirred at the same temperature for 5 minutes, and then at room temperature for 1 hour. To the reaction mixture, water 25 mL was added, and the organic layer and the aqueous layer were separated. The organic layer obtained was washed with 1N-hydrochloric acid 25 mL and 10% brine 25 mL, and then concentrated under reduced pressure to give a crude product of benzyl (4S)-5-methyl-1,2,5-sulfamiditecarboxylate 2.06 g as a diastereomeric mixture.

2) To a solution consisting of the crude product of benzyl (4S)-5-methyl-1,2,5-sulfamiditecarboxylate 2.06 g and acetonitrile 20 mL cooled to −5° C., a solution consisting of sodium periodate 3.21 g (15 mmol), ruthenium chloride hydrate 62 mg (0.3 mmol), and water 30 mL was added dropwise over 5 minutes. The reaction mixture was stirred at the same temperature for 5 minutes, and then at room temperature for 30 minutes. To the reaction mixture, water 20 mL and ethyl acetate 40 mL were added, and the organic layer and the aqueous layer were separated. The organic layer obtained was washed with 10% brine 20 mL, and then concentrated under reduced pressure to give benzyl 5-methyl-1,2,5-sulfamidatecarboxylate 1.87 g as a crude product.

3) A mixture consisting of the crude product obtained and ethyl acetate 4 mL was heated to 40° C., hexane 12 mL was added thereto, and after a precipitate appeared, the reaction mixture was stirred at room temperature for 50 minutes, and the precipitate was collected by filtration under reduced pressure. The crystals obtained were dried under reduced pressure to give benzyl (4S)-5-methyl-1,2,5-sulfamidatecarboxylate 1.14 g (yield: 42.0% in 2 steps) as pale yellow crystals.

Optical purity: 99.9% ee (detection wavelength 205 nm, retention time 2.58 min., condition 3 for high performance liquid chromatography)

Benzyl (4S)-5-methyl-1,2,5-sulfamidatecarboxylate

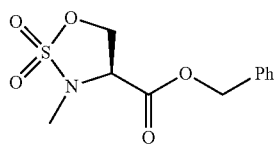 [SMILES: CN1[C@H](C(=O)OCc2ccccc2)COS1(=O)=O]

UV intensity ratio: 96.3% (detection wavelength 205 nm, retention time 2.29 min., condition 2 for high performance liquid chromatography)

$^1$H-NMR (CDCl$_3$, 400 MHz) δ: 2.95 (3H, s), 4.10 (1H, dd, J=7.6, 6.4), 4.60-4.72 (2H, m), 5.24 (1H, d, J=12.0), 5.28 (1H, d, J=12.0), 7.32-7.44 (5H, m)

Example 23: H-MeSer(n-Pr)—OBzl

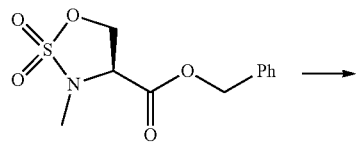

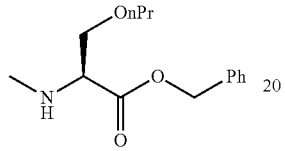

A mixture consisting of benzyl (4S)-5-methyl-1,2,5-sulfamidatecarboxylate 0.28 g (1.0 mmol) and 2-propanol 5.6 mL was stirred for 13 hours while heating at 90° C. To the reaction mixture, dichloromethane 16.4 mL and 5% aqueous sodium hydrogen carbonate 16.4 mL were added, and the organic layer and the aqueous layer were separated. The organic layer was obtained as an ethyl acetate solution of H-MeSer(n-Pr)—OBzl, and analyzed with HPLC.

UV intensity ratio: 91.8% (detection wavelength 205 nm, retention time 1.65 min., condition 1 for high performance liquid chromatography)

ESI (LC/MS positive mode) m/z: 252.48 (M+H$^+$)

Example 24: Fmoc-Ser(CH$_2$CH(OH)CF$_3$)—OH (with sodium dihydrogenphosphate

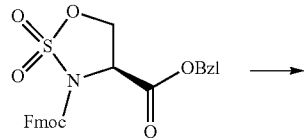

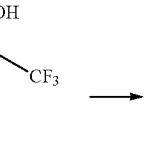

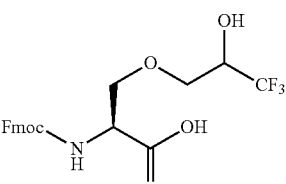

1) A mixture consisting of benzyl (4S)-5-(9-fluorenyl)methoxycarbonyl-1,2,5-sulfamidatecarboxylate 100 mg (0.208 mmol), sodium dihydrogenphosphate 100 mg (0.717 mmol), 3,3,3-trifluoropropane-1,2-diol 0.543 g (4.17 mmol), and 2,2,2-trifluoroethanol 0.2 mL was stirred for 48 hours while heating at 70° C. To the reaction mixture, ethyl acetate 1 mL and 2N aqueous hydrochloric acid 1 mL were added, and the organic layer and the aqueous layer were separated. Additional ethyl acetate 1 mL was added to the aqueous layer, and the organic layer and the aqueous layer were separated. The organic layers obtained were combined to give an ethyl acetate solution of Fmoc-Ser(CH$_2$CH(OH)CF$_3$)—OBzl.

Fmoc-Ser(CH$_2$CH(OH)CF$_3$)—OBzl

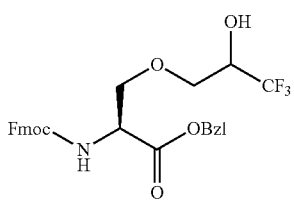

UV intensity ratio: 50.9% (detection wavelength 205 nm, retention time 3.24 min., condition 2 for high performance liquid chromatography)

ESI (LC/MS positive mode) m/z: 530.59 (M+H$^+$)

2) To an ethyl acetate solution of Fmoc-Ser(CH$_2$CH(OH)CF$_3$)—OBzl, 10% palladium on carbon 20 mg was added, and the reaction mixture was stirred under hydrogen gas atmosphere at room temperature for 3 hours to give Fmoc-Ser(CH$_2$CH(OH)CF$_3$)—OH as an ethyl acetate solution.

Fmoc-Ser(CH$_2$CH(OH)CF$_3$)—OH

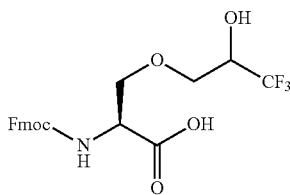

UV intensity ratio: 52.3% (detection wavelength 205 nm, retention time 2.52 min., condition 2 for high performance liquid chromatography)

ESI (LC/MS negative mode) m/z: 438.39 (M−H$^+$)

Example 25: Fmoc-Ser(Bzl)-OH (with sodium dihydrogenphosphate

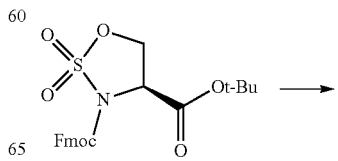

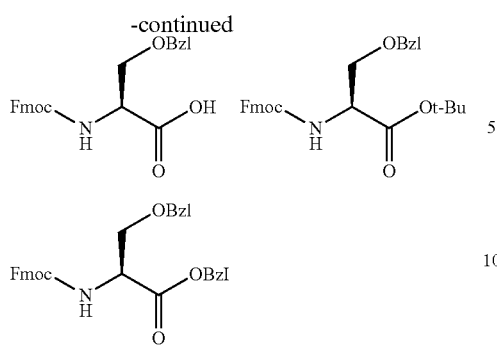

A mixture consisting of t-butyl (4S)-5-(9-fluorenyl) methoxycarbonyl-1,2,5-sulfamidatecarboxylate 50 mg (0.11 mmol), sodium dihydrogenphosphate 50 mg, and benzyl alcohol 0.30 mL (2.91 mmol) was stirred for 2 hours while heating at 90° C., and the reaction mixture was analyzed with HPLC.

Fmoc-Ser(Bzl)-OH

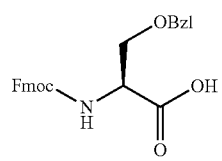

UV intensity ratio: 39.5% (detection wavelength 205 nm, retention time 2.93 min., condition 2 for high performance liquid chromatography)
ESI (LC/MS negative mode) m/z: 416.43 (M−H$^+$)

Fmoc-Ser(Bzl)-Ot-Bu

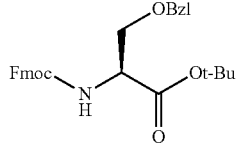

UV intensity ratio: 22.9% (detection wavelength 205 nm, retention time 3.72 min., condition 2 for high performance liquid chromatography)
ESI (LC/MS positive mode) m/z: 474.68 (M+H$^+$)

Fmoc-Ser(Bzl)-OBzl

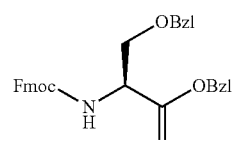

UV intensity ratio: 22.9% (detection wavelength 205 nm, retention time 3.65 min., condition 2 for high performance liquid chromatography)
ESI (LC/MS positive mode) m/z: 474.68 (M+H$^+$)

Example 26: Fmoc-Ser(CH$_2$-3F—C$_6$H$_4$)—OH (with sodium dihydrogenphosphate

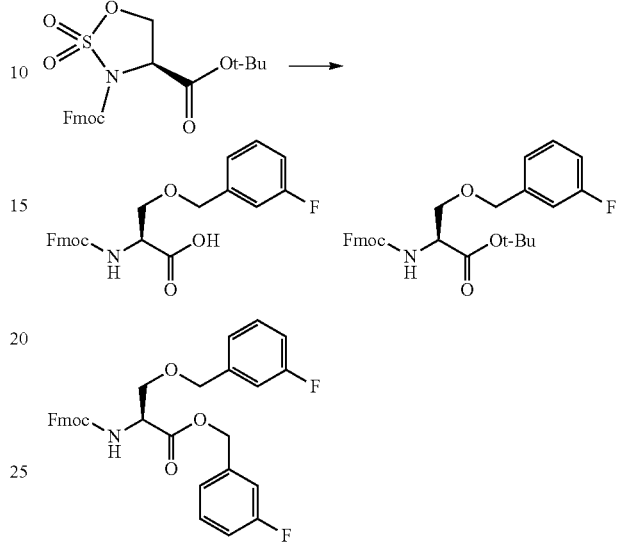

A mixture consisting of t-butyl (4S)-5-(9-fluorenyl) methoxycarbonyl-1,2,5-sulfamidatecarboxylate 50 mg (0.11 mmol), sodium dihydrogenphosphate 50 mg, and 3-fluorobenzyl alcohol 0.30 mL (2.78 mmol) was stirred for 2 hours while heating at 90° C., and the reaction mixture was analyzed with HPLC.

Fmoc-Ser(CH$_2$-3F—C$_6$H$_4$)—OH

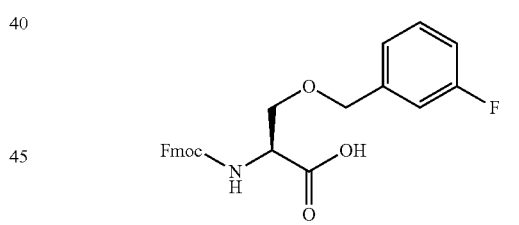

UV intensity ratio: 38.4% (detection wavelength 205 nm, retention time 2.95 min., condition 2 for high performance liquid chromatography)
ESI (LC/MS negative mode) m/z: 434.51 (M−H$^+$)

Fmoc-Ser(CH$_2$-3F—C$_6$H$_4$)-Ot-Bu

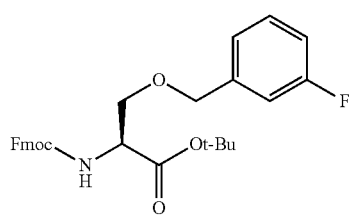

UV intensity ratio: 2.90% (detection wavelength 205 nm, retention time 3.71 min., condition 2 for high performance liquid chromatography)

ESI (LC/MS positive mode) m/z: 492.65 (M+H⁺)

Fmoc-Ser(CH₂-3F—C₆H₄)—OCH₂-3F—C₆H₄

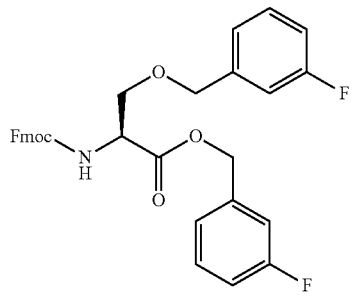

UV intensity ratio: 8.35% (detection wavelength 205 nm, retention time 3.71 min., condition 2 for high performance liquid chromatography)

ESI (LC/MS positive mode) m/z: 544.67 (M+H⁺)

Example 27: Fmoc-Ser(CH₂-2-thienyl)-OH (with sodium dihydrogenphosphate

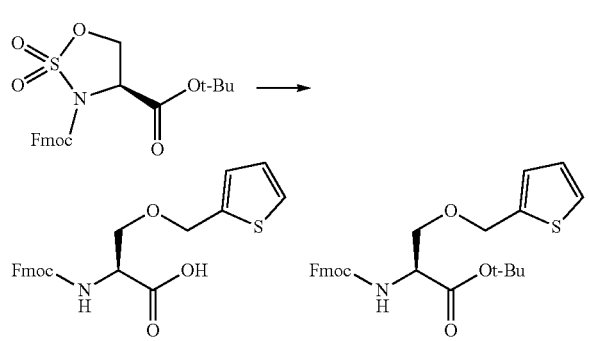

A mixture consisting of t-butyl (4S)-5-(9-fluorenyl)methoxycarbonyl-1,2,5-sulfamidatecarboxylate 45 mg (0.11 mmol), sodium dihydrogenphosphate 45 mg, and 2-thiophene methanol 0.27 mL (2.86 mmol) was stirred at room temperature for 48 hours, and the reaction mixture was analyzed with HPLC.

Fmoc-Ser(CH₂-2-thienyl)-OH

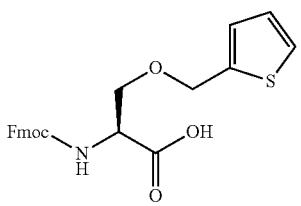

UV intensity ratio: 8.61% (detection wavelength 205 nm, retention time 2.85 min., condition 2 for high performance liquid chromatography)

ESI (LC/MS positive mode) m/z: 422.37 (M+H⁺)

Fmoc-Ser(CH₂-2-thienyl)-Ot-Bu

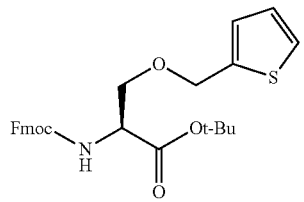

UV intensity ratio: 23.3% (detection wavelength 205 nm, retention time 3.63 min., condition 2 for high performance liquid chromatography)

ESI (LC/MS negative mode) m/z: 480.70 (M–H⁺)

Example 28: Fmoc-Ser(CH₂-2-furyl)-Ot-Bu (with sodium dihydrogenphosphate

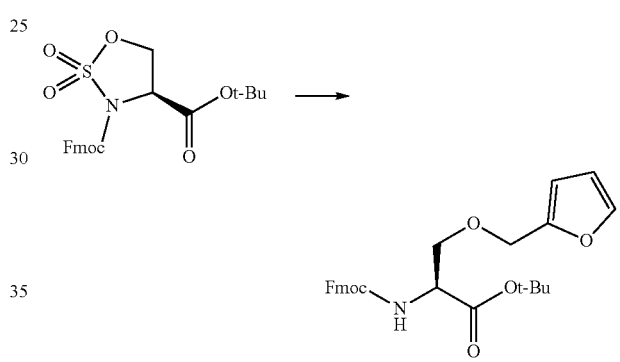

A mixture consisting of t-butyl (4S)-5-(9-fluorenyl)methoxycarbonyl-1,2,5-sulfamidatecarboxylate 45 mg (0.11 mmol), sodium dihydrogenphosphate 45 mg, and 2-furfuryl alcohol 0.27 mL (3.11 mmol) was stirred at room temperature for 48 hours, and the reaction mixture was analyzed with HPLC.

Fmoc-Ser(CH₂-2-furyl)-Ot-Bu

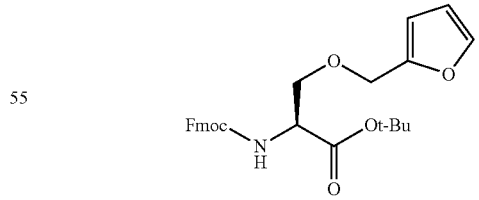

UV intensity ratio: 18.6% (detection wavelength 205 nm, retention time 3.49 min., condition 2 for high performance liquid chromatography)

ESI (LC/MS positive mode) m/z: 464.64 (M+H⁺)

Production example using Boc-homoSer-OBzl as a starting material

Example 29: Benzyl (4S)-3-t-butoxycarbonyl-2,2-dioxo-1,2,3-oxathiazinane-4-carboxylate

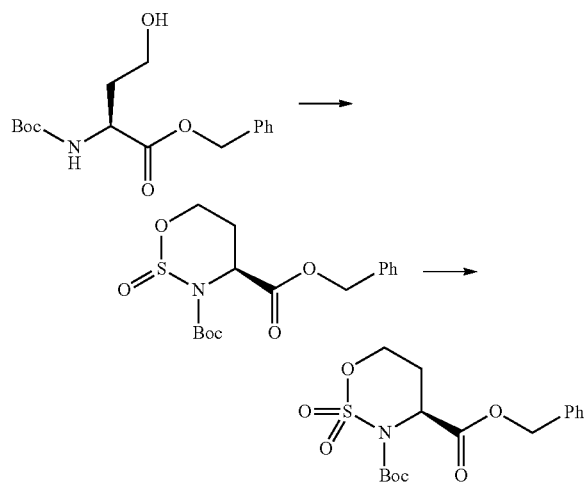

1) To a solution consisting of thionyl chloride 7.46 g (62.7 mmol) and ethyl acetate 200 mL cooled to −15° C., a solution consisting of Boc-homoSer-OBzl 10.00 g (31.3 mmol) and ethyl acetate 30 mL was added dropwise over 5 minutes. The reaction mixture was stirred at the same temperature for 5 minutes, and then pyridine 12.4 g (157 mmol) was added dropwise over 5 minutes. The reaction mixture was stirred at −15° C. for 5 minutes and then at room temperature for 3 hours. To the reaction mixture, water 100 mL was added, and the organic layer and the aqueous layer were separated. To the organic layer obtained, 1N HCl 100 mL was added, and the organic layer and the aqueous layer were separated again. The organic layer obtained was washed with 10% brine 100 mL, and then concentrated under reduced pressure to give benzyl (4S)-3-t-butoxycarbonyl-2-oxo-1,2,3-oxathiazinane-4-carboxylate 10.90 g as a crude product of a diastereomeric mixture.

2) To a solution consisting of the crude product of benzyl (4S)-3-t-butoxycarbonyl-2-oxo-1,2,3-oxathiazinane-4-carboxylate 10.90 g and acetonitrile 90 mL cooled to −10° C., a solution consisting of sodium periodate 10.05 g (47.0 mmol), ruthenium chloride hydrate 195 mg (0.94 mmol), and water 150 mL was added dropwise over 10 minutes. The reaction mixture was stirred at −10° C. for 15 minutes, and then at room temperature for 1 hour and 40 minutes. To the reaction mixture, water 50 mL and ethyl acetate 150 mL were added, and the organic layer and the aqueous layer were separated. To the aqueous layer obtained, ethyl acetate 40 mL was added, and the organic layer and the aqueous layer were separated again. The organic layer obtained was washed with a mixture consisting of 2N aqueous HCl 20 mL and 10% brine 200 mL, and then concentrated under reduced pressure to give benzyl (4S)-3-t-butoxycarbonyl-2,2-dioxo-1,2,3-oxathiazinane-4-carboxylate 6.72 g as a crude product.

3) The crude product obtained was purified with silica gel column chromatography (elution solvent: ethyl acetate-hexane) to give benzyl (4S)-3-t-butoxycarbonyl-2,2-dioxo-1,2,3-oxathiazinane-4-carboxylate 1.75 g (yield: 15.1% in 2 steps) as a white powder and (S)-Boc-Gly(2-chloroethyl)-OBzl 2.50 g (yield: 22.5% in 2 steps) as a pale yellow powder.

Benzyl (4S)-3-t-butoxycarbonyl-2,2-dioxo-1,2,3-oxathiazinane-4-carboxylate

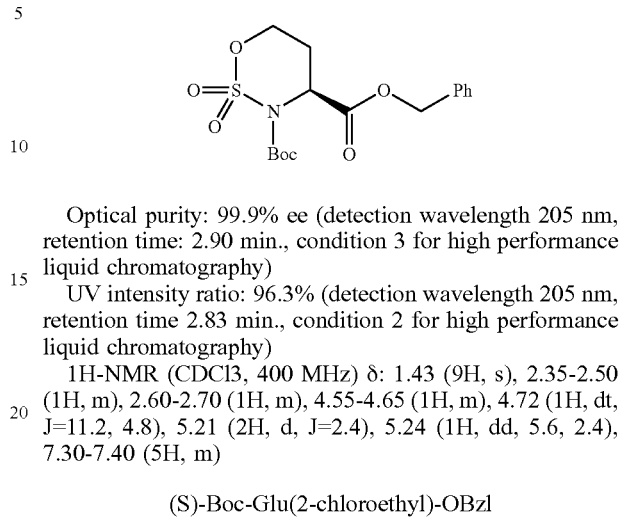

Optical purity: 99.9% ee (detection wavelength 205 nm, retention time: 2.90 min., condition 3 for high performance liquid chromatography)

UV intensity ratio: 96.3% (detection wavelength 205 nm, retention time 2.83 min., condition 2 for high performance liquid chromatography)

1H-NMR (CDCl3, 400 MHz) δ: 1.43 (9H, s), 2.35-2.50 (1H, m), 2.60-2.70 (1H, m), 4.55-4.65 (1H, m), 4.72 (1H, dt, J=11.2, 4.8), 5.21 (2H, d, J=2.4), 5.24 (1H, dd, 5.6, 2.4), 7.30-7.40 (5H, m)

(S)-Boc-Glu(2-chloroethyl)-OBzl

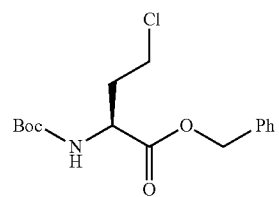 [SMILES: CC(C)(C)OC(=O)N[C@@H](CCCl)C(=O)OCc1ccccc1]

Optical purity: 99.9% ee (detection wavelength 205 nm, retention time: 3.07 min., condition 5 for high performance liquid chromatography)

UV intensity ratio: 98.3% (detection wavelength 205 nm, retention time 3.71 min., condition 2 for high performance liquid chromatography)

1H-NMR (CDCl3, 400 MHz) δ: 1.44 (9H, s), 2.08-2.20 (1H, m), 2.28-2.40 (1H, m), 3.57 (2H, t, 7.2), 4.43-4.53 (1H, m), 5.08-5.20 (1H, m), 4.18 (2H, dd, J=14.8, 12.0), 7.31-7.41 (5H, m)

ESI (LC/MS positive mode) m/z: 328.57, 330.55 (M+H+)

Example 30: H-homoSer(n-Pr)—OH

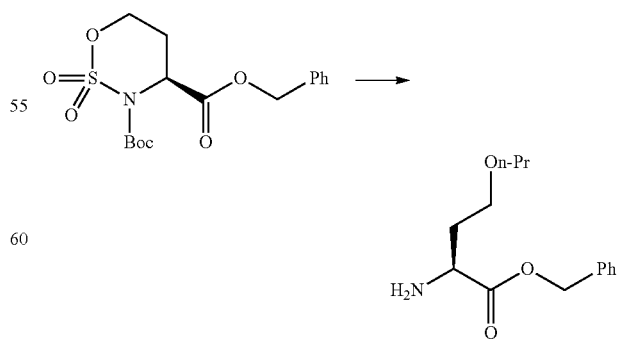

A mixture consisting of benzyl (4S)-3-t-butoxycarbonyl-2,2-dioxo-1,2,3-oxathiazinane-4-carboxylate 50 mg (0.134 mmol) and 1-propanol 1 mL was stirred for 40 hours while heating at 80° C., and the reaction mixture was analyzed with HPLC.

H-homoSer(n-Pr)—OBzl

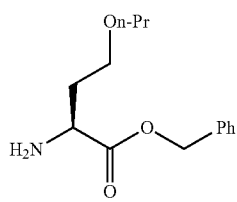

UV intensity ratio: 87.5% (detection wavelength 205 nm, retention time 1.50 min., condition 2 for high performance liquid chromatography)

ESI (LC/MS positive mode) m/z: 252.60 (M+H$^+$)

Example 31: H-homoSer(i-Pr)—OH

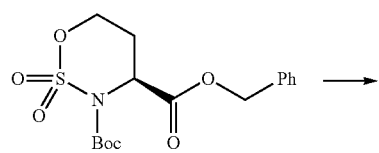

A mixture consisting of benzyl (4S)-3-t-butoxycarbonyl-2,2-dioxo-1,2,3-oxathiazinane-4-carboxylate 50 mg (0.134 mmol) and 2-propanol 1 mL was stirred for 40 hours while heating at 80° C., and the reaction mixture was analyzed with HPLC.

H-homoSer(i-Pr)—OBzl

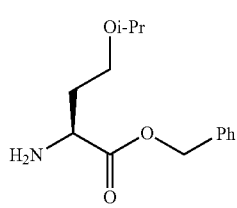

UV intensity ratio: 84.2% (detection wavelength 205 nm, retention time 1.47 min., condition 2 for high performance liquid chromatography)

ESI (LC/MS positive mode) m/z: 252.60 (M+H$^+$)

Example 32: H-homoSer(3-methylbutyl)-OBzl

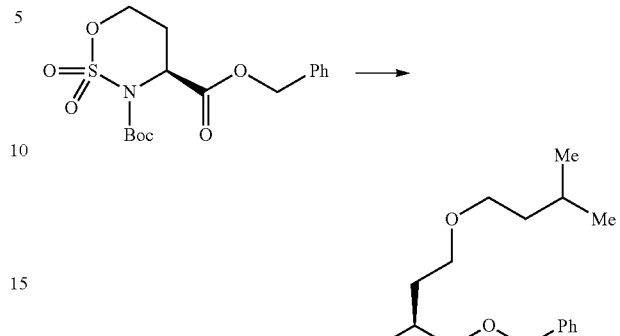

A mixture consisting of benzyl (4S)-3-t-butoxycarbonyl-2,2-dioxo-1,2,3-oxathiazinane-4-carboxylate 50 mg (0.134 mmol) and 3-methylbutanol 1 mL was stirred for 40 hours while heating at 80° C., and the reaction mixture was analyzed with HPLC.

H-homoSer(3-methylbutyl)-OBzl

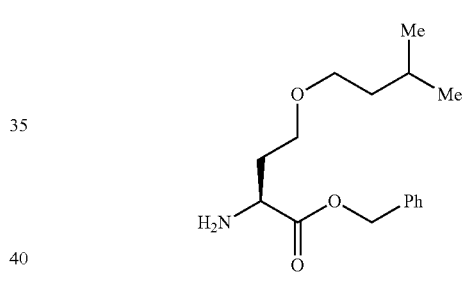

UV intensity ratio: 84.8% (detection wavelength 205 nm, retention time 1.84 min., condition 2 for high performance liquid chromatography)

ESI (LC/MS positive mode) m/z: 280.62 (M+H$^+$)

Example 33: H-homoSer(2-hydroxy-2-methylpropyl)-OBzl

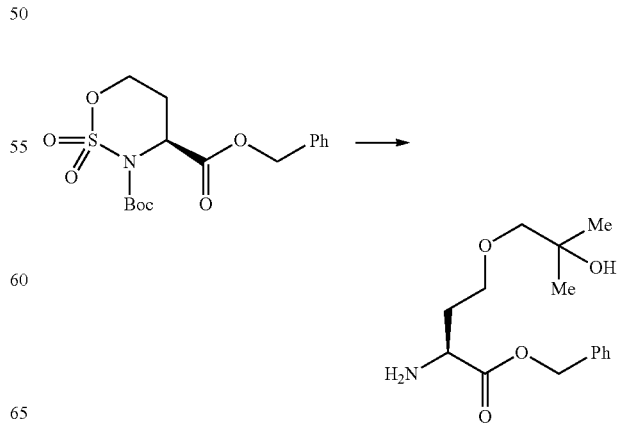

A mixture consisting of benzyl (4S)-3-t-butoxycarbonyl-2,2-dioxo-1,2,3-oxathiazinane-4-carboxylate 50 mg (0.134 mmol) and 2-methylpropane-1,2-diol 1 mL was stirred for 40 hours while heating at 80° C., and the reaction mixture was analyzed with HPLC.

H-homoSer(2-hydroxy-2-methylpropyl)-OBzl

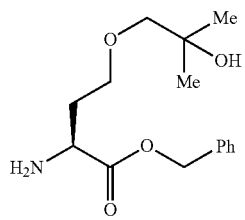 [SMILES: CC(C)(O)COCC[C@H](N)C(=O)OCc1ccccc1]

UV intensity ratio: 70.9% (detection wavelength 205 nm, retention time 1.29 min., condition 2 for high performance liquid chromatography)

ESI (LC/MS positive mode) m/z: 282.60 (M+H+)

Production example using Fmoc-Asp(Ot-Bu)-OL as a starting material

Example 34: t-Butyl (4S)-5-(9-fluorenyl)methoxy-carbonyl-1,2,5-sulfamidate-4-acetate

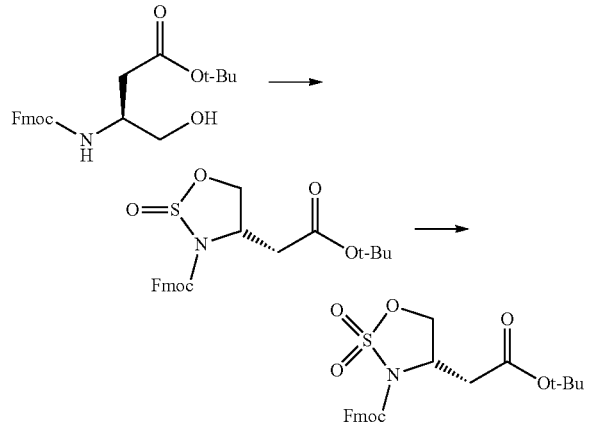

1) To a solution consisting of thionyl chloride 2.38 g (20.0 mmol) and ethyl acetate 80 mL cooled to −40° C., a solution consisting of Fmoc-Asp(Ot-Bu)-OL 4.00 g (10.0 mmol) and dichloromethane 12 mL was added dropwise over 5 minutes. The reaction mixture was stirred at the same temperature for 5 minutes, and then pyridine 3.96 g (50.0 mmol) was added dropwise over 5 minutes. The reaction mixture was stirred at −40° C. for 5 minutes and then at room temperature for 2 hours. To the reaction mixture, water 40 mL was added, and the organic layer and the aqueous layer were separated. To the organic layer obtained, 1N HCl 40 mL was added, and the organic layer and the aqueous layer were separated again. The organic layer obtained was washed with 10% brine 40 mL, and then concentrated under reduced pressure to give t-butyl (4R)-5-(9-fluorenyl)methoxycarbonyl-1,2,5-sulfamidite-4-acetate 4.65 g as a crude product of a diastereomeric mixture.

2) To a solution consisting of the crude product of t-butyl (4R)-5-(9-fluorenyl)methoxycarbonyl-1,2,5-sulfamidite-4-acetate 4.65 g and acetonitrile 20 mL cooled to −10° C., a solution consisting of sodium periodate 3.21 g (15.0 mmol), ruthenium chloride hydrate 21 mg (0.1 mmol), and water 60 mL was added dropwise over 10 minutes. The reaction mixture was stirred at −20° C. for 5 minutes, and then at room temperature for 3 hours. To the reaction mixture, sodium carbonate 1.20 g (11.3 mmol), water 60 mL, and ethyl acetate 90 mL were added, and the organic layer and the aqueous layer were separated. The organic layer obtained was washed with a mixture consisting of NaCl 6.00 g (102 mmol) and water 54 mL, and then concentrated under reduced pressure to give t-butyl (4S)-5-(9-fluorenyl)methoxycarbonyl-1,2,5-sulfamidate-4-acetate 4.31 g as a crude product.

T-Butyl (4S)-5-(9-fluorenyl)methoxycarbonyl-1,2,5-sulfamidate-4-acetate

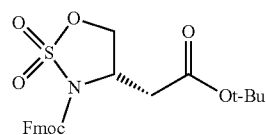

Optical purity: 99.9% ee (detection wavelength 205 nm, retention time: 3.63 min., condition 3 for high performance liquid chromatography)

UV intensity ratio: 79.2% (detection wavelength 205 nm, retention time 3.43 min., condition 2 for high performance liquid chromatography)

1H-NMR (CDCl3, 400 MHz) δ: 1.44 (9H, s), 2.68-2.80 (1H, m), 2.82-2.96 (1H, m), 4.33 (1H, t, J=7.2), 4.48-4.53 (4H, m), 4.81 (1H, dd, 9.6, 6.0), 7.31-7.45 (4H, m), 7.66-7.79 (4H, m)

ESI (LC/MS negative mode) m/z: 504.49 (M+HCO2−)

Example 35: (3S)-3-(9-Fluorenyl)methoxycarbonylamino-4-n-propoxybutyric acid (with sodium dihydrogenphosphate

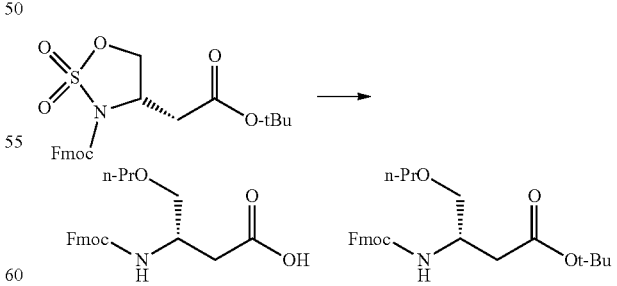

A mixture consisting of t-butyl (4S)-5-(9-fluorenyl)methoxycarbonyl-1,2,5-sulfamidate-4-acetate 50 mg (0.108 mmol), sodium dihydrogenphosphate 50 mg, and 1-propanol 1 mL was stirred for 2 hours while heating at 70° C., and the reaction mixture was analyzed with HPLC.

(3S)-3-(9-Fluorenyl)methoxycarbonylamino-4-n-propoxybutyric acid

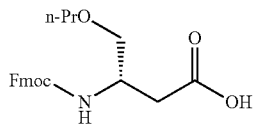

Optical purity: 99.9% ee (detection wavelength 205 nm, retention time: 3.21 min., condition 3 for high performance liquid chromatography)
UV intensity ratio: 24.6% (detection wavelength 205 nm, retention time 2.67 min., condition 2 for high performance liquid chromatography)
ESI (LC/MS negative mode) m/z: 428.42 (M+HCO$_2^-$)

T-Butyl (3S)-3-(9-fluorenyl)methoxycarbonylamino-4-n-propoxybutyrate

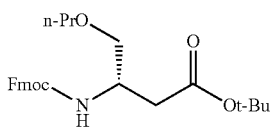

Optical purity: 99.9% ee (detection wavelength 205 nm, retention time: 3.89 min., condition 3 for high performance liquid chromatography)
UV intensity ratio: 29.9% (detection wavelength 205 nm, retention time 3.61 min., condition 2 for high performance liquid chromatography)
ESI (LC/MS positive mode) m/z: 440.70 (M+H$^+$)

Example 36: (3S)-3-(9-Fluorenyl)methoxycarbonylamino-4-i-propoxybutyric acid (with sodium dihydrogenphosphate

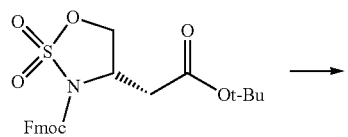

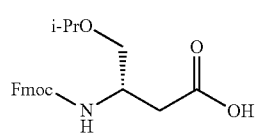

A mixture consisting of t-butyl (4S)-5-(9-fluorenyl)methoxycarbonyl-1,2,5-sulfamidate-4-acetate 30 mg (0.065 mmol), sodium dihydrogenphosphate 30 mg, and 2-propanol 0.6 mL was stirred for 2 hours while heating at 70° C., and the reaction mixture was analyzed with HPLC.

(3S)-3-(9-Fluorenyl)methoxycarbonylamino-4-i-propoxybutyric acid

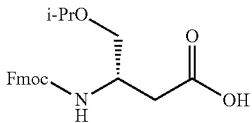

Optical purity: 99.9% ee (detection wavelength 205 nm, retention time: 3.16 min., condition 3 for high performance liquid chromatography)
UV intensity ratio: 7.2% (detection wavelength 205 nm, retention time 2.64 min., condition 2 for high performance liquid chromatography)
ESI (LC/MS negative mode) m/z: 382.63 (M–H$^+$)

T-Butyl (3S)-3-(9-fluorenyl)methoxycarbonylamino-4-i-propoxybutyrate

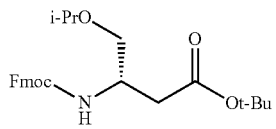

Optical purity: 99.9% ee (detection wavelength 205 nm, retention time: 3.82 min., condition 3 for high performance liquid chromatography)
UV intensity ratio: 22.2% (detection wavelength 205 nm, retention time 3.57 min., condition 2 for high performance liquid chromatography)
ESI (LC/MS positive mode) m/z: 440.70 (M+H+)

Production example using benzyl (2S)-3-(9-fluorenyl)methoxycarbonylamino-2-hydroxymethylpropionate as a starting material Example 37: Benzyl (5S)-3-(9-fluorenyl)methoxycarbonyl-2,2-dioxo-1,2,3-oxathiazinane-5-carboxylate

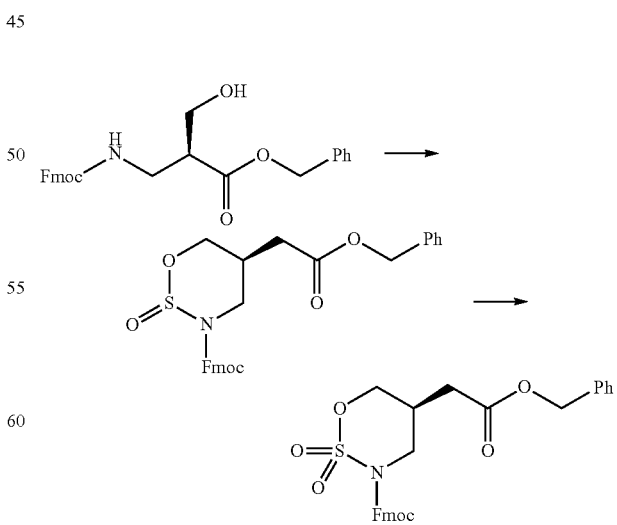

1) To a solution consisting of thionyl chloride 2.38 g (20.0 mmol) and ethyl acetate 80 mL cooled to –40° C., a solution consisting of benzyl (2S)-3-(9-fluorenyl)methoxycarbonylamino-2-hydroxymethylpropionate 4.32 g (10.0 mmol) and dichloromethane 12 mL is added dropwise over 5 minutes. The reaction mixture is stirred at the same temperature for 5 minutes, and then pyridine 3.96 g (50.0 mmol) is added dropwise over 5 minutes. The reaction mixture is stirred at −40° C. for 5 minutes And then at room temperature for 2 hours. To the reaction mixture, water 40 mL is added, and the organic layer and the aqueous layer are separated. To the organic layer obtained, 1N HCl 40 mL is added, and the mixture is separated into the organic layer and the aqueous layer again. The organic layer obtained is washed with 10% brine 40 mL, and concentrated under reduced pressure to give benzyl (5S)-3-(9-fluorenyl) methoxycarbonyl-2,2-dioxo-1,2,3-oxathiazinane-5-carboxylate as a crude product of a diastereomeric mixture.

2) To a solution consisting of the crude product of benzyl (5S)-3-(9-fluorenyl)methoxycarbonyl-2,2-dioxo-1,2,3-oxathiazinane-5-carboxylate and acetonitrile 20 mL cooled to −10° C., a solution consisting of sodium periodate 3.21 g (15.0 mmol), ruthenium chloride hydrate 21 mg (0.1 mmol), and water 60 mL is added dropwise over 10 minutes. The reaction mixture is stirred at −20° C. for 5 minutes, and then at room temperature for 3 hours. To the reaction mixture, sodium carbonate 1.20 g (11.3 mmol), water 60 mL, and ethyl acetate 90 mL are added, and the mixture is separated into the organic layer and the aqueous layer. The organic layer obtained is washed with a mixture consisting of NaCl 6.00 g (102 mmol) and water 54 mL, and concentrated under reduced pressure to give benzyl (5S)-3-(9-fluorenyl) methoxycarbonyl-2,2-dioxo-1,2,3-oxathiazinane-5-carboxylate as a crude product.

Example 38: Benzyl (2S)-2-(9-fluorenyl)methoxycarbonylaminomethyl-3-n-propoxypropionate (with sodium dihydrogenphosphate

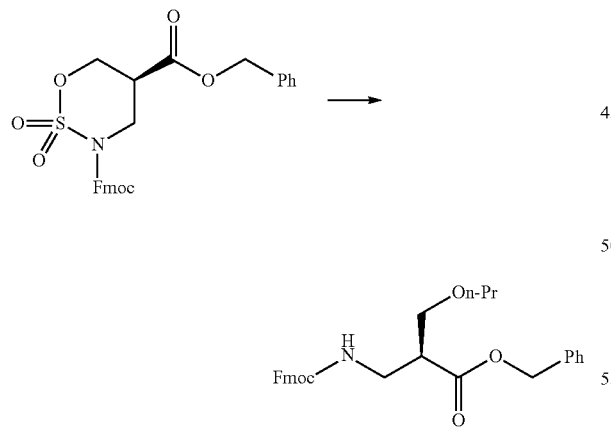

A mixture consisting of benzyl (5S)-3-(9-fluorenyl)methoxycarbonyl-2,2-dioxo-1,2,3-oxathiazinane-5-carboxylate 50 mg (0.104 mmol), sodium dihydrogenphosphate 50 mg, and 1-propanol 1 mL is stirred for 2 hours while heating at 70° C., and the reaction mixture is analyzed with HPLC.

Example 39: Benzyl (2S)-2-(9-fluorenyl)methoxycarbonylaminomethyl-3-i-propoxypropionate (with sodium dihydrogenphosphate

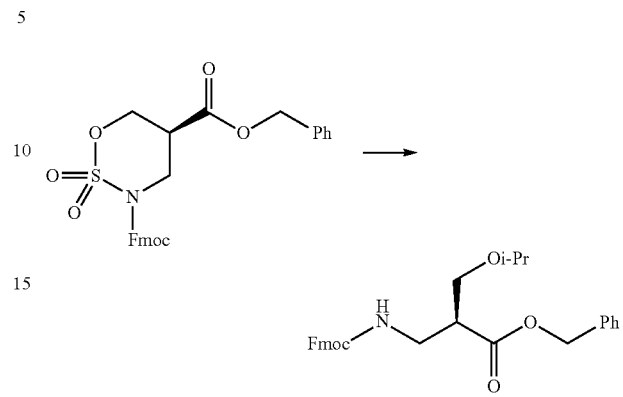

A mixture consisting of benzyl (5S)-3-(9-fluorenyl)methoxycarbonyl-2,2-dioxo-1,2,3-oxathiazinane-5-carboxylate 50 mg (0.104 mmol), sodium dihydrogenphosphate 50 mg, and 2-propanol 1 mL is stirred for 2 hours while heating at 70° C., and the reaction mixture is analyzed with HPLC.

Production example using benzyl (2R)-3-(9-fluorenyl) methoxycarbonylamino-2-hydroxymethylpropionate as a starting material Example 40: Benzyl (5R)-3-(9-fluorenyl)methoxycarbonyl-2,2-dioxo-1,2,3-oxathiazinane-5-carboxylate

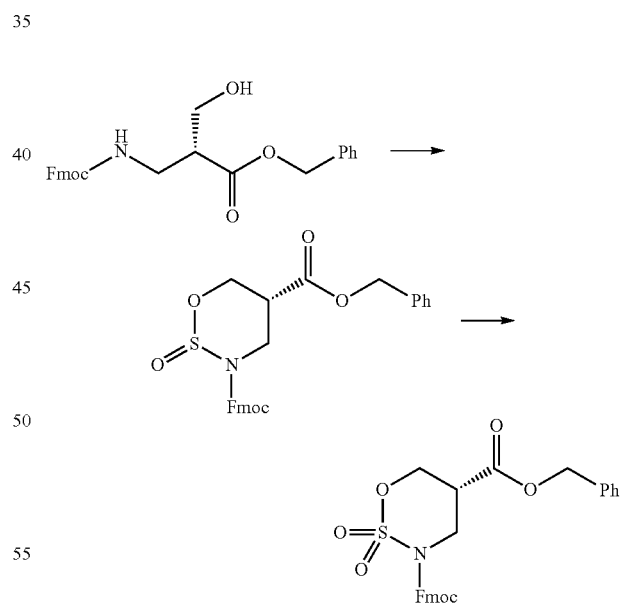

1) To a solution consisting of thionyl chloride 2.38 g (20.0 mmol) and ethyl acetate 80 mL cooled to −40° C., a solution consisting of benzyl (2R)-3-(9-fluorenyl)methoxycarbonylamino-2-hydroxymethylpropionate 4.32 g (10.0 mmol) and dichloromethane 12 mL is added dropwise over 5 minutes. The reaction mixture is stirred at the same temperature for 5 minutes, and then pyridine 3.96 g (50.0 mmol) is added dropwise over 5 minutes. The reaction mixture is stirred at −40° C. for 5 minutes and then at room temperature for 2 hours. To the reaction mixture, water 40 mL is added, and the mixture is separated into the organic layer and the aqueous layer. To the organic layer obtained, 1N HCl 40 mL is added, and the obtained mixture is separated into the organic layer and the aqueous layer again. The organic layer obtained is washed with 10% brine 40 mL, and concentrated under reduced pressure to give benzyl (5R)-3-(9-fluorenyl)methoxycarbonyl-2,2-dioxo-1,2,3-oxathiazinane-5-carboxylate as a crude product of a diastereomeric mixture.

2) To a solution consisting of the crude product of benzyl (5R)-3-(9-fluorenyl)methoxycarbonyl-2,2-dioxo-1,2,3-oxathiazinane-5-carboxylate and acetonitrile 20 mL cooled to −10° C., a solution consisting of sodium periodate 3.21 g (15.0 mmol), ruthenium chloride hydrate 21 mg (0.1 mmol), and water 60 mL is added dropwise over 10 minutes. The reaction mixture is stirred at −20° C. for 5 minutes, and then at room temperature for 3 hours. To the reaction mixture, sodium carbonate 1.20 g (11.3 mmol), water 60 mL, and ethyl acetate 90 mL are added, and the mixture is separated into the organic layer and the aqueous layer. The organic layer obtained is washed with a mixture consisting of NaCl 6.00 g (102 mmol) and water 54 mL, and concentrated under reduced pressure to give benzyl (5R)-3-(9-fluorenyl)methoxycarbonyl-2,2-dioxo-1,2,3-oxathiazinane-5-carboxylate as a crude product.

Example 41: Benzyl (2R)-2-(9-fluorenyl)methoxycarbonylaminomethyl-3-n-propoxypropionate (with sodium dihydrogenphosphate

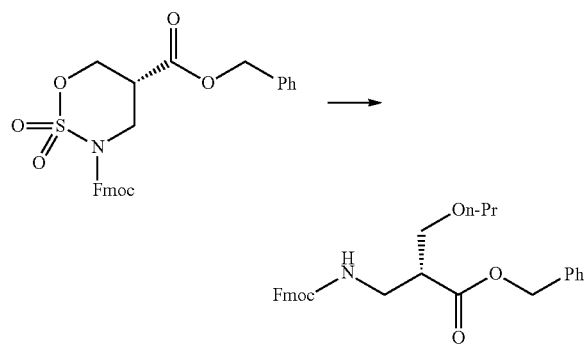

A mixture consisting of benzyl (5R)-3-(9-fluorenyl)methoxycarbonyl-2,2-dioxo-1,2,3-oxathiazinane-5-carboxylate 50 mg (0.104 mmol), sodium dihydrogenphosphate 50 mg, and 1-propanol 1 mL is stirred for 2 hours while heating at 70° C., and the reaction mixture is analyzed with HPLC.

Example 42: Benzyl (2R)-2-(9-fluorenyl)methoxycarbonylaminomethyl-3-i-propoxypropionate (with sodium dihydrogenphosphate

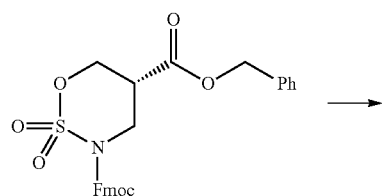

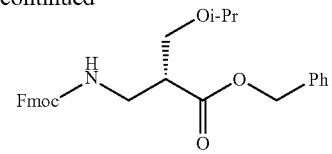

A mixture consisting of benzyl (5R)-3-(9-fluorenyl)methoxycarbonyl-2,2-dioxo-1,2,3-oxathiazinane-5-carboxylate 50 mg (0.104 mmol), sodium dihydrogenphosphate 50 mg, and 2-propanol 1 mL is stirred for 2 hours while heating at 70° C., and the reaction mixture is analyzed with HPLC.

INDUSTRIAL APPLICABILITY

The present invention provides novel methods for producing O-substituted serine derivatives. Using the production methods of the present invention, unnatural amino acids useful for exploring peptide pharmaceuticals, and/or for supplying active ingredients of pharmaceuticals can be provided with high regioselectivity, chemical yield, and optical purity.

The invention claimed is:
1. A method for producing a compound represented by general formula (I):

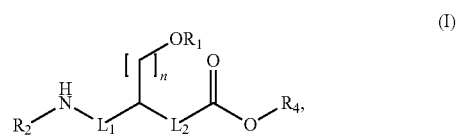

its chemically acceptable salt, or a solvate thereof,
the method comprising the following steps:
Step A: reacting a compound represented by general formula (V):

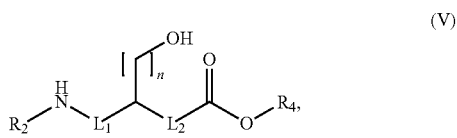

its chemically acceptable salt, or a solvate thereof, with a cyclization reagent to obtain a compound represented by general formula (IV):

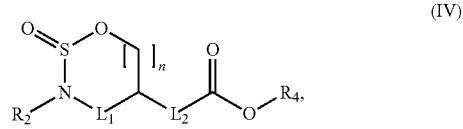

its chemically acceptable salt, or a solvate thereof,
Step B: reacting the compound represented by general formula (IV), its chemically acceptable salt, or a solvate thereof, with an oxidizing agent to obtain a compound represented by general formula (II):

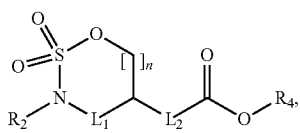

(II)

its chemically acceptable salt, or a solvate thereof, and

Step C: reacting the compound represented by general formula (II), its chemically acceptable salt, or a solvate thereof, with R1OH to obtain the compound represented by general formula (I), its chemically acceptable salt, or a solvate thereof, wherein, $R_1$ is optionally substituted $C_1$-$C_6$ alkyl, optionally substituted $C_3$-$C_8$ cycloalkyl, optionally substituted aralkyl, or optionally substituted heteroaralkyl, $R_2$ is $C_1$-$C_6$ alkyl or an amino protecting group, $R_4$ is a carboxyl protecting group, $L_1$ is a single bond or —$CH_2$—, $L_2$ is a single bond or —$CH_2$—, and n is 1 or 2, with the proviso that when $L_1$ is —$CH_2$—, $L_2$ is a single bond, and when $L_2$ is —$CH_2$—, $L_1$ is a single bond.

2. A method for producing a compound represented by general formula (I):

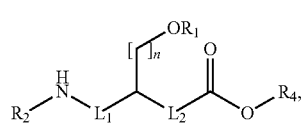

(I)

its chemically acceptable salt, or a solvate thereof, the method comprising the following steps:

Step A: reacting a compound represented by general formula (V'):

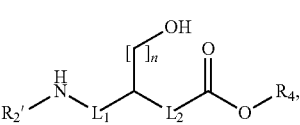

(V')

its chemically acceptable salt, or a solvate thereof, with a cyclization reagent to obtain a compound represented by general formula (IV'):

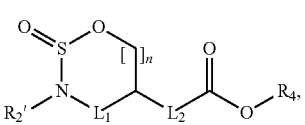

(IV')

its chemically acceptable salt, or a solvate thereof,

Step B: reacting the compound represented by general formula (IV'), its chemically acceptable salt, or a solvate thereof, with an oxidizing agent to obtain a compound represented by general formula (II'):

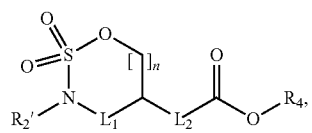

(II')

its chemically acceptable salt, or a solvate thereof, and

Step C: reacting the compound represented by general formula (II'), its chemically acceptable salt, or a solvate thereof, with $R_1OH$ to obtain the compound represented by general formula (I), its chemically acceptable salt, or a solvate thereof, wherein, $R_1$ is optionally substituted $C_1$-$C_6$ alkyl, optionally substituted $C_3$-$C_8$ cycloalkyl, optionally substituted aralkyl, or optionally substituted heteroaralkyl, $R_2$ is a hydrogen, $R_2'$ is an amino protecting group, $R_4$ is a carboxyl protecting group, $L_1$ is a single bond or —$CH_2$—, $L_2$ is a single bond or —$CH_2$—, and n is 1 or 2, with the proviso that when $L_1$ is —$CH_2$—, $L_2$ is a single bond, and when $L_2$ is —$CH_2$—, $L_1$ is a single bond.

3. The method of claim 1, wherein $R_1$ is $C_1$-$C_6$ alkyl, $C_3$-$C_8$ cycloalkyl, aralkyl, or heteroaralkyl, each of which is optionally substituted with one or more substituents independently selected from halogen, hydroxyl, and aryl that is optionally substituted with halogen, $R_2$ is selected from Boc, Fmoc, Cbz, or Alloc, and $R_4$ is benzyl or tert-Bu.

4. The method of claim 2, wherein $R_1$ is $C_1$-$C_6$ alkyl, $C_3$-$C_8$ cycloalkyl, aralkyl, or heteroaralkyl, each of which is optionally substituted with one or more substituents independently selected from halogen, hydroxyl, and aryl that is optionally substituted with halogen, $R_2'$ is selected from Boc, Fmoc, Cbz, or Alloc, and $R_4$ is benzyl or tert-Bu.

5. The method of claim 1, wherein the oxidizing agent used in Step B is a combination of periodate and ruthenium catalyst.

6. The method of claim 5, wherein periodate that is 1.5 to 5 equivalents and ruthenium catalyst that is 0.01 to 0.2 equivalents to the compound represented by general formula (IV), its chemically acceptable salt, or a solvate thereof, are used.

7. The method of claim 1, wherein Step B is performed in a solvent mixture of acetonitrile and water.

8. The method of claim 1, wherein Step C is performed in the presence of an acid salt.

9. The method of claim 1, wherein Step C is performed in 2,2,2-trifluoroethanol, 1,1,1,3,3,3-hexafluoro-2-propanol, or 2-methyltetrahydrofuran.

10. The method of claim 1, wherein Step A is performed in ethyl acetate, isopropyl acetate, or butyl acetate, and thionyl chloride that is 1.5 to 5 equivalents to the compound represented by general formula (V), its chemically acceptable salt, or a solvate thereof, is used.

11. The method of claim 2, wherein the oxidizing agent used in Step B is a combination of periodate and ruthenium catalyst.

12. The method of claim 11, wherein periodate that is 1.5 to 5 equivalents and ruthenium catalyst that is 0.01 to 0.2 equivalents to the compound represented by general formula (IV'), its chemically acceptable salt, or a solvate thereof, are used.

13. The method of claim 2, wherein Step B is performed in a solvent mixture of acetonitrile and water.

14. The method of claim 2, wherein Step C is performed in the presence of an acid salt.

15. The method of claim 2, wherein Step C is performed in 2,2,2-trifluoroethanol, 1,1,1,3,3,3-hexafluoro-2-propanol, or 2-methyltetrahydrofuran.

16. The method of claim 2, wherein Step A is performed in ethyl acetate, isopropyl acetate, or butyl acetate, and thionyl chloride that is 1.5 to 5 equivalents to the compound represented by general formula (V'), its chemically acceptable salt, or a solvate thereof, is used.

* * * * *